United States Patent [19]

Horwell et al.

[11] Patent Number: 5,331,006

[45] Date of Patent: Jul. 19, 1994

[54] AMINO ACID ANALOGS AS CCK ANTAGONISTS

[75] Inventors: David C. Horwell, Cambridge, England; Julian Aranda, Vörstetten, Fed. Rep. of Germany; Corinne Augelli-Szafran, Ypsilanti, Mich.; Hans-Jurgen Betche, Vörstetten, Fed. Rep. of Germany; Ann Holmes, Dexter; Michael D. Mullican, Ypsilanti, both of Mich.; Martyn C. Pritchard, Cambridge, England; Reginald S. Richardson, Haverhill, England; Edward Roberts, Newmarket, England; Bruce D. Roth, Ann Arbor, Mich.; Bradley D. Tait, Canton, Mich.; Bharat K. Trivedi, Farmington Hills, Mich.; Uwe Trostmann, March-Hugstetten, Fed. Rep. of Germany; Paul C. Unangst, Ann Arbor, Mich.

[73] Assignee: Warner-Lambert Company, Morris Plains, N.J.

[21] Appl. No.: 726,656

[22] Filed: Jul. 12, 1991

Related U.S. Application Data

[63] Continuation-in-part of Ser. No. 576,308, Aug. 31, 1990, abandoned.

[51] Int. Cl.$^5$ .................... A61K 31/27; C07C 271/10
[52] U.S. Cl. .................... 514/481; 514/487; 560/27; 560/28
[58] Field of Search .................... 560/27, 28; 514/481, 514/484, 485, 487, 490

[56] References Cited

U.S. PATENT DOCUMENTS 4,241,064 12/1980 Matsumura et al. ................ 424/256
4,705,856 11/1987 Biere ................................. 546/21

OTHER PUBLICATIONS

Thaisrivongs et al "Renin Inhibitory Peptides: A Study of Structural Modifications in the Peptide Backbone" CA 111:89774m (1989).

*Primary Examiner*—Celia Chang
*Attorney, Agent, or Firm*—Elizabeth M. Anderson

[57] ABSTRACT

Novel unnatural dipeptoids useful as agents in the treatment of obesity, hypersecretion of gastric acid in the gut, gastrin-dependent tumors, or as antipsychotics are disclosed. Further, the compounds are antianxiety agents and antiulcer agents. The compounds are agents useful for preventing the response to withdrawal from chronic treatment or use of nicotine, diazepam, alcohol, cocaine, caffeine, and opioids. The compounds are also useful in treating and/or preventing panic attacks. Also disclosed are pharmaceutical compositions and methods of treatment using the dipeptoids as well as processes for preparing them and novel intermediates useful in their preparation. An additional feature of the invention is the use of the subject compounds to prepare diagnostic compositions.

24 Claims, No Drawings

AMINO ACID ANALOGS AS CCK ANTAGONISTS

CROSS-REFERENCE TO RELATED APPLICATION

This application is a continuation-in-part application of U.S. Ser. No. 07/576,308, filed Aug. 31, 1990, now abandoned.

BACKGROUND OF THE INVENTION

Agents acting as agonists at central cholecystokinin (CCK) receptors may induce satiety (Schick, Yaksh, and Go, *Regulatory Peptides* 14:277-291, 1986). They are also expected to act as analgesics (Hill, Hughes, and Pittaway, *Neuropharmacology* 26:289-300, 1987), and as anticonvulsants (MacVicar, Kerrin, and Davison, *Brain Research* 406:130-135, 1987).

Reduced levels of CCK-peptides have been found in the brains of schizophrenic patients compared with controls (Roberts, Ferrier, Lee, Crow, Johnston, Owens, Bacarese-Hamilton, McGregor, O'Shaughnessey, Polak, and Bloom, *Brain Research* 288:199-211, 1983). It has been proposed that changes in the activity of CCK neurones projecting to the nucleus accumbens may play a role in schizophrenic processes by influencing dopaminergic function (Totterdell and Smith, *Neuroscience* 19:181-192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309-317, 1988; Schneider, Allpert, and Iversen, *Peptides* 4:749-753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, ed. G. B. J. Glass, Raven Press, N.Y., Ch. 23, pp. 529-564, 1980). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, ibid., pp. 507-527), actions which are associated with increased DNA and RNA synthesis. Moreover, gastrin-secreting cells are associated with certain gastrointestinal tumors as in the Zollinger-Ellison syndrome (Stadil, ibid., pp. 729-739), and some colorectal tumors may also be gastrin/CCK dependent (Singh, Walker, Townsend, and Thompson, *Cancer Research* 46:1612, 1986; Smith, *Gastroenterology* 95:1541, 1988). Antagonists of CCK/gastrin receptors could, therefore, be of therapeutic value as antitumor agents.

The CCK peptides are widely distributed in various organs of the body, including the gastrointestinal tract, endocrine glands, and the nerves of the peripheral and central nervous systems. Various biologically active forms have been identified, including a 33-amino acid hormone and various carboxyl-terminus fragments of this peptide (e.g., the octapeptide CCK26-33 and the tetrapeptide CCK30-33) (Dockray, *Br. Med. Bull.* 38(3):253-258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions, and other behavioral effects (*Cholecystokinin: Isolation, Structure and Functions*, G. B. J. Glass, ed., Raven Press, New York, pp. 169-221, 1980; Morley, *Life Sciences* 27:355-368, 1980; *Cholecystokinin in the Nervous System*, J. de Belleroche and G. J. Dockray, eds., Ellis Horwood, Chichester, England, pp. 110-127, 1984).

The high concentrations of CCK peptides in many brain areas also indicate major brain functions for these peptides (Dockray, *Br. Med. Bull.* 38(3):253-258, 1982). The most abundant form of brain CCK found is CCK26-33, although small quantities of CCK30-33 exist (Rehfeld and Gotterman, *J. Neurochem.* 32:1139-1341, 1979). The role of central nervous system CCK is not known with certainty, but it has been implicated in the control of feeding (Della-Fera and Baile, *Science* 206:471-473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (DeMeulemeester, et al, *J. Neuroscience* 8:988-1000, 1988). Agents that modify GABA action may have utility as anxiolytic or hypnotic agents (S. C. Harvey, *The Pharmacological Basis of Therapeutics* (7th ed.), pp. 339-371, 1985, MacMillan). Thus, agents which modify CCK action may have parallel anxiolytic or hypnotic activities. *TIPS* 11:271, 1990 discloses the role of CCK antagonists.

SUMMARY OF THE INVENTION

The invention relates to novel compounds of the formula

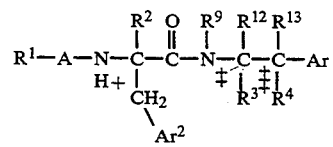

and the pharmaceutically acceptable salts thereof wherein $R^1$, $R^2$, $R^3$, $R^4$, $R^9$, $R^{12}$, $R^{13}$, A, Ar and $Ar^2$ are as defined hereinbelow.

In commonly owned copending applications Ser. Nos. 07/576,628, 07/576,296, 07/576,315, 07/576,024, and 07/576,297, filed on Aug. 31, 1990 by Horwell, et al, the disclosures of which are incorporated herein by reference, CCK antagonists are disclosed.

In the continuation-in-part applications of the above applications also commonly owned and copending Ser. Nos. 726,655, 726,654, 726,653, 726,652, and 726,651, filed on even date herewith by Horwell, et al, the disclosures of which are incorporated herein by reference, CCK antagonists are disclosed.

In like manner, the present invention also relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

An additional use for suitably radiolabeled iodinated compounds is that a suitably radiolabeled derivative such as iodine-131 or iodine-127 isotope gives an agent suitable for treatment of gastrin-dependent tumors such as those found in colonic cancers. Such radiolabeled compounds can also be used as a diagnostic agent by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula K in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, caffeine, opioids, alcohol, and nicotine. Withdrawal symptoms are treated by administration of an effective withdrawal treating amount of a compound of the instant invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION OF THE INVENTION

The compounds of the present invention are formed by the condensation of two modified amino acids and are therefore not peptides. Rather, they are "dipeptoids", synthetic peptide-related compounds differing from natural dipeptides in that the substituent group $R^2$ is not hydrogen.

The compounds of the present invention are represented by the formula

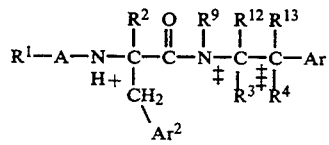

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and —$(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six; A is —$(CH_2)_nCO$—, —$SO_2$—, —$S(=O)$—, —NHCO—, $$-(CH_2)_n-\overset{O}{\underset{\|}{O}}C-, \quad -\overset{O}{\underset{\|}{S}}C-,$$

—O—$(CH_2)_nCO$—, or —HC=CHCO— wherein n is an integer from zero to six;

$R^2$ is a straight or branched alkyl of from one to about six carbon atoms, —HC=$CH_2$, —C≡CH, —$(CH_2)_n$—CH=$CH_2$, —$(CH_2)_nC$≡CH, —$(CH_2)_nAr$, —$(CH_2)_nOR^*$, —$(CH_2)_nOAr$, —$(CH_2)_nCO_2R^*$ or —$(CH_2)_nNR^5R^6$ wherein n R*, $R^5$, and $R^6$ are as defined above and Ar is as defined below;

$R^3$ and $R^4$ are each independently selected from hydrogen, $R^2$ and —$(CH_2)_{n'}$—β—D wherein:

n' is an integer of from zero to three;

β is a bond,
—OCO$(CH_2)_n$—,
—O$(CH_2)_n$—,
—NHCO$(CH_2)_n$—,
—CONH$(CH_2)_n$—,
—NHCOCH=CH—,
—COO$(CH_2)_n$—,
—CO$(CH_2)_n$—,
—S—$(CH_2)_n$—,
—S(=O)—$(CH_2)_n$—,
—$SO_2$—$(CH_2)_n$—,
—$NHSO_2(CH_2)_n$—,
—$SO_2NH(CH_2)_n$—, $$\text{NHCO}-\underset{R^7}{\overset{}{C}}=\underset{R^8}{\overset{}{C}}-, \quad \text{CONH}-\underset{R^7}{\overset{}{C}}=\underset{R^8}{\overset{}{C}}-,$$

$$\text{NHCO}-\underset{R^7}{\overset{H}{\underset{|}{C}}}-\underset{R^8}{\overset{H}{\underset{|}{C}}}-, \quad \text{CONH}-\underset{R^7}{\overset{H}{\underset{|}{C}}}-\underset{R^8}{\overset{H}{\underset{|}{C}}}-$$

wherein $R^7$ or $R^8$ are independently selected from hydrogen and $R^2$ or together form a ring $(CH_2)_m$ wherein m is an integer of from 1 to 5 and n is as defined above;

D is
—COOR*,
—$CH_2OR^*$,
—$CHR^2OR^*$,
—$CH_2SR^*$,
—$CHR^2SR^*$,
—$CONR^5R^6$,
—CN,
—$NR^5R^6$,
—OH,
—H and acid replacements such as tetrazole wherein m is an integer of from 0 to 2,
wherein R*, $R^2$, $R^5$, and $R^6$ are as defined above;

$R^9$ is hydrogen or a straight or branched alkyl of from one to about six carbon atoms, —$(CH_2)_nCO_2R^*$, —$(CH_2)_nOAr'$, —$(CH_2)_nNR^5R^6$, wherein n, R*, $R^5$, and $R^6$ are as defined above or taken from $R^3$ and Ar' is taken from Ar as defined below;

$R^{12}$ and $R^{13}$ are each independently hydrogen or are each independently taken with $R^3$ and $R^4$, respectively, to form a moiety doubly bonded to the carbon atom;

Ar is a mono- or polycyclic unsubstituted or substituted carbo- or heterocyclic aromatic or carbo- or heteroaromatic moiety; and $Ar^2$ can be selected from Ar as defined above or the $CH_2Ar^2$ moiety of formula I is the sidechain of a biologically significant amino acid, with the proviso that $Ar^2$ cannot be

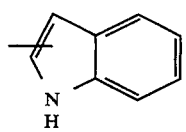

Ar² is also —(CH₂)₂NHC(=NH)NHNO₂, —(CH₂)₂-NMe₂, or —CH₂CO₂CH₃.

Preferred compounds of the instant invention are those wherein

R¹ is a cycloalkyl or a polycycloalkyl of from about six to about ten carbon atoms with from zero to four substituents each independently selected from hydrogen, straight or branched alkyl of from one to six carbon atoms, CF₃, NR⁵R⁶, —(CH₂)ₙCO₂R* CN, F, Cl, Br, OR*, SR*, wherein R*, R⁵, and R⁶ are as defined in claim 1 and n is an integer of from 1 to 3;

A is —NHCO—, OC(=O)—, —S(=O), —SO₂—, —SCO— or —CH₂CO—;

R² is —CH₃, —CH₂CO₂H, or —CH₂C≡CH;

R³ is —(CH₂)ₙ′—β—D or H;

R⁴ is —(CH₂)ₙ′—β—D or H;

R⁹ is hydrogen or methyl;

R¹² is hydrogen;

R¹³ is hydrogen;

Ar is a monocyclic 5- or 6-member ring having from 0 to 4 heteroatoms each independently nitrogen, oxygen, or sulfur, a bicyclic ring system wherein each ring is independently a 5- or 6-member ring containing from 0 to 3 heteroatoms each independently selected from nitrogen, oxygen, and sulfur, a tricyclic ring system wherein each ring is independently a 5- or 6-member ring containing from 0 to 5 heteroatoms selected from nitrogen, oxygen, sulfur, or a hydroaromatic ring;

Ar² is a monocyclic 5- or 6-member ring having from 0 to 4 heteroatoms each independently nitrogen, oxygen, or sulfur, a bicyclic ring system wherein each ring is independently a 5- or 6-member ring containing from 0 to 3 heteroatoms, each independently selected from nitrogen, oxygen, and sulfur, a tricyclic ring system wherein each ring independently is a 5- or 6-member ring containing from 0 to 5 heteroatoms selected from nitrogen, oxygen, and sulfur, a hydroaromatic ring, an alkyl carboxylic acid, or an alkyl amine with the proviso that Ar² cannot be 2- or 3-indole.

More preferred compounds of the instant invention are those wherein

R₁ is an unsubstituted or substituted cycloalkyl or polycycloalkyl

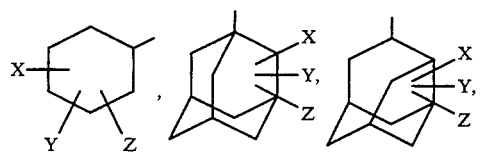

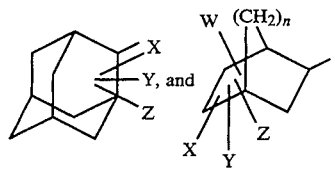

wherein W, X, Y, and Z are each independently hydrogen, a straight or branched alkyl of from one to six carbon atoms, CF₃, NR⁵N⁶, —(CH₂)ₙCO₂R*, CN, F, Cl, Br, OR*, SR*, wherein R*, R⁵, and R⁶ are as defined in claim 1 and n is an integer of from 1 to 3;

A is —NHCO—, OCO—, —SO₂—, —S(=O)— or —CH₂CO—;

R₂ is —CH₃, —CH₂CO₂H, or —CH₂C≡CH;

R³ is H, CH₂OH, CH₂OCOCH₂CH₂CO₂H, CH₂OCOCH=CHCO₂H, CH₂NHCOCH₂CH₂CO₂H, CH₂NHCOCH=CHCO₂H, CH₂SCH₂CO₂H, or CH₂SCH₂CH₂CO,

R⁴ is H, —NHCOCH₂CH₂CO₂H or NHCOCH=CHCO₂H,

R⁹ is H or methyl,

R¹² is hydrogen,

R¹³ is hydrogen,

Ar and Ar² are as above.

Still more preferred compounds of the instant invention are those wherein

R¹ is 2-adamantyl, 1-(S)-2-endobornyl, or 2-methylcyclohexyl;

A is —OC(=O);

R² is CH₃;

R³ is H, CH₂OH, CH₂OCOCH₂CH₂CO₂H, CH₂OCOCH=CHCO₂H, CH₂NHCOCH₂CH₂CO₂H, CH₂NHCOCH=CHCO₂H, CH₂SCH₂CO₂H, or CH₂SCH₂CH₂CO₂H,

R⁴ is H, —NHCOCH₂CH₂CO₂H ([D] configuration) or NHCOCH=CHCO₂H ([D] configuration);

R⁹ is hydrogen or methyl;

R¹² is hydrogen;

R¹³ is hydrogen;

Ar is

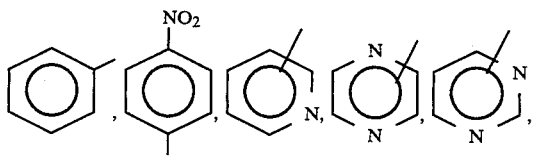

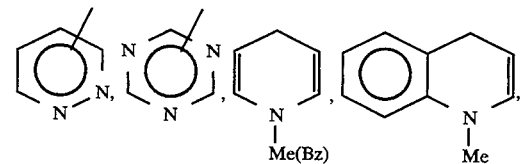

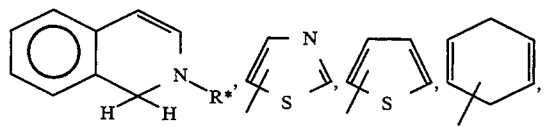

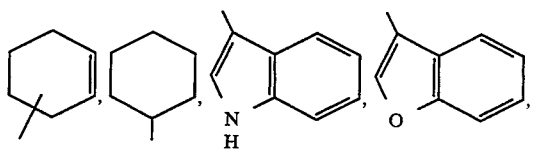
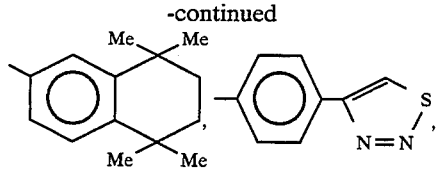
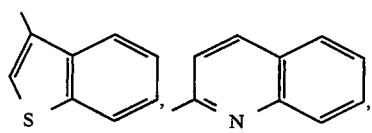
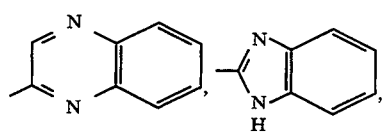
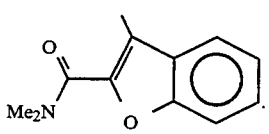
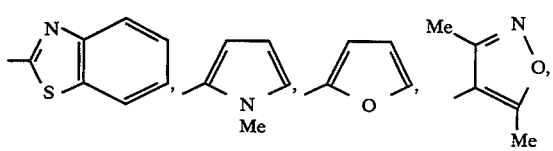
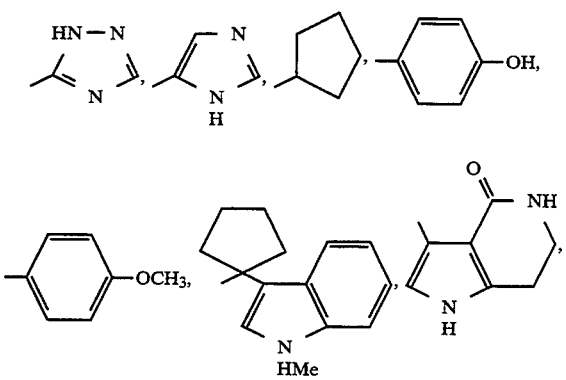
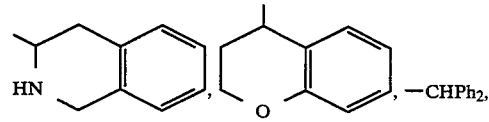
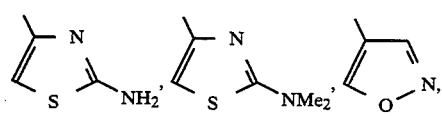
$Ar^2$ is as defined above for Ar or the $CH_2Ar^2$ moiety of formula I is the sidechain of a biologically significant amino acid.
Preferred compounds are those of formula 1 wherein $Ar^2$ is:
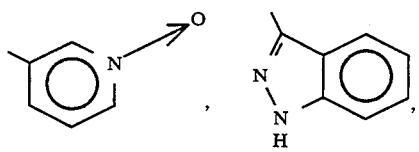
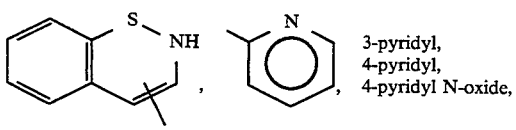 3-pyridyl, 4-pyridyl, 4-pyridyl N-oxide,
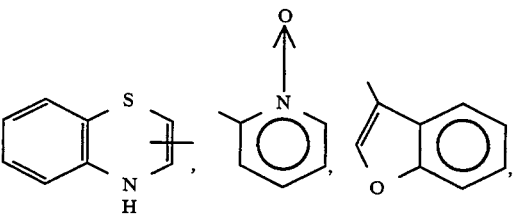
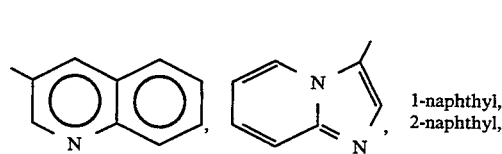 1-naphthyl, 2-naphthyl,
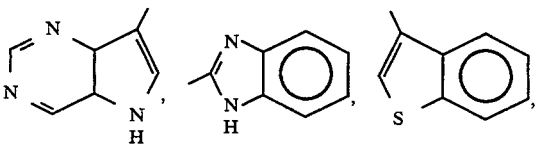
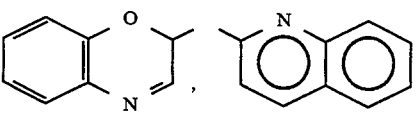

Each of the above moieties for Ar or Ar² can be independently unsubstituted, mono- or polysubstituted wherein the substituent is independently selected from NR⁵R⁶, halogen, alkyl, or alkoxy Especially preferred compounds of the instant invention are those wherein Ar² is
1-naphthyl,
2-naphthyl,
3-benzo[b]thienyl,
2-(1-BOC-benzimidazolyl),
3-(2-bromobenz[b]furanyl),
2-benzimidazolyl,
3-benzo[b]furanyl,
2-quinolinyl,
3-qunolinyl,
4-quinolinyl,
2-pyridyl,
3-pyridyl,
4-pyridyl, 1H-pyrrolo[2,3-b]pyridin-3-yl,
1H-pyrrolo[3,2-c]pyridin-3-yl,
2-dihydroquinolinyl,
2-tetrahydroquinolinyl,
3-imidazo[1,5-a]pyridinyl,
2-2,3-dihydro-1-methyl-5-phenyl-4H-1,4-benzodiazepine, or
3-indazolyl.

Most especially preferred compounds of the instant invention are:

Tricyclo[3.3.1.1$^{3,7}$]dec-2-yl[2-[[1-(hydroxymethyl)-2-phenylethyl]amino]-1-methyl-2-oxo-1-(9H-pyrido[3,4-b]indol-3-ylmethyl)ethyl]-carbamate (alanine center is RS, other center is S), Tricyclo[3.3.1.1$^{3,7}$]dec-2-yl[1-methyl-1-[[9-(methysulfonyl)-9H-pyrido[3,4-b]indol-3-yl]methyl]-2-oxo-2-[(2-phenylethyl)amino]ethyl]-carbamate, Tricyclo[3.3.1.1$^{3,7}$]dec-2-yl[2-[[1-(hydroxymethyl)-2-phenylethyl]amino]-1-methyl-1-[[9-(methylsulfonyl)-9H-pyrido[3,4-b]indol-3-yl]methyl]-2-oxoethyl[carbamate (phenylmethyl center S, other center RS), 4-[[2-[[2-methyl-1-oxo-2-(2-quinolinyl)-2-[[tricyclo[3.3.1.1$^{3,7}$]dec-2-yloxy)carbonyl]amino]propyl]amino]-1-phenylethyl]amino]-4-oxobutanoic acid (mixture of [R-(R*,R*)] and R-(R*,S*)]isomers), Butanoic acid, 4-[[2-(4-quinolinylmethyl)-1-oxo-2-[[(tricyclo[3.3.1.1$^{3,7}$]dec-2-yloxy)carbonyl]amino]propyl]amino-1-phenylethyl]amino]-4-oxo-,[R-(R*,R*)]-, Butanoic acid, 4-[[2-[2—(1,2,3,4-tetrahydro)quinolinylmethyl]-1-oxo-2-[[(tricyclo[3.3.1.1$^{3,7}$]dec-2-yloxy)-carbonyl]amino]propyl ]amino]-1-phenylethyl-]amino]-4-oxo-, Butanoic acid, 4-[[2-[2-(1,2-dihydro) quinolinylmethyl]-1-oxo-2-[[(tricyclo[3.3.1.1$^{3,7}$]dec-2-yloxy)carbonyl]amino]propyl]amino]-1-phenylethyl]amino]-4-oxo-, Tricyclo[3.3.1.1$^{3,7}$]dec-2-yl[2-[[1-(hydroxymethyl)-2-phenylethyl]amino]-1-methyl-1-(1-naphthalenylmethyl)-2-oxoethyl[carbamate (naphthalenylmethyl center is RS, other center is S), Tricyclo[3.3.1.1$^{3,7}$]dec-2-yl[2-[[1-hydroxymethyl)-2-phenylethyl]amino]-1-methyl-1-(2-naphthalenylmethyl)-2-oxoethyl]carbamate (naphthalene center is RS, hydroxymethyl center is S), Tricyclo[3.3.1.1$^{3,7}$]dec-2-yl(±)-[1-methyl-1-(1-naphthalenylmethyl)-2-oxo-2-[(2-phenylethyl)amino]ethyl]carbamate, Tricyclo[3.3.1.1$^{3,7}$]dec-2-yl(±)-[1-methyl-1-(2-naphthalenylmethyl)-2-oxo-2-[(2-phenylethyl)-amino]ethyl]carbamate, Tricyclo[3.3.1.1$^{3,7}$]dec-2-yl[2-[[1-(hydroxymethyl)-2-phenylethyl]amino]-1-methyl-1-(2-naphthalenylmethyl)-2-oxoethyl]carbamate (hydroxy center is S, other center is R or S) (Isomer I), Tricyclo[3.3.1.1$^{3,7}$]dec-2-yl(±)[1-(3-benzofuranylmethyl)-1-methyl-2-oxo-2-[(2-phenylethy)amino]ethyl]-carbamate, Tricyclo[3.3.1.1$^{3,7}$]dec-2-yl[1-(3-benzofuranylmethyl)-2-[[1-(hydroxymethyl)-2-phenylethyl]amino]-1-methyl-2-oxoethyl[carbamate (benzofuranylmethyl center is RS, other center is S), Tricyclo[3.3.1.1$^{3,7}$]dec-2-yl[1-[(2-bromo-3-benzofuranyl)methyl]-2-[[1-(hydroxymethyl)-2-phenylethyl]amino]-1-methyl-2-oxoethyl[carbamate (benzofuranylmethyl center is RS, hydroxymethyl center is S), Tricyclo[3.3.1.1$^{3,7}$]dec-2-yl(±)-[1-[(2-bromo-3-benzofuranyl)methyl]-1-methyl-2-oxo-2-[(2-phenylethyl)amino]ethyl]carbamate, 2-Methylpropyl 2-[[2-methyl-1-oxo-3-(3-pyridinyl)-2-[[(tricyclo[3.3.1.1$^{3,7}$]dec-2-yloxy)carbonyl]amino]propyl]amino]-3-phenylpropylcarbonate (pyridine center is RS, other center is S), Tricyclo[3.3.1$^{3,7}$]dec-2-yl[2-[[1-hydroxymethyl)-2-phenylethyl]amino]-1-methyl-2-oxo-1-(3-pyridinylmethyl)ethyl]carbamate (hydroxymethyl center is S, other is (±)) (Diastereomer I), Tricyclo[3.3.1.1$^{3,7}$]dec-2-yl(±)-[1-methyl-2-oxo-2-[(2-phenylethyl)amino]-1-(4-pyridinylmethyl)ethyl]carbamate, 4-[[2-[[2-methyl-1-oxo-3-(4-pyridinyl)-2-[[(tricyclo[3.3.1.1$^{3,7}$]dec-2-yloxy)carbonyl]amino]propyl]amino]-1-phenylethyl]amino]-4-oxobutanoic acid, Tricyclo[3.3.1.1$^{3,7}$]dec-2-yl[2-[[1-(hydroxymethyl)-2-phenylethyl]amino]-1-methyl-2-oxo-1-(2-pyridinylmethyl)ethyl]carbamate (hydroxymethyl center is S, other center is R or S) (Diastereomer I), Tricyclo[3.3.1.1$^{3,7}$]dec-2-yl(±)-[1-methyl-2-oxo-2-[(2-phenylethyl)amino]-1-[(2-pyridinyl)-methyl]ethyl]-carbamate, Tricyclo[3.3.1.1$^{3,7}$]dec-2-yl(±)-[1-[(2-aminophenyl)methyl]-1-methyl-2-oxo-2-[(2-phenylethyl)amino]ethyl]-carbamate, Tricyclo[3.3.1.1$^{3,7}$]dec-2-yl(±)-[1-[(2-hydroxyphenyl)-methyl]-1-methyl-2-oxo-2-[(2-phenylethyl)amino]ethyl]carbamate, Tricyclo[3.3.1.1$^{3,7}$]dec-2-yl(±)-[1-methyl-2-oxo-2-[(2-phenylethyl)amino]-1-[(2-quinolinyl)methyl]ethyl]-carbamate, Tricyclo[3.3.1.1$^{3,7}$]dec-2-yl[2-[[1-(hydroxymethyl)-2-phenylethyl]amino]-1-methyl-2-oxo-1-(4-quinolinylmethyl)ethyl]carbamate (hydroxymethyl center is S, other center is RS), Tricyclo[3.3.1.1$^{3,7}$]dec-2-yl()-[1-methyl-2-oxo-2-[(2-phenylethyl)-amino]-1-(4-quinolinylmethyl)ethyl)-carbamic acid, Tricyclo[3.3.1.1$^{3,7}$]dec-2-yl(±)-[1-methyl-2-oxo-2-[(2-phenylmethyl)amino]-1-(3-quinolinyl-methyl)ethyl]-carbamate, Tricyclo[3.3.1.1$^{3,7}$]dec-2-yl[2-[[1-(hydroxymethyl)-2-phenylethyl]amino]-1-methyl-2-oxy-1-(4-pyridinylmethyl)ethyl]carbamate (hydroxymethyl center is S, other center is R or S) (Diastereomer I), Tricyclo[3.3.1.1$^{3,7}$]dec-2-yl[2-[[1-(hydroxymethyl)-2-phenylethyl]amino]-1-methyl-2-oxo-1-(2-quinolinylmethyl)ethyl[carbamate (alanine center is RS, other center is S), Tricyclo[3.3.1.1$^{3,7}$]dec-2-yl(±)-[1-(1H-indazol-3-ylmethyl)-1-methyl-2-oxo-2-[(2-phenylethyl)amino]ethyl]-carbamate, Tricyclo[3.3.1.1$^{3,7}$]dec-2-yl[2-[[1-(hydroxymethyl)-2-phenylethyl]amino]-1-(1H-indazol-3-ylmethyl)-1-methyl-2-oxoethyl]carbamate (hydroxymethy center is S, other center is RS), Tricyclo[3.3.1.1$^{3,7}$]dec-2-yl(±)-1-[1-(1H-benzimidazol-2-ylmethyl)-1-methyl-2-oxo-2-[(2-phenylethyl)amino]ethyl]carbamate, Tricyclo[3.3.1.1$^{3,7}$]dec-2-yl-[1-(1H-benzimidazol-2-ylmethyl)-2-[[1-(hydroxymethyl)-2-phenylethyl]amino]-1-methyl-2-oxoethyl]carbamate (hydroxy center is S, other center is RS), Tricyclo[3.3.1.1$^{3,7}$]dec-2-yl-[1-(benzo[b]thien-3-ylmethyl)-2-[[1-(hydroxymethyl)-2-phenylethyl]amino]-1- methyl-2-oxoethyl]-carbamate (benzothiophene center is RS, hydroxymethyl center is S), Tricyclo[3.3.1.1$^{3,7}$]dec-2-yl($\pm$)-[1-(benzo[b]thien-3-ylmethyl)-1-methyl-2-oxo-2-[(2-phenylethyl)amino]ethyl]carbamate, Tricyclo[3.3.1.1$^{3,7}$]dec-2-yl[2-[(2-amino-2-phenylethyl)amino]-1-(1H-indazol-3-ylmethyl)- 1-methyl-2-oxoethyl]carbamate, 4-[[2-[[2-methyl-1-oxo-3-(1,2,3,4-tetrahydro-2-quinolinyl)-2-[[(tricyclo[3.3.1.1$^{3,7}$]dec-2-yloxy)carbonyl]amino]propyl]amino]-1-phenylethyl]amino]-4-oxobutanoic acid compd. with 1-deoxy-1-(methylamino)-D-glucitol, 4-[[2-[[3-(1,2-dihydro-2-quinolinyl)-2-methyl-1-oxo-2-[[(tricyclo[3.3.1.1$^{3,7}$]dec-2-yloxy)carbonyl]amino]-propyl]amino]-1-phenylethyl]amino]-4-oxobutanoic acid compd. with 1-deoxy-1-(methylamino)-D-glucitol, 4-[[2-[[2-methyl-1-oxo-3-(4-quinolinyl)-2-[[(tricyclo[3.3.1.1$^{3,7}$]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1$^{3,7}$]dec-2-yl [S-[R*(R or S),R]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl[carbamate and Tricyclo[3.3.1.1$^{3,7}$]dec-2-yl-[S-[R*(S or R),R*]]-[2-[[2-hydroxy-1-(hydroxymethy)-2-phenylethyl]amino]-1-methyl-2-oxo-1-(1H-pyrrolo[2,3-b]pyridin-3-ylmethyl)ethyl]carbamate, and Tricyclo[3.3.1.1$^{3,7}$]dec-2-yl-[1S-[1R*(S or R),2R*]]-[2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate.

Other compounds are:

Tricyclo[3.3.1.1$^{3,7}$]dec-2-yl-[1S-[1R*(R or S),2R*]]-[2-[[2-hydroxy-1-(hydroxymethyl)-2-phenylethyl]amino]-1-methyl-2-oxo-1-(1H-pyrrolo-[3,2-c]pyridin-3-ylmethyl)ethyl]carbamate, Tricyclo[3.3.1.1$^{3,7}$]dec-2-yl($\pm$)-[1-methyl-2-oxo-[(2-phenylethyl)amino]-1-(3-pyridinylmethyl)ethyl]carbamate, 2-Methylpropyl 2-[[2-methyl-1-oxo-3-(3-pyridinyl)-2-[[(tricyclo[3.3.1.1$^{3,7}$]dec-2-yloxy)carbonyl]amino]-propyl]amino]-3-phenylpropylcarbonate, N-oxide (phenylmethyl center is S, other center is RS), Tricyclo[3.3.1.1$^{3,7}$]dec-2-yl[2-[[1-hydroxymethyl)-2-phenylethyl]amino]-1-methyl-2-oxo-1-(2-pyridinylmethyl)ethyl]carbamate (hydroxymethyl center is S, other center is S or R) (Diastereomer II), Tricyclo[3.3.1.1$^{3,7}$]dec-2-yl[2-[[1-(hydroxymethyl-2-phenylethyl]amino]-1-methyl-2-oxo-1-(2-pyridinylmethyl)ethyl]carbamate, N-oxide, Tricyclo[3.3.1.1$^{3,7}$]dec-2-yl-[2-[[1-(hydroxymethyl)-2-phenylethyl]amino]-1-methyl-2-oxo-1-(3-pyridinylmethyl)ethyl]carbamate (hydroxymethyl center is S, other is ($\pm$)) (Diastereomer II), Tricyclo[3.3.1.1$^{3,7}$]dec-2-yl[2-[[1-(hydroxymethyl)-2-phenylethyl]amino]-1-methyl-2-oxo-1-(2-pyridinylmethyl)ethyl]carbamate, N-oxide (hydroxymethyl center is S, other center is S or R) (Diastereomer II), Tricyclo[3.3.1.1$^{3,7}$]dec-2-yl($\pm$)-[1-methyl-2-oxo-2-[(2-phenylethyl)amino]-1-(2-pyridinylmethyl)ethyl]carbamate, N-oxide, Tricyclo[3.3.1.1$^{3,7}$]dec-2-yl($\pm$)-[1-methyl-2-oxo-2-[(2-phenylethyl)amino]-1-(3-pyridinylmethyl)ethyl]carbamate, N-oxide, Tricyclo[3.3.1.1$^{3,7}$]dec-2-yl[2-[[1-(hydroxymethyl)-2-phenylethyl[amino]-1-methyl-2-oxo-1-(3-pyridinylmethyl)ethyl]carbamate, N-oxide (hydroxymethyl center is S, other center is S or R) (Diastereomer I), Tricyclo[3.3.1.1$^{3,7}$]dec-2-yl[2-[[1-(hydroxymethyl)-2-phenylethyl]amino]-1-methyl-2-oxo-1-(3-pyridinylmethyl)ethyl]carbamate, N-oxide (hydroxymethyl center is S, other center is R or S) (Diastereomer II), Tricyclo[3.3.1.1$^{3,7}$]dec-2-yl[2-[[2-hydroxy-1-(hydroxymethyl)-2-phenylethyl]amino]-1-methyl-2-oxo-1-[[4-(phenylmethoxy)phenyl]methyl]ethyl]carbamate (mixture of [1S-[1R*(R*),2R*]] and [1S-[1R*(S*),2R*]] isomers), Tricyclo[3.3.1.1$^{3,7}$]dec-2-yl[2-[[2-hydroxy-1-(hydroxymethyl)-2-phenylethyl]amino]-1-[(4-hydroxyphenyl)methyl]-1-methyl-2-oxoethyl]carbamate (mixture of [1S-[1R*(R*),2R*]] and [1S-[1R*(S*),2R*]] isomers), Tricyclo[3.3.1.1$^{3,7}$]dec-2-yl[2-[[2-hydroxy-1-(hydroxymethyl)-2-phenylethyl]amino]-1-[(4-methoxyphenyl)methyl]-1-methyl-2-oxoethyl]carbamate (mixture of [1S-[1R*(R*),2R*]] and [1S-[1R*(S*),2R*]] isomers), Tricyclo[3.3.1.1$^{3,7}$]dec-1-yl[2-[[2-hydroxy-1-(hydroxymethyl)-2-phenylethyl]amino]-1-methyl-2-oxo-1-[[4-(phenylmethoxy)phenyl]methyl]ethyl]carbamate (mixture of [1S-[1R*(R*),2R*]] and [1S-[1R*(S*),2R*]] isomers, Tricyclo[3.3.1.1$^{3,7}$]dec-2-yl($\pm$)-[1-methyl-2-oxo-2-[(2-phenylethyl)amino]-1-[(5,6,7,8-tetrahydro-5,5,8,8-tetramethyl-2-naphthalenyl)methyl]ethyl]carbamate, $\alpha$-Methyl-$\beta$-(3-1H-pyrrolo[3,1-c]pyridinyl)-D,L-alanine methyl ester dihydrochloride, Carbamic acid, [-[(2,3-dimethyl)-1H-pyrrol-4-ylmethyl]-1-methyl-2-oxo-2-[(2-phenylethyl)amino]ethyl-, tricyclo[3.3.1.1$^{3,7}$]dec-2-yl ester, N-[(2-Adamantyloxy)carbonyl]-3-[(2,3-dimethyl)-1H-pyrrol-4-yl)]-2-methyl-alanine, 3-[[2,3-Dimethyl-1-(4-methylphenyl)sulfonyl]-1H-pyrrol-4-yl]-2-methyl-alanine methyl ester, Carbamic acid, [1-[(2,3-dimethyl)-1H-pyrrol-4-ylmethyl]-2-[[1-(hydroxymethyl)-2-hydroxy-2-phenylethyl]amino]-1-methylethyl]-, tricyclo[3.3.1.1$^{3,7}$]dec-2-yl ester (mixture of isomers), Carbamic acid [1-(imidazo[1,5-a]pyridin-3-ylmethyl)-2-oxo-2-[(2-phenylethyl)amino]ethyl]-, tricyclo[3.3.1.1$^{3,7}$]dec-2-yl ester, Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1$^{3,7}$]dec-2-yl ester (mixture of isomers), N-[(2-Adamantyloxy)carbonyl]-3-[(2,3-dimethyl)-1H-pyrrol-4-yl)]-2-methyl-alanine, Carbamic acid, [1-[(2,3-dimethyl)-1H-pyrrol-4-ylmethyl]-2-[[1-(hydroxymethyl)-2-hydroxy-2-phenylethyl]amino]-1-methylethyl]-, tricyclo[3.3.1.1$^{3,7}$]dec-2-yl ester (mixture of isomers), N-[(2-Adamantyloxy)carbonyl]-3-(imidazo[1,5-a]-pyridin-3-yl)-2-methyl-alanine, Tricyclo[3.3.1.1$^{3,7}$]dec-2-yl [1-[(2,3-dihydro-1-methyl-5-phenyl-1H-1,4-benzodiazepin-2-yl)methyl]-1-methyl-2-[(2-phenylethyl)amino]-2-oxoethyl]carbamate, 4-[[2-[[3-(2,3-dihydro-1-methyl-5-phenyl-1H-1,4-benzodiazepin-2-yl)-2-methyl-1-oxo-2-[[(tricyclo-[3.3.1.1$^{3,7}$]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl[2-[[1-(hydroxymethyl)-2-phenylethyl]amino]-1-methyl-2-oxo-1-[4-pyridinylmethyl)ethyl]carbamate (hydroxymethyl center is S, other center is R or S (Diastereomer II), 4-[[2-[3-(1H-indazol-3-yl)-2-methyl-1-oxo-2-[[tricyclo[3.3.1.1³,⁷]dec-2-yloxy)carbonyl]amino]-propyl]amino]-1-phenylethyl]amino]-4-oxobutanoic acid (mixture of isomers), Carbamic acid [1-(imidazo[1,5-a]pyridin-3-ylmethyl)-2-oxo-2-[(2-phenylethyl)amino]ethyl]-, tricyclo[3.3.1.1³,⁷]dec-2-yl ester, and Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1³,⁷]dec-2-yl ester (mixture of isomers).

Table I below lists representative biologically significant amino acids. This includes the primary or genetically coded amino acids as well as some secondary amino acids.

TABLE I

| Representative Biologically Significant Amino Acids* | |
|---|---|
| Amino Acid | Abbreviation |
| Alanine | ALA |
| β- Alanine | β-ALA |
| Alloisoleucine | Allo-ILE |
| Allthreonine | Allo-THR |
| Arginine | ARG |
| Asparagine | ASN |
| Aspartic Acid | ASP |
| Citrulline | |
| Cystine | CYST |
| Glutamic Acid | GLU |
| Glutamine | GLN |
| Histidine | HIS |
| Homocysteine | HCY |
| Homoserine | HSE |
| Isoleucine | ILE |
| Isovaline | IVA |
| Kainate | |
| Leucine | LEU |
| Lysine | LYS |
| Methionine | MET |
| Norleucine | NLE |
| Norvaline | NVA |
| Ornithine | ORN |
| Peniculamine | |
| Phenylalanine | PHE |
| Proline | PRO |
| Quisqualate | |
| Serine | SER |
| Threonine | THR |
| Tyrosine | TYR |
| Valine | VAL |

Table II below illustrates representative compounds of the invention. Stereochemistry is not shown in Table II.

TABLE II $$R^1-A-N-C-N-C-C-Ar \atop H+ \; CH_2 \; R^3 \; \pm R^4 \atop Ar^2$$

(with R², O, R⁹, R¹², R¹³ substituents)

| R¹ | A | R² | Ar² | R⁹ | R³ | R¹² | R⁴ | R¹³ | Ar | K (CCK—B)n M |
|---|---|---|---|---|---|---|---|---|---|---|
| adamantyl | O—CO | Me | 3-methyl-4-(2-(N-methylsulfonyl)aminophenyl)pyridine | H | H | CH₂OH | H | H | Ph | 844 |
| " | O—CO | Me (Diast I) | 2-methylpyridine | H | H | CH₂OH | H | H | Ph | 1000 |
| " | O—CO | Me (Diast II) | " | H | H | CH₂OH | H | H | Ph | 1A 1990 |
| adamantyl | O—CO | Me | 3-methyl-4-(2-(N-methylsulfonyl)aminophenyl)pyridine | H | H | H | H | H | Ph | 1990 |
| " | O—CO | Me | 3-methyl-4-(2-aminophenyl)pyridine | H | H | H | H | H | Ph | 2170 |
| " | O—CO | Me | 2-methylpyridine | H | H | H | H | H | Ph | 3000 |

TABLE II-continued
$R^1-A-N-C-C-N-C-C-Ar$ structure with $R^2$, $R^9$, $R^{12}$, $R^{13}$, $R^3$, $R^4$, $CH_2-Ar^2$
| $R^1$ | A | $R^2$ | $Ar^2$ | $R^9$ | $R^3$ | $R^{12}$ | $R^4$ | $R^{13}$ | Ar | K (CCK—B)n M |
|---|---|---|---|---|---|---|---|---|---|---|
| " | O—CO | Me | 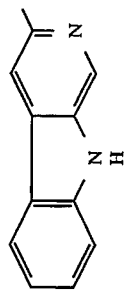 | H | H | CH₂OH | H | H | Ph | 1390 |
| " | O—CO | Me (Diast I) | 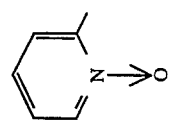 | H | H | CH₂OH | H | H | Ph | IA |
| " | O—CO | Me (Diast II) | 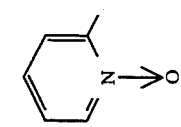 | H | H | CH₂OH | H | H | Ph | IA |
| 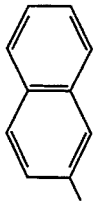 | O—CO | Me | " | H | H | H | H | H | Ph | IA |
| " | O—CO | Me | 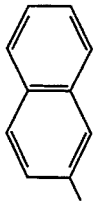 | H | H | H | H | H | Ph | 310 |
| " | O—CO | Me | " | H | H | H | H | H | Ph | 66 |

TABLE II-continued
R¹—A—N—C—C—N—C—C—Ar
       H⁺  R²  O  R⁹ R¹² R¹³
              |       |     |
              CH₂    R³    R⁴
              |
              Ar²
| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me | 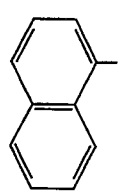 | H | H | CH₂OH | H | H | Ph | 720 |
| 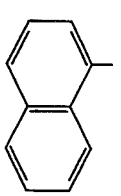 | O—CO | Me | 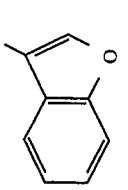 | H | H | CH₂OH | H | H | Ph | 14 |
| " | O—CO | Me | 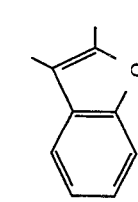 | H | H | H | H | H | Ph | 990 |
| " | O—CO | Me | " | H | H | CH₂OH | H | H | Ph | 360 |
| " | O—CO | Me | 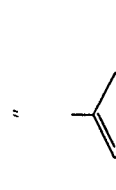 | H | H | H | H | H | Ph | 1280 |
| " | O—CO | Me | " | H | H | CH₂OH | H | H | Ph | 14 |
| 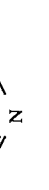 | O—CO | Me | 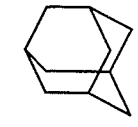 | H | H | H | H | H | Ph | $3 \times 10^{-6}$ |

TABLE II-continued $$R^1-A-N(H+)-C(R^2)(CH_2Ar^2)-C(=O)-N(R^9)-C(R^{12})(R^3)-C(R^{13})(R^4)-Ar$$

| R¹ | A | R² | Ar² | R⁹ | R³ | R¹² | R⁴ | R¹³ | Ar | K(CCK—B)n M |
|---|---|---|---|---|---|---|---|---|---|---|
| " | O—CO | Me (Diast II) | 2-methylpyridine N-oxide | H | H | H | CH₂OH | H | Ph | — |
| " | O—CO | Me (Diast I) | 3-methylpyridine | H | H | CH₂OH | H | H | Ph | 7 × 10⁻⁷ |
| " | O—CO | Me (Diast II) | " | H | H | CH₂OH | H | H | Ph | IA |
| " | O—CO | Me | 3-methylpyridine | H | H | CH₂OCO₂i-Bu | H | H | Ph | 3000 |
| " | O—CO | Me | pyridine | H | H | H | H | H | Ph | IA |
| adamantyl | O—CO | Me | 2-methylpyridine N-oxide | H | H | CH₂OCO₂i-Bu | H | H | Ph | IA |
| " | O—CO | Me (Diast I) | 2-methylquinoline | H | H | CH₂OH | H | H | Ph | 410 |

TABLE II-continued $$R^1-A-N-C-C-N-C-Ar$$
$$\phantom{R^1-A-}H\phantom{-N-}\overset{R^2}{\underset{CH_2}{|}}\phantom{-C-}\overset{O}{\phantom{|}}\phantom{-C-}\overset{R^9}{\underset{|}{|}}\overset{R^{12}}{\underset{R^3}{|}}\overset{R^{13}}{\underset{R^4}{|}}$$
$$\phantom{R^1-A-N-}Ar^2$$

| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me | " | H | H | H | H | H | Ph | 400 |
| 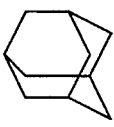 | O—CO | Me | " | H | H | H | H | H | Ph | — |
| " | O—CO | Me | 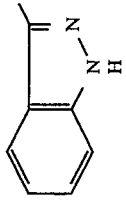 | H | H | H | H | H | Ph | 100 |
| " | O—CO | Me | " | H | H | CH₂OH | H | H | Ph | 69 |
| " | O—CO | Me | 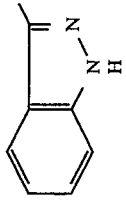 | H | H | H | H | H | Ph | — |
| " | O—CO | Me | 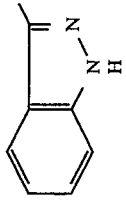 | H | H | CH₂OH | H | H | Ph | 129 |
| " | O—CO | Me | " | H | H | H | H | H | Ph | 262 |
| 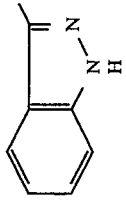 | O—CO | Me | 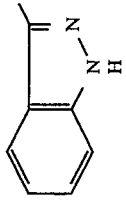 | H | H | H | H | H | Ph | 304 |

TABLE II-continued $$R^1-A-N-\overset{R^2}{\underset{H^+}{C}}-\overset{O}{\underset{CH_2}{C}}-N-\overset{R^{12}}{\underset{R^3}{C}}-\overset{R^{13}}{\underset{R^4}{C}}-Ar$$
$$Ar^2$$

| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me | 2-methylquinoline | H | H | CH₂OH | H | H | Ph | 402 |
| " | O—CO | Me | methyl-pyridine-phenyl-NH | H | H | H | H | H | Ph | 396 |
| " | O—CO | Me | " | H | H | CH₂OH | H | H | Ph | 1400 |
| " | O—CO | Me | 2-benzimidazole | H | H | CH₂OH | H | H | Ph | — |
| 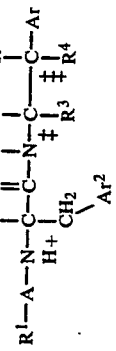 | O—CO | Me | " | H | H | H | H | H | Ph | — |
| " | O—CO | Me | benzothiophene | H | H | CH₂OH | H | H | Ph | — |
| " | O—CO | Me | " | H | H | H | H | H | Ph | 760 |
| " | O—CO | Me | " | H | H | CH₂OH | H | H | Ph | 455 |

TABLE II-continued
$$R^1-A-N-C-C-N-C-C-Ar$$
with $R^2$, O, $R^9$, $R^{12}$, $R^{13}$, $R^3$, $R^4$ substituents, H+ CH₂ Ar²
| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me | 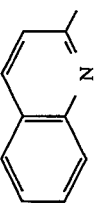 | H | H | H | H | NHCOCH₂CH₂COOH | Ph | 290 |
| " | O—CO | Me | 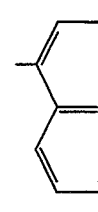 | H | H | H | H | NHCOCH₂CH₂COOH | Ph | 88 |
| 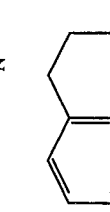 | O—CO | Me | 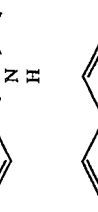 | H | H | H | H | NHCOCH₂CH₂COOH | Ph | 690 |
| " | O—CO | Me | 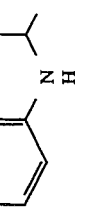 | H | H | H | H | NHCOCH₂CH₂COOH | Ph | 3000 |
| " | O—CO | Me | 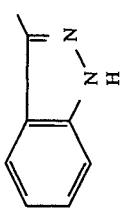 | H | H | H | H | NHCOCH₂CH₂COOH | Ph | 96 |
| " | O—CO | Me (Diast I) | " | H | H | H | H | 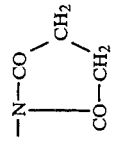 | Ph | IA |

TABLE II-continued $$R^1-A-\underset{H^+}{N}-\underset{\underset{Ar^2}{CH_2}}{\overset{R^2}{\underset{|}{C}}}-\overset{O}{\overset{\|}{C}}-\underset{R^3}{\overset{R^9}{\underset{|}{N}}}-\overset{R^{12}}{\underset{R^{12}}{\overset{|}{C}}}-\overset{R^{13}}{\underset{R^4}{\overset{|}{C}}}-Ar$$

| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me (Diast II) | | H | H | H | H | " | Ph | |
| adamantyl | O—CO | Me | pyrrole (2,3-dimethyl) | H | H | H | H | H | Ph | 220 |
| " | O—CO | Me | " | H | H | CH₂OH | H | OH | Ph | IA |
| " | O—CO | Me | 2-(aminomethyl)pyridine | H | H | CH₂OH | H | H | Ph | 3000 |
| " | O—CO | Me | " | H | H | H | H | OH | Ph | 930 |
| " | O—CO | Me | 3-methylpyridine N-oxide | H | H | CH₂OH | H | H | Ph | 750 |
| " | O—CO | Me | 3-methylpyridine N-oxide | H | H | H | H | H | Ph | IA |
| adamantyl | O—CO | Me (Diast I) | " | H | H | CH₂OH | H | H | Ph | IA |
| " | O—CO | Me (Diast II) | " | H | H | CH₂OH | H | H | Ph | IA |

TABLE II-continued
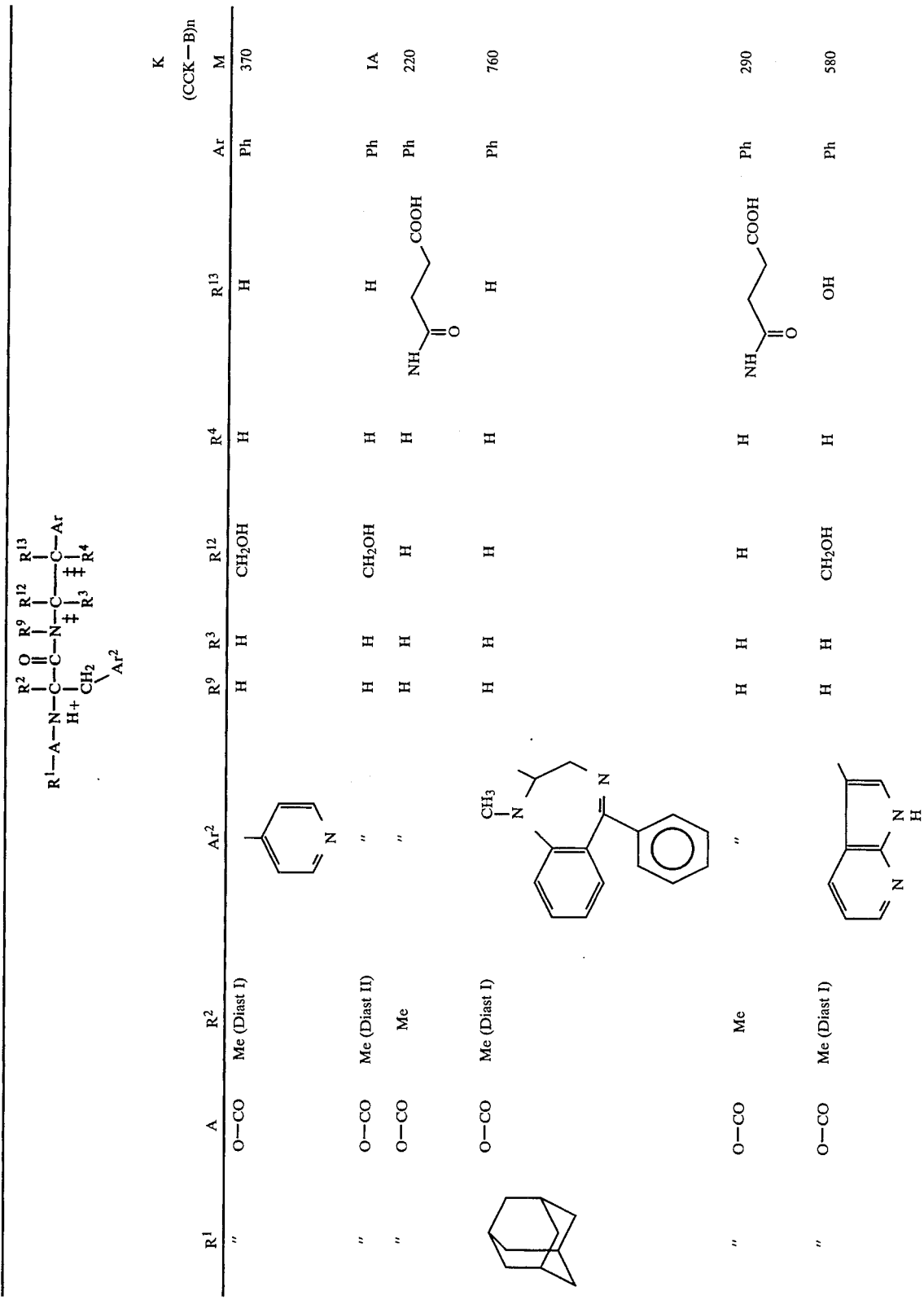
| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me (Diast I) | 4-pyridyl | H | H | CH₂OH | H | H | Ph | 370 |
| " | O—CO | Me (Diast II) | " | H | H | CH₂OH | H | H | Ph | IA |
| " | O—CO | Me | " | H | H | H | H | NHC(O)CH₂CH₂COOH | Ph | 220 |
| adamantyl | O—CO | Me (Diast I) | N-methyl-imine | H | H | H | H | H | Ph | 760 |
| " | O—CO | Me | " | H | H | H | H | NHC(O)CH₂CH₂COOH | Ph | 290 |
| " | O—CO | Me (Diast I) | 3-methyl-7-azaindole | H | H | CH₂OH | H | OH | Ph | 580 |

TABLE II-continued
$R^1-A-N(H+)-C(R^2)(CH_2Ar^2)-C(O)-N(R^9)-C(R^3)(R^{12})-C(R^{13})(R^4)-Ar$
| R¹ | A | R² | Ar² | R⁹ | R³ | R¹² | R⁴ | R¹³ | Ar | K (CCK—B)n M |
|---|---|---|---|---|---|---|---|---|---|---|
| " | O—CO | Me (Diast II) | 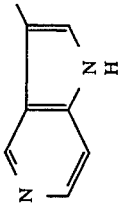 | H | H | CH₂OH | H | OH | Ph | 43 |
| " | O—CO | Me (Diast I) | 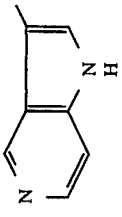 | H | H | CH₂OH | H | OH | Ph | IA |
|  | O—CO | Me (Diast II) | " | H | H | CH₂OH | H | OH | Ph | 2300 |
IA = Inactive in respect to this binding assay.

The compounds include solvates and hydrates and pharmaceutically acceptable salts of the compounds of formula I.

The compounds of the present invention can have multiple chiral centers including those designated in the above formula I by a +, ‡, ‡, depending on their structures. For example, when $R^3$ taken with $R^{12}$ and $R^4$ taken with $R^{13}$ form double bonds to these carbon atoms they are no longer chiral. In addition, centers of asymmetry may exist on substituents $R^1$, $R^9$, $R^3$, $R^4$, Ar, and/or $Ar^2$. In particular, the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional method well known in the art such as conversion to a salt with an optically active compound, followed by separation by chromatography or recrystallization and reconversion to the nonsalt form.

Pharmaceutically acceptable salts are: benzathine, chloroprocaine, choline, diethanolamine, ethylenediamine, meglumine, procaine, aluminum, calcium, lithium, magnesium, potassium, sodium, and zinc.

The compounds of the present invention can be formed by coupling individual substituted α-amino acids by methods well known in the art. (See, for example, standard synthetic methods discussed in the multi-volume treatise "The Peptides, Analysis, Synthesis, Biology," by Gross and Meienhofer, Academic Press, New York). The individual substituted alpha amino acid starting materials are generally known or, if not known, may be synthesized and, if desired, resolved by methods within the skill of the art. (Synthesis of racemic [DL~]-α-methyl tryptophan methylester—see M. F. Brana, et al, *J. Heterocyclic Chem.* 17:829, 1980).

The following schemes illustrate methods for preparing compounds of the invention.

Scheme I below illustrates preparative steps in the process for making compounds of the instant invention. As shown, the Schiff's base (1) prepared by standard literature procedures is deprotonated using lithium di-isopropyl amide and this carbanion is reacted with the aryl methyl halide 2. Following this substitution, the Schiff's base is hydrolyzed with aqueous acid to the free amine 3. This amine 3 is reacted with 2-adamantyl chloroformate in the presence of triethylamine to yield the urethane. The ester moiety was then saponified using hydroxide to the carboxylic acid 4. An active ester of this acid was prepared by treatment with N,N'-dicyclohexyl-carbodiimide and pentafluorophenol (or 1-hydroxybenzotriazole) which underwent further reaction with the appropriate amine to give the amides 5a–h, Examples 1–12.

SCHEME I

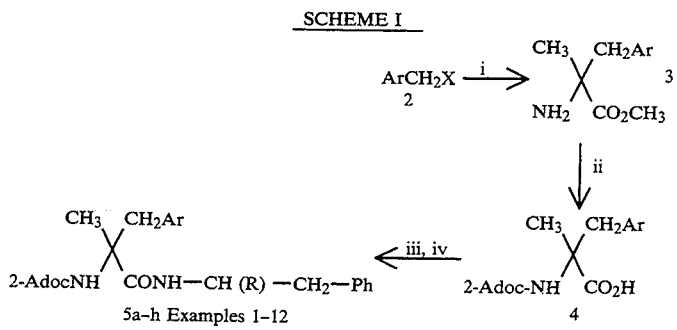

Ar is
a) 1-Naphthyl,
b) 2-Naphthyl,
c) 3-Benzothienyl,
d) 2-1-Boc-benzimidazolyl),
e) 3(2-Bromobenzofuranyl),
f) 2-Benzimidazolyl,
g) 3-Benzofuranyl, or
h) imidazolyl;
X is Br or Cl;
Y is hydrogen or 4-Cl;
i; LDA or LHMDSA-THF:H3O+:OH−
ii; 2-AdocCl-THF-Et3N:OH−
iii; DCCI or WSDCCI; PfpOH or HOBt; PhCh2CH(R)NH2-EtOAc
iv; HCO2NH4—10% Pd/C—MeOH—cC6H8 when A is e) above.

PREPARATIVE EXAMPLES (SCHEME I)

Alkylation Procedure

A solution of Y—PhCH=N—CH(CH3)CO2CH3 (50 mmol) in THF (150 mL) was added to a stirred solution of LDA (55 mmol) in THF at −78° C. The resulting yellow anion was further treated with a solution of the aralkyl halide (ARCH2) (50 mmol) and the resulting mixture allowed to stir overnight. Following removal of volatile materials the viscous residue was treated with 1N HCl solution (100 mmol) and stirred rapidly for 1 to 2 hours. Benzaldehyde was removed by extraction with ether and the aqueous phase made alkaline using 10% aqueous sodium bicarbonate solution. The amino ester

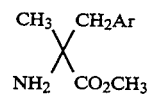

was extracted into ether, the organic phase dried (MgSO4) and evaporated, leaving the crude product which was purified as indicated.

α-Methyl-DL-3(1-naphthyl)alanine methyl ester (3a)

Using 1-bromomethylnaphthalene, the product was isolated in 60% yield as a pale yellow, crystalline solid from ether. NMR (CDCl3) δ 1.47 (3H, s), 1.6 (2H, s), 3.46 (2H, dd), 3.58 (3H, s), 7.31–7.52 (4H, m), 7.75 (2H, dd), 8.13 (1H, d).

α-Methyl-DL-3(2-naphthyl)alanine methyl ester) (3b)

Starting from 2-bromomethylnaphthalene as alkyl halide, the product was isolated in 90% yield as a pale yellow solid from ether. NMR (CDCl₃) δ 1.41 (3H, s), 1.6 (2H, s), 3.1 (2H, dd), 3.7 (3H, s), 7.24–7.88 (7H, m).

α-Methyl-DL-3(3-benzothienyl)alanine methyl ester (3c)

Using 3-chloromethylbenzothiophene as alkylating agent, the product was isolated in 78% crude yield as a light yellow oil. Chromatography (silica gel, 4% MeOH—CH₂Cl₂) gave 67% overall yield of a colorless oil. NMR (CDCl₃) δ 1.45 (3H, s), 1.65 (2H, s), 3.24 (2H, dd), 3.63 (3H, s), 7.2 (1H, s), 7.29–7.4 (2H, m), 7.81–7.85 (2H, m).

α-Methyl-DL-3(2-bromo-3-benzofuranyl)alanine methyl ester (3e)

Starting from 2-bromo-3-bromomethylbenzofuran, the product was isolated in 43% crude yield and 23% overall yield of a pale yellow oil following chromatography as above. NMR (CDCl₃ δ 1.46 (3H, s), 1.81 (2H, s), 3.02 (2H, dd), 3.67 (3H, s), 7.18–7.27 (2H, m), 7.39 (1H, m), 7.53 (1H, m).

α-Methyl-DL-(2-benzimidazolyl)alanine methyl ester (3f)

1-Boc-2-chloromethylbenzimidazole was used as alkylating agent and provided an 83% crude yield of a viscous oil, used without further purification. IR (film); 1733 cm⁻¹; NMR (CDCl₃) δ 1.41 (3H, s), 3.28 (2H, s), 3.77 (3H, s), 7.26–7.34 (3H, m), 7.54–7.57 (2H, m).

Acylation-saponification procedure

A solution of the desired amino ester (2 mmol) in dry THF (20 mL) was treated with 2-AdocCl (2.2 mmol) followed by the dropwise addition of triethylamine (2.2 mmol). The mixture was stirred for 4 hours at room temperature. Volatile material was removed under vacuum and the residue partitioned between ethyl acetate and water. The organic layer was washed with dilute aqueous citric acid solution followed by dilute sodium bicarbonate solution then saline solution. After drying the solution (MgSO₄), the solvent was removed, leaving the crude protected ester. This was dissolved in dioxan or methanol (15 mL) and a 1N solution of lithium hydroxide added (10 mmol). When TLC revealed completion of the reaction, the solvent was removed and the residue suspended between ethyl acetate and dilute aqueous citric acid solution. The organic layer was removed, washed once with water, dried, and evaporated to give the product.

2-Adoc-α-methyl-DL-3(1-naphthyl) alanine (4a)

79% crude overall yield from α-methyl-DL-3(1-naphthyl)alanine methyl ester, of a viscous resin. Not purified further before use. NMR (CDCl₃) δ 1.52–2.1 (17H, m), 3.81 (2H, s), 4.88 (1H, s), 5.19 (1H, s), 7.25–7.46 (5H, m), 7.75–7.85 (2H, m), 8.12 (1H, m).

2-Adoc-α-methyl-DL-3(2-naphthyl)alanine (4b)

Starting from α-methyl-DL-3(2-naphthyl alanine methyl ester, this was isolated as a white powder from ether, 86%. NMR (CDCl₃) δ 1.53–2.13 (17H, m), 3.48 (2H, dd), 4.84 (1H, s), 6.58 (1H, s), 7.24–7.79 (7H, m).

2-Adoc-α-methyl-DL-3(benzothienyl) alanine (4c)

Starting from α-methyl-DL-3(3-benzothionyl)alanine methyl ester, this was isolated as a white powder, 77%. NMR (CDCl₃) δ 1.44–2.0 (17H, m), 3.51 (2H, dd), 4.74 (1H, s), 6.63 (1H, s), 7.23–7.36 (3H, m), 7.77–7.86 (2H, m).

2-Adoc-α-methyl-DL-3(2-bromo-3-benzofuranyl) alanine (4e)

This was isolated as a pale pink foam, of uncertain stability, in 74% yield. Used without purification. NMR (CDCl₃) δ 1.49–2.08 (17H, m), 3.41 (2H, dd), 4.91 (1H, s), 5.24 (1H, s), 7.15–7.36 (2H, m), 7.4–7.48 (2H, m).

2-Adoc-α-methyl-DL-3(2-benzimidazolyl)alanine (4d)

Isolated in 35% yield as a white powder, mp 222°–232° C., from -methyl-DL-(2-benzimidazolyl)-alanine methyl ester. NMR (DMSO-d₆) δ 1.46 (3H, s), 1.67–1.97 (14H, m), 3.28 (1H, d, J=14Hz), 3.42–3.51 (1H, m), 4.64 (1H, s), 7.01–7.1 (3H, m), 7.45 (2H, s).

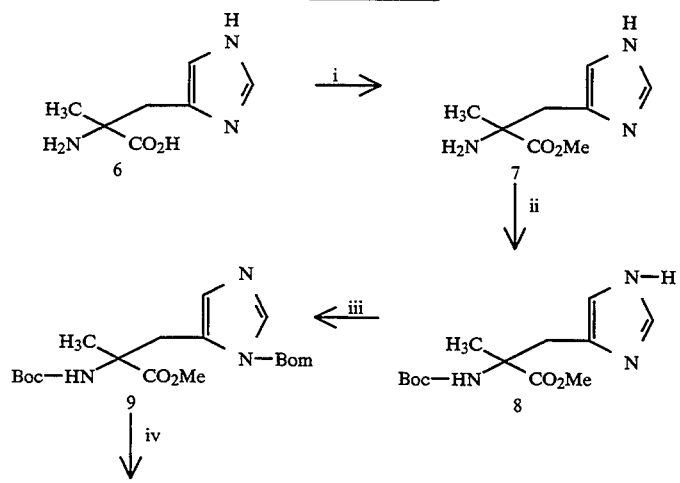

SCHEME II

SCHEME II

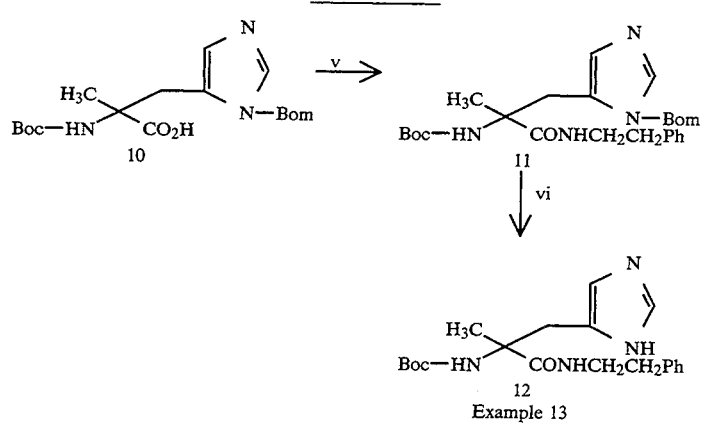

Example 13 i; SOCl₂—MeOH
ii; Et₃N—MeOH—Boc₂O
iii; BzOCH₂Cl—CH₂Cl₂
iv; MeOH—LiOH.H₂O
v; PhCH₂CH₂NH₂—DCC—PfpOH
vi; H₂—Pd(OH)₂—EtOH Scheme III below illustrates synthetic steps towards some phenolic derivatives of the instant invention. The phenol 13 is treated with benzylbromide, NaOH, and tetrabutyl ammonium bromide, affording the ether 14, the aldehyde of which is reduced to the primary alcohol 15 using NaBH₄. The bromomethylene compound 16 is prepared from the primary alcohol by treatment of 15 with Ph₃P, Br₂, and Et₃N. This is then reacted with lithiomethyl-N-benzalalaninate, and the imine hydrolyzed with aqueous acid to the amine 17, which is coupled with 2-adamantyl chloroformate to give the urethane 18. Ester hydrolysis of 18 with LiOH to 19 followed by condensation with 2-phenethylamine gave 20 upon which gave the product 21 (Example 14) upon hydrogenation of the ether over Pd/C.

SCHEME III

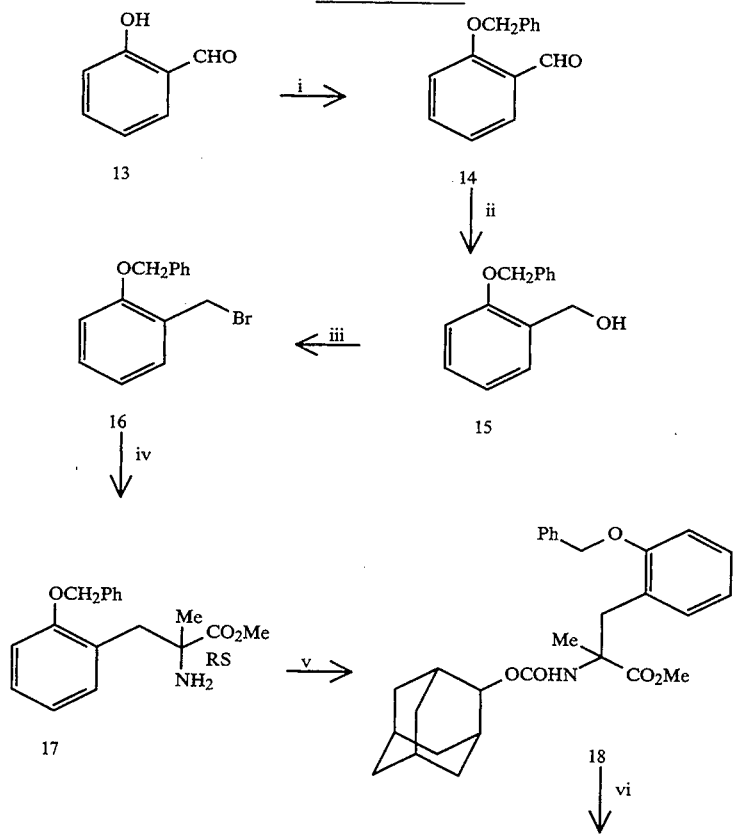

SCHEME III

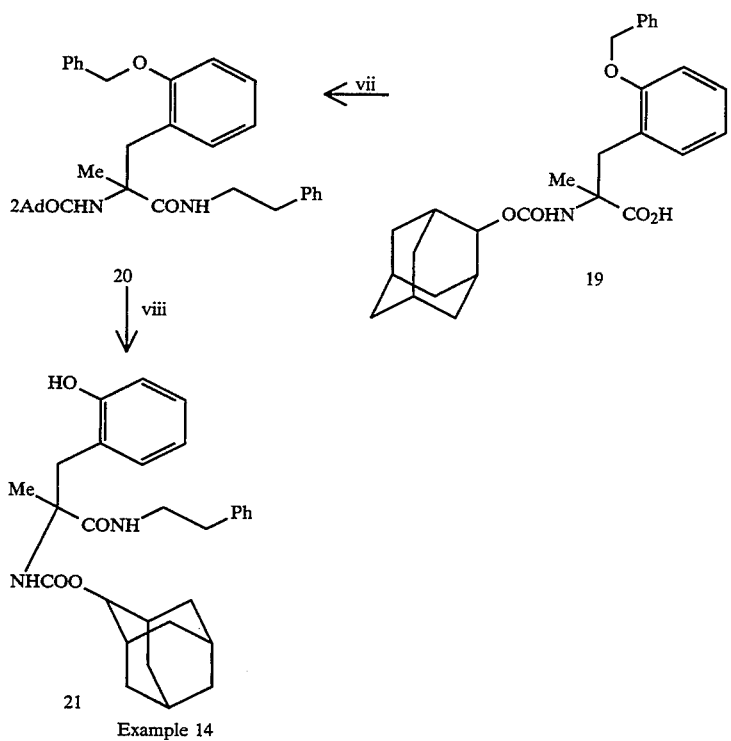

Example 14 i; PhCH₂Br, NaOH, nBu₄N⁺Br⁻
ii; NaBH₄
iii; Ph₃P·Br₂, Et₃N iv; CH₃CHCO₂Me , LDA, then H₃O⁺
       |
       N=CHC₆H₄p-Cl v; 2AdOCCl, Et₃N
vi; LiOH, H₂O vii; HOBT, DCC, H₂N~~Ph viii; Pd(OH)₂/C₂H₅OH Scheme IV shows how aniline derivatives are synthesized in an exactly analogous way to that described in Scheme III, the primary alcohol 22 was converted to the methyl bromide 23 from which the amine-ester 4 was prepared. Reaction with 2-adamantyl chloroformate gave 25, hydrolysis of the ester to 26 and condensation with 2-phenethylamine gave 27. Reduction of the nitro group was effected using 10% palladium on carbon under an atmosphere of hydrogen to give the product 28 (Example 15).

SCHEME IV

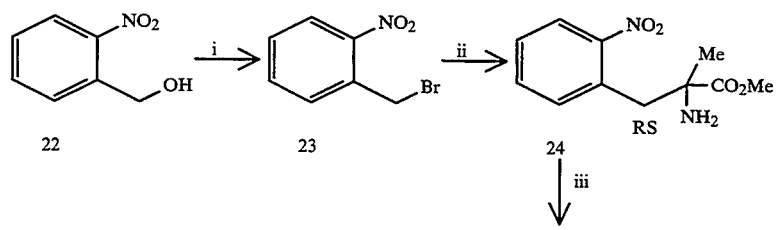

SCHEME IV

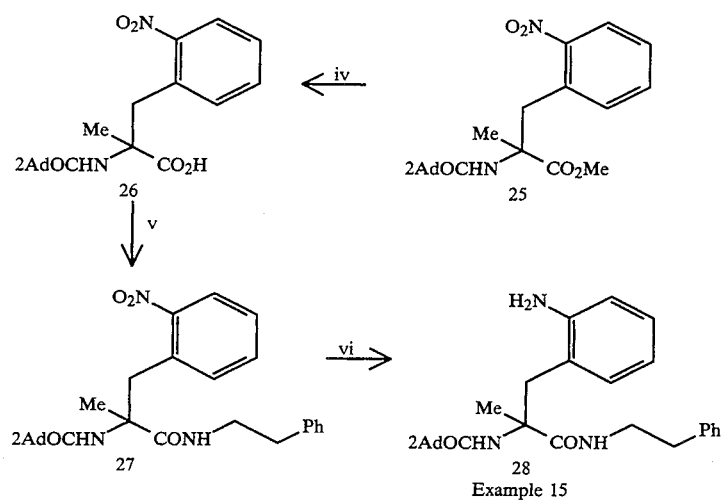

i; Ph₃PBr₂ ii; CH₃CHCO₂Me, LDA, then H₃O⁺
   |
   N=CHC₆H₄p-Cl iii; 2Adoc-Cl + Et₃N
iv; LiOH, H₂O v; HOBT, DCC, H₂N–CH₂CH₂–Ph vi; 10% Pd/C, H₂, EtOH Scheme V illustrates the synthesis of compound exemplified by Example 16.

Methyl N-benzalalaninate was treated with sodium dimesyl in dimethyl sulphoxide solution. To this, a solution of 2-chloromethyl-2,3-dihydro-1-methyl-5-phenyl-1H-1,4-benzodiazepine 29 in a dimethyl sulphoxide-THF mixture was added. This gave after work-up and purification the β-(2,3-dihydro-1-methyl-5-phenyl-1H-1,4-benzodiazepin-2-yl)-α-methyl alanine methyl ester 30 in 37% yield as a mixture of 2 diastereoisomers. Treatment of the free amine 30 with 2-adamantyl chloroformate gave the urethane 31 and the carboxylic acid ester was saponified with lithium hydroxide and the appropriate amide prepared via the active pentafluorophenyl ester and the corresponding amine, as seen in earlier schemes, yielding 33, exemplified by Example 16. The resultant 2 diastereoisomers were separable by flash chromatography.

SCHEME V

Scheme V below illustrates a process for preparing compounds of the instant invention as exemplified by Example 16.

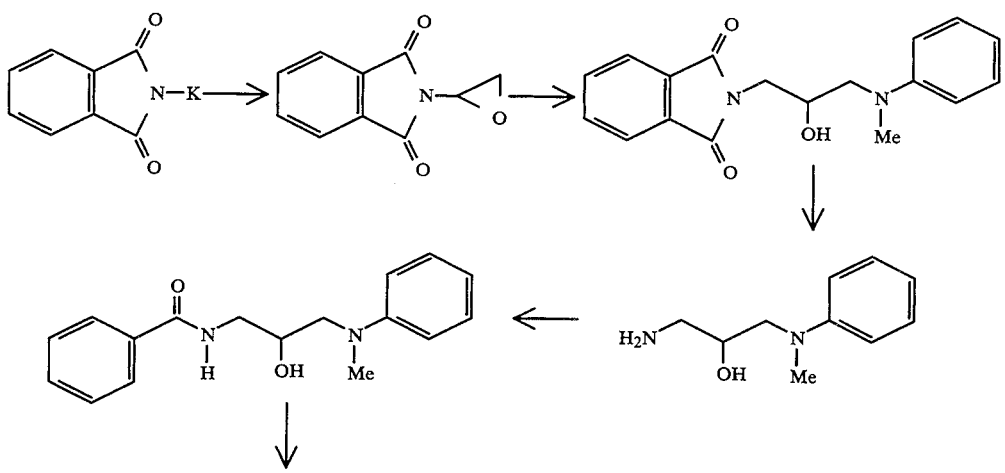

-continued

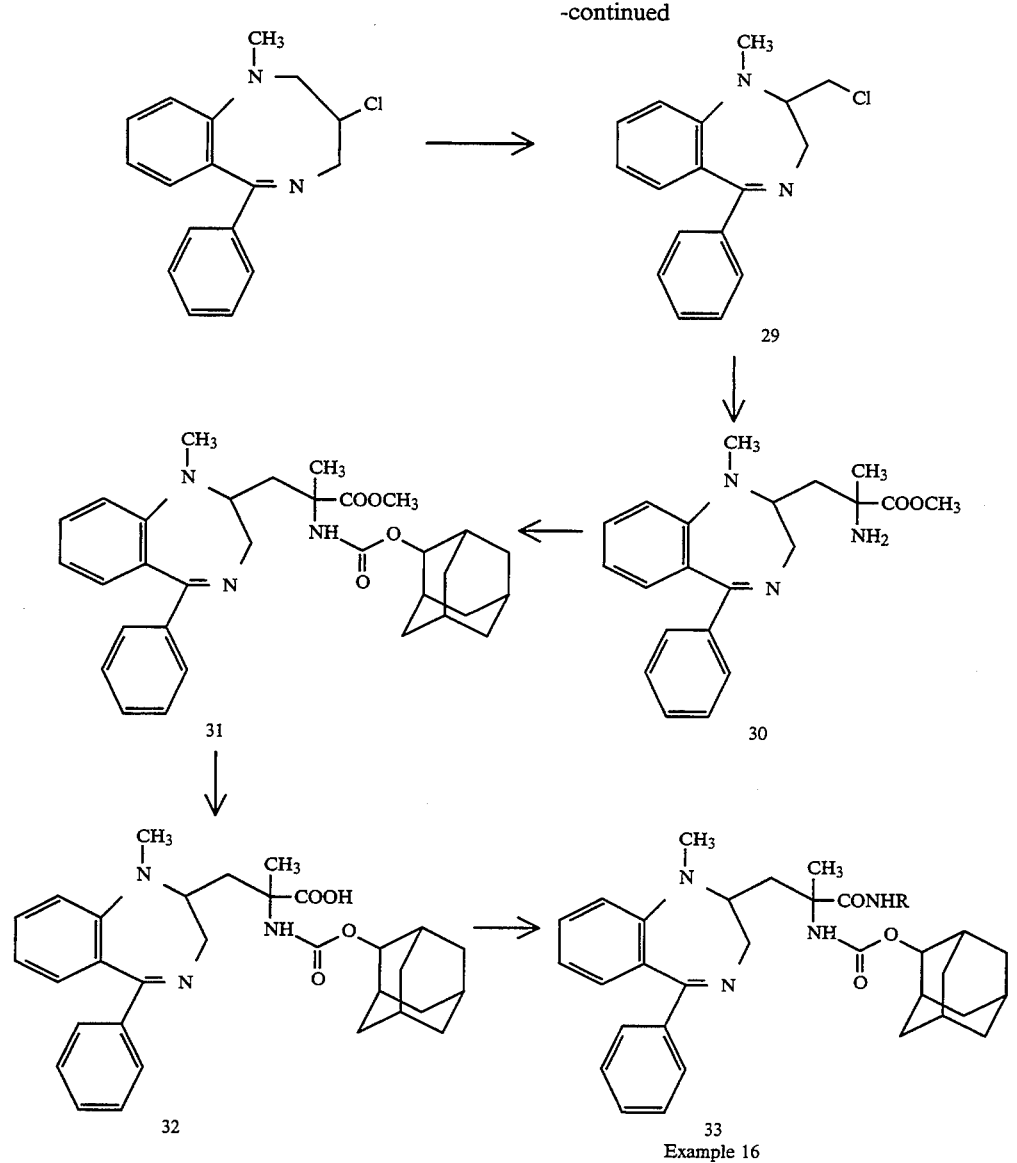

Example 16

Scheme VI below shows chloromethylpyridine-1-oxide 34 as a solution in dimethylsulphoxide was treated with the carbanion formed by treating methyl N-benzalalaninate with potassium tert-butoxide in tetrahydrofuran to give the corresponding imine Schiff's base, this imine was hydrolyzed to the amine hydrochloride salt with methanolic HCl, 35. This α-methyl-β-(pyridyl-1-oxide)-DL alanine methyl ester dihydrochloride 35 was then treated with 2-adamantyl chloroformate in the presence of base to give the urethane 36. The ester group was hydrolyzed as before, using lithium hydroxide to the end 37. The appropriate amides 38 were prepared by treatment of the active esters such as the pentafluoro phenyl ester or that from N,N-carbonyldiimidazole, or via the mixed anhydride formed by treatment of the acid with isobutyl chloroformate and N-methyl morpholine, with the corresponding amines. The pyridyl-1-oxide moiety was reduced using 10% palladium on carbon and an atmosphere of hydrogen at 30 bar pressure to give, for example, the N-[(2-adamantyloxy)carbonyl]-α-methyl-β-(2-pyridyl)-DL-alanine-2-phenethylamide, Example 18.

SCHEME VI

Scheme VI below illustrates preparative steps in the process for making compounds of the instant invention as exemplified by Examples 17–29.

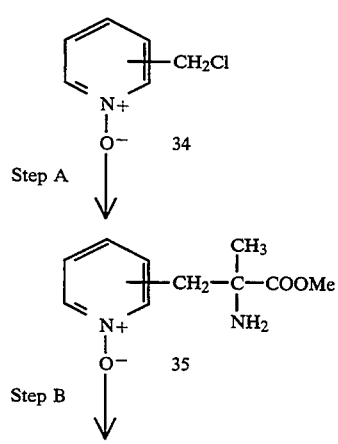

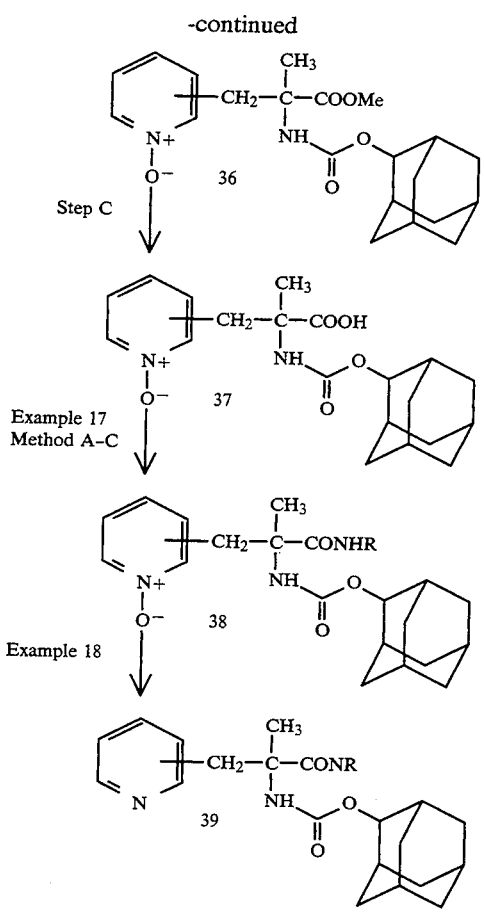

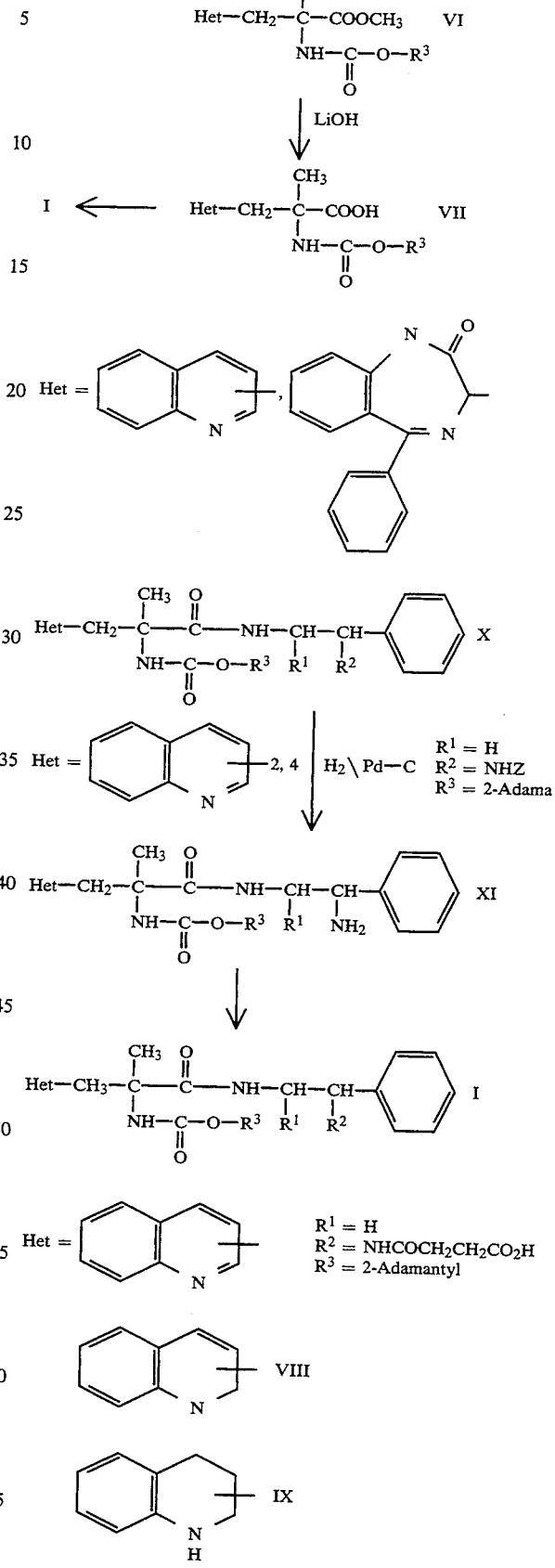

Scheme VII shows a typical sequence similar to that illustrated in Scheme V. Reaction of heteroarylmethyl halides II with the carbanion derived from methyl N-benzalalaninate III gives, upon acidic hydrolysis of the imine, the amine IV, this when treated with an appropriate chloroformate V yields the urethane—ester VI. Hydrolysis of the ester with lithium hydroxide gave the carboxylic acid VII, which may be converted to give an appropriate amide I by reaction of an active ester derivative (such as pentafluoro phenyl ester) with the corresponding amine. Hydrogenation of compound X gave a mixture of amines XI, XI, and VIII, which were acylated to various $R^2$ groups.

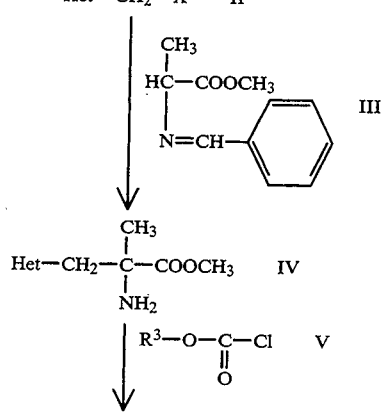

Scheme VIII shows one route to racemic N-[[(2-adamantyloxy)carbonyl]-3-(1H-indazole-3-yl)-2-methylalanine. Here a suspension of sodium hydride and methyl N-benzalalaninate 2 in DMSO was treated with a solution of 3-dimethylaminomethyl-indazolomethiodide 1 in DMSO. This gave the Schiff's base which was hydrolyzed using aqueous hydrochloric acid, the hydrochloride salt yielded the free amine 3 on treatment with potassium carbonate. This free amine 3 yielded the di-urethane on treatment with 2-adamantyl chloroformate in 4 in the presence of triethylamine. Treatment of 5 with lithium hydroxide in aqueous 1,4-dioxan gave 6 as an amorphous solid.

SCHEME VIII

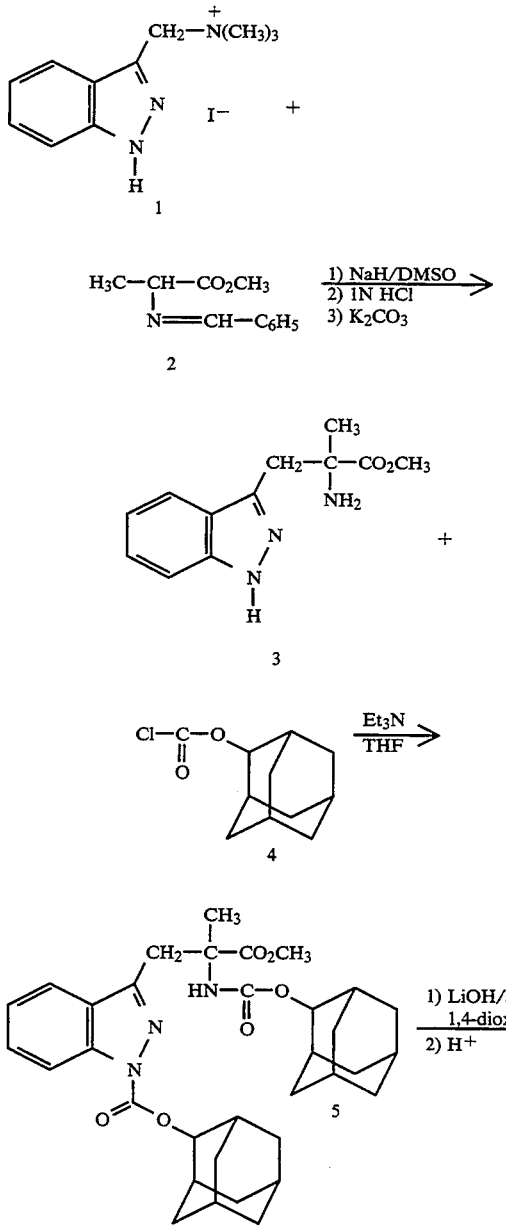

-continued
SCHEME VIII

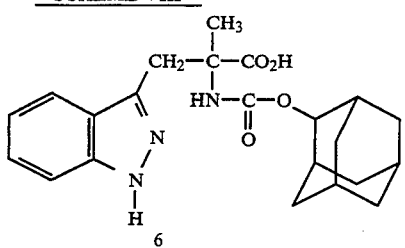

Scheme IX shows another route to compound 6. A mixture of methyl-3-indazole carboxylate 7 and sodium hydride in THF was treated with p-toluenesulphonyli chloride to give the N-tosyl protected indazole 8. Reduction of the ester 8 with Red-Al (sodium dihydrobis(2-methoxyethoxy)aluminate) gave the primary alcohol 9, which on treatment with thionyl chloride gave the methyl chloride 10. The chloromethyl derivative 10 was treated with the carbanion derived from treating methyl N-benzalalanate with sodium hydride in DMSO and the imine hydrolyzed with dilute hydrochloric acid. Treatment of the resultant HCl salt with potassium carbonate yielded the free amine 11. Reaction of 11 with 2-adamantyl chloroformate 4 in the presence of triethylamine gave the expected urethane 12. Treatment of 12 with potassium hydroxide in aqueous dioxan gave the required intermediate 6.

SCHEME IX

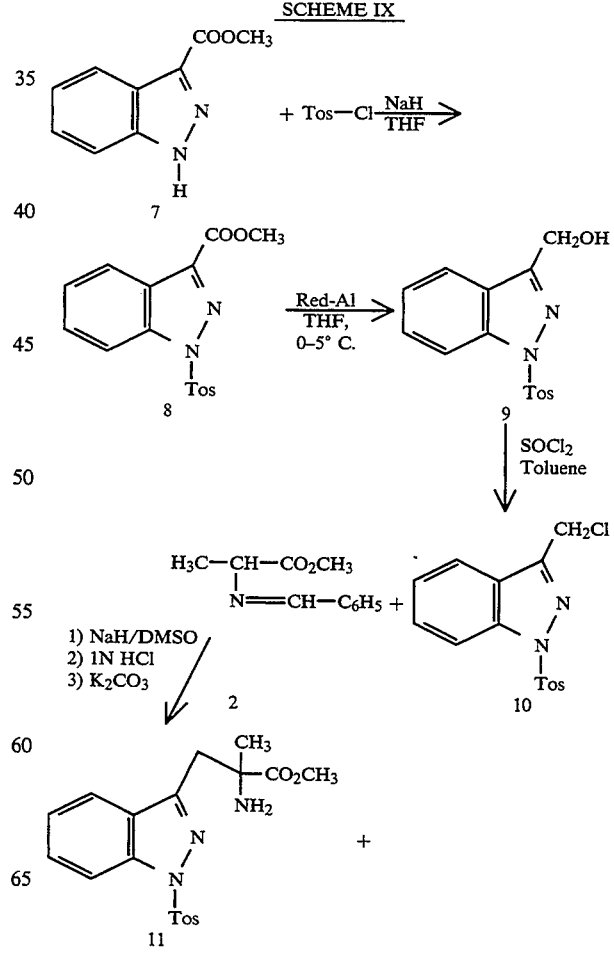

-continued
SCHEME IX

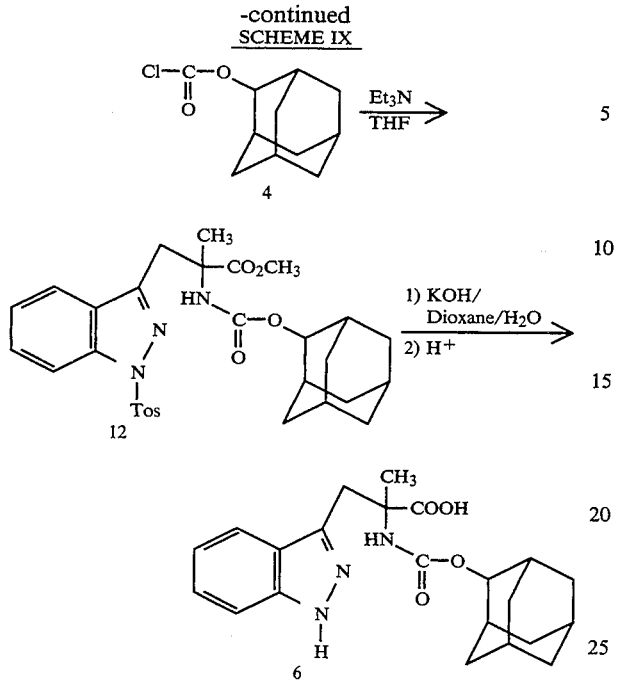

-continued
SCHEME X

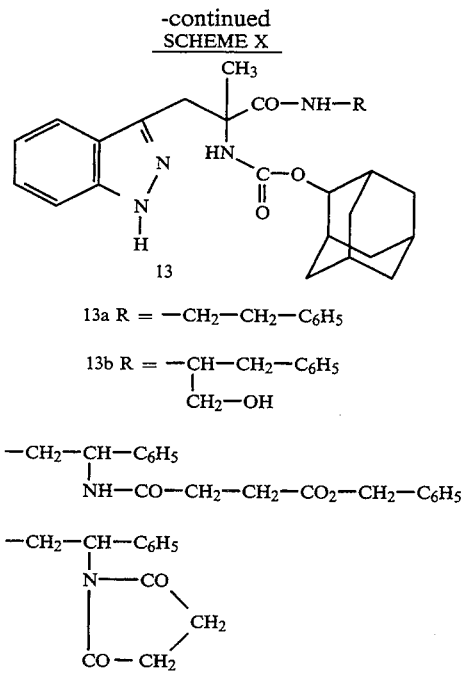

13a R = —CH$_2$—CH$_2$—C$_6$H$_5$

13b R = —CH—CH$_2$—C$_6$H$_5$
            |
            CH$_2$—OH

13c R = —CH$_2$—CH—C$_6$H$_5$
                    |
                    NH—CO—CH$_2$—CH$_2$—CO$_2$—CH$_2$—C$_6$H$_5$

13d R = —CH$_2$—CH—C$_6$H$_5$
                   |
                   N——CO
                   |    \
                   |     CH$_2$
                   |    /
                   CO—CH$_2$

Scheme X shows the synthesis of several amides 13a–c derived from 6 via the active ester of the carboxylic acid group in 6 and the appropriate amine. The benzyl ester 13c was converted to the acid 14 by hydrogenation using Pearlman's catalyst in ethanol (Scheme XI).

SCHEME X

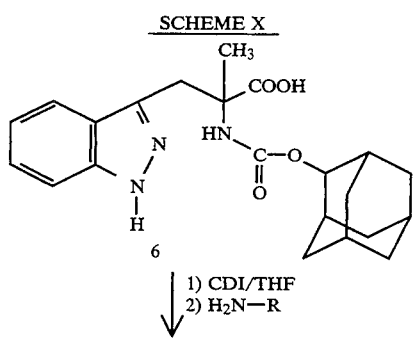

SCHEME XI

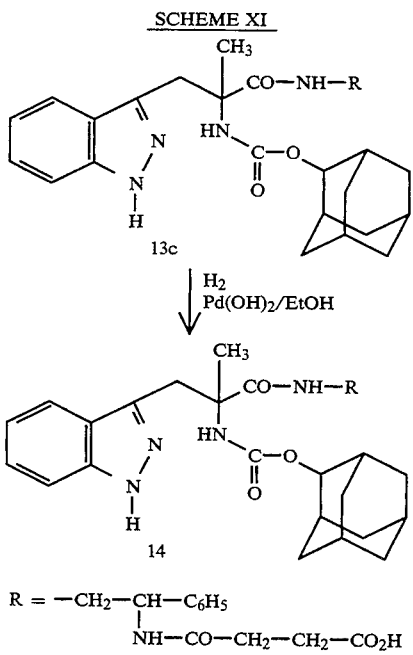

R = —CH$_2$—CH—C$_6$H$_5$
           |
           NH—CO—CH$_2$—CH$_2$—CO$_2$H

SCHEME XII
(See Example 58)

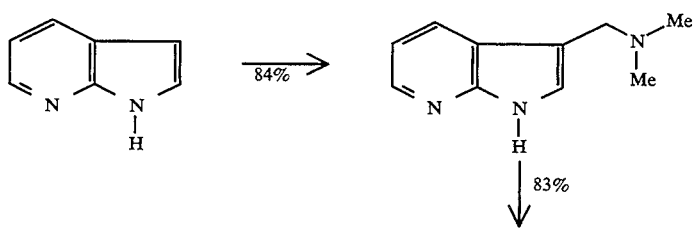

-continued
SCHEME XII
(See Example 58)
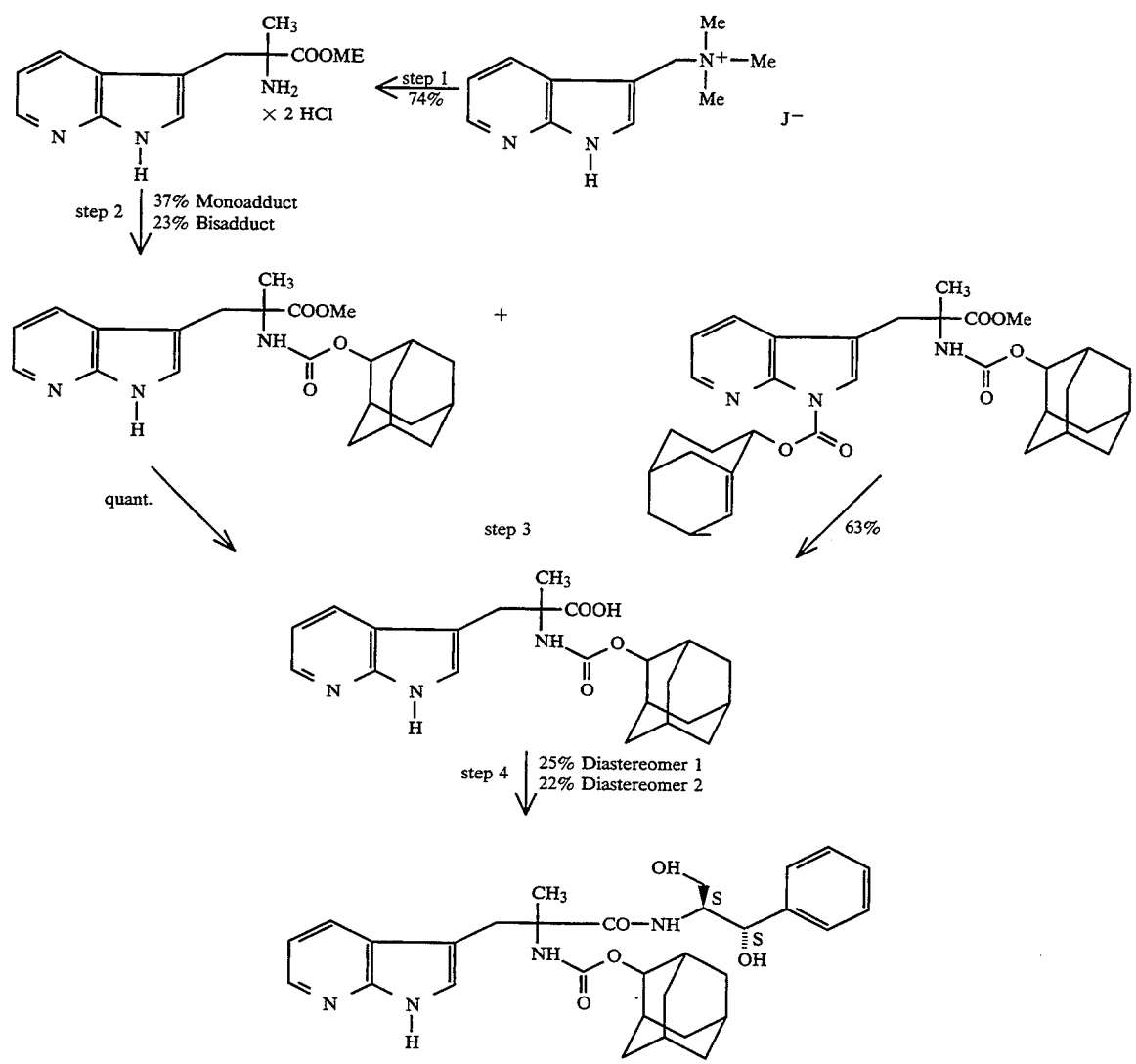
SCHEME XIII
(See Example 59)
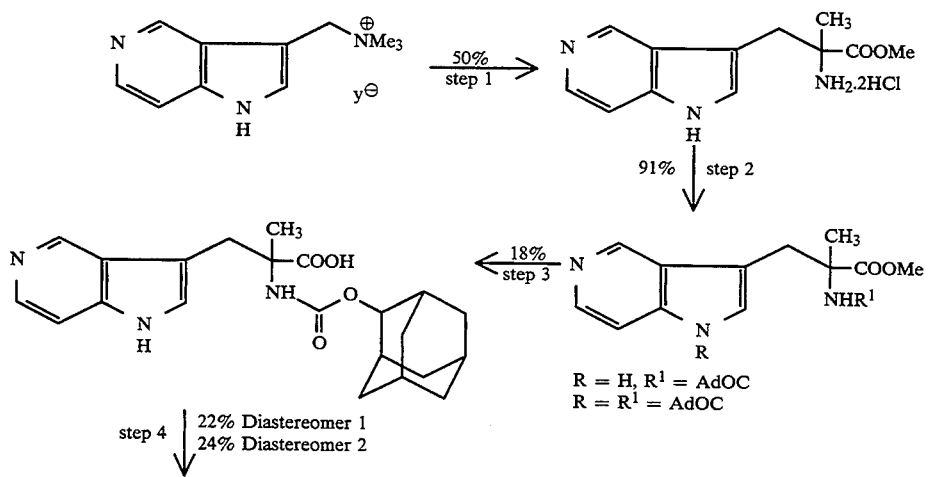

SCHEME XIII
(See Example 59)

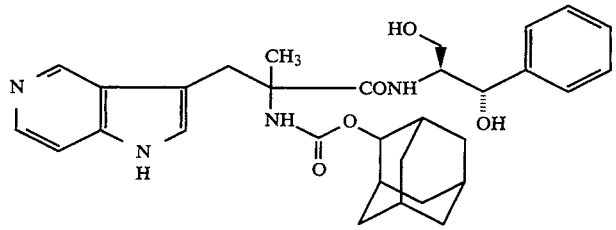

The present invention is also concerned with compounds of the formula I and processes for the preparation thereof (see Scheme XIV)

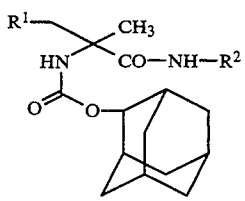

wherein $R^1$ is a group of the formula

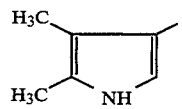

and $R^2$ is i) $-CH_2-CH_2-C_6H_5$ ii) $-CH-CH-C_6H_5$
     $\phantom{-CH}|\phantom{-CH}|$
     $\phantom{-CH-}OH$
     $CH_2-OH$.

A key intermediate in the preparation of compounds of formula I of Scheme XIV is a compound of formula II

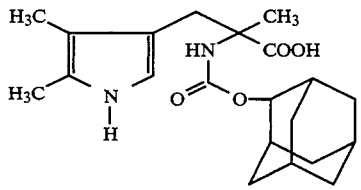

Schemes XIV and XV below illustrate the preparative steps in the process for making compounds of the instant invention. As shown, the pyrrolecarboxylic acid methyl ester 1 is protected on the pyrrole nitrogen by tosylation to give 3 which is reduced by Red-Al to the corresponding 4-hydroxymethyl compound 4. The alcohol 4 is converted to the corresponding chloride 5 using thionyl chloride in toluene. The chloromethyl derivative 5 is reacted with the carbanion derived from treating methyl N-benzalanate with sodium hydride in DMSO and the imine hydrolyzed with dilute hydrochloric acid to the HCl salt of aminoester 7. Treatment with potassium carbonate yielded the free aminoester 7. This aminoester reacted with 2-adamantyl chloroformate (8) to the methyl ester 9 which is hydrolyzed with potassium hydroxide in ethanol, followed by further acidic work up to give the carboxylic acid 10. This acid is condensed with the amines 11 as illustrated in Scheme XV to produce the final products 12.

The present invention is also concerned with compounds of the formula I and processes for the preparation thereof (see Scheme XVI)

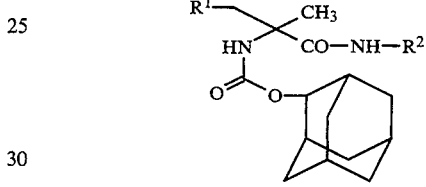

wherein $R^1$ is a group of the formula

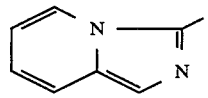

and $R^2$ is i) $-CH_2-CH_2-C_6H_5$ ii) $-CH-CH-C_6H_5$
     $\phantom{-CH}|\phantom{-CH}|$
     $\phantom{-CH-}OH$
     $CH_2-OH$.

A key intermediate in the preparation of compounds of formula I of Scheme XVI is a compound of formula II

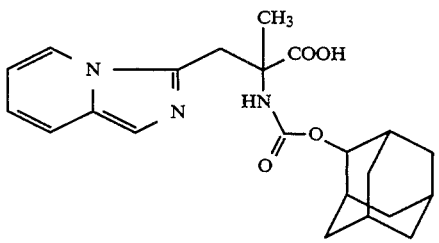

Schemes XIV and XV below illustrate the preparative steps in the process for making compounds of the instant invention. As shown, the pyrrolecarboxylic imidazo[1,5-a]pyridine (1) with formaldehyde and dimethylamine in acetic acid gives the Mannich base 2, which is converted to the corresponding methiodide 3 by reaction with ICH3 in ethanol. The methiodide 3 is reacted with the carbanion derived from treating N-benzalanate (4) with potassium t-butoxide in THF and the imine is hydrolyzed with dilute hydrochloric acid to the HCl salt of aminoester 5. Treatment with potassium carbonate gives the free aminoester 5 which is reacted with 2-adamantyl chloroformate (6) to the methyl ester 7, which is hydrolyzed with lithium hydroxide in dioxane/water, followed by further acidic work up to give the carboxylic acid 8. This acid (intermediate II) is condensed with the amines 9 as illustrated in Scheme XVII to produce the final products 10.

-continued
SCHEME XIV

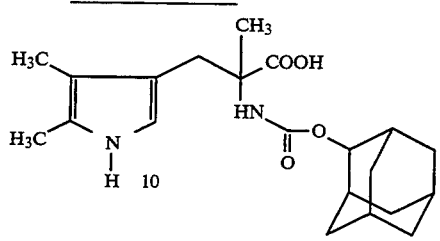

SCHEME XIV

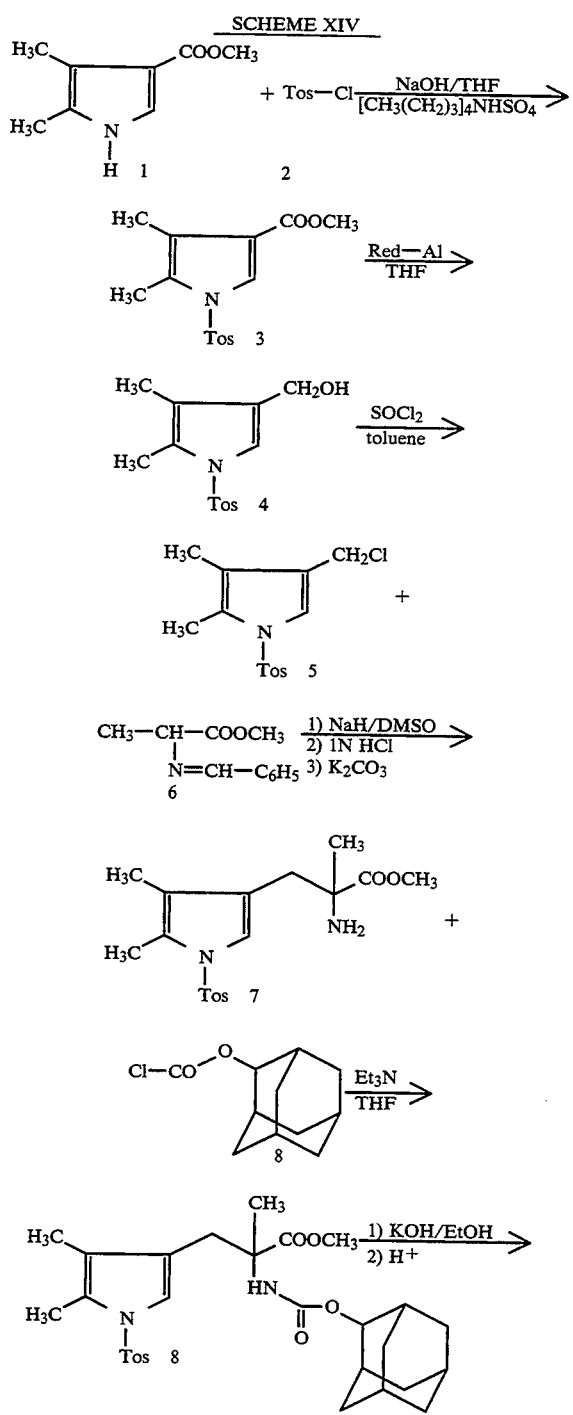

SCHEME XV

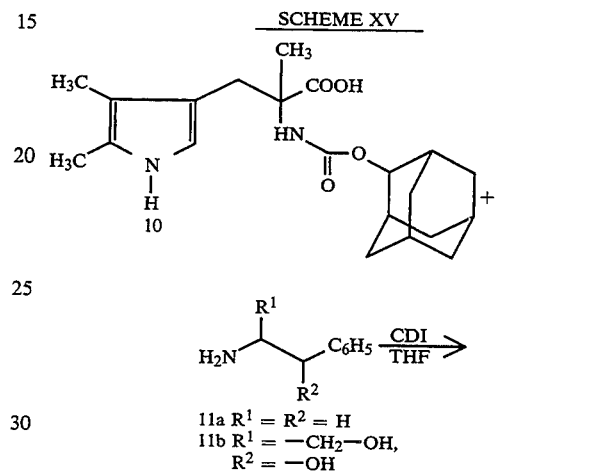

SCHEME XVI (continued)

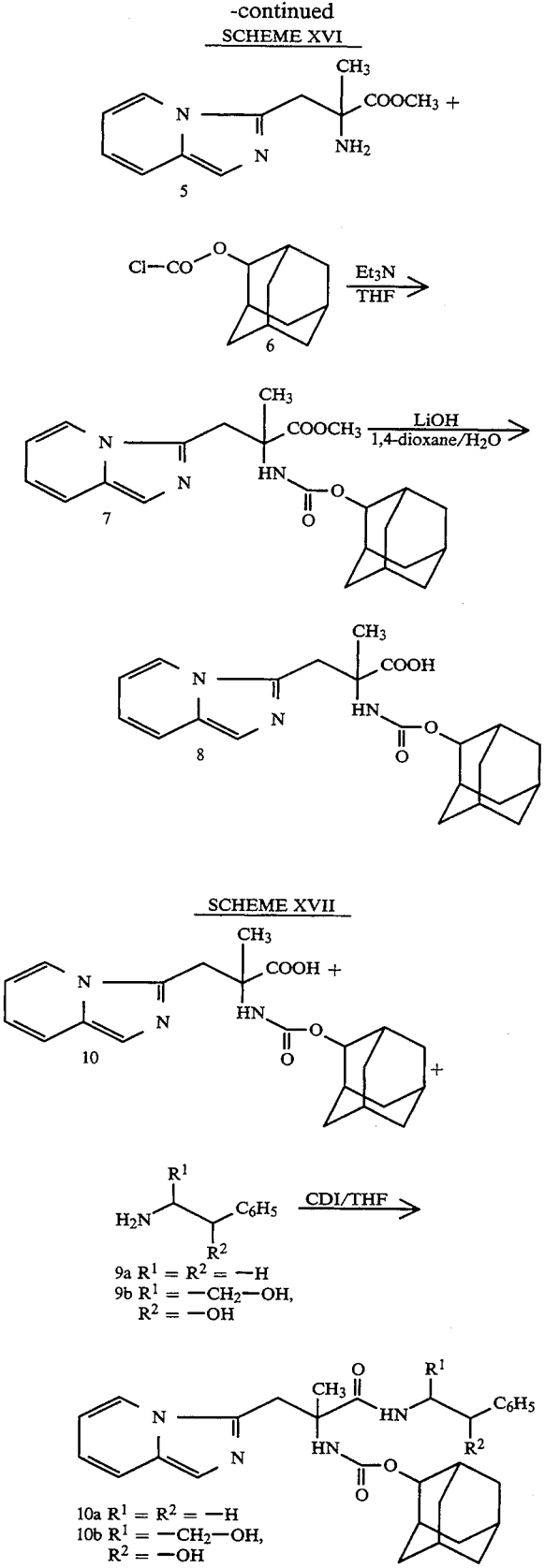

The present invention is concerned with compounds of the general formula I and processes for the preparation thereof

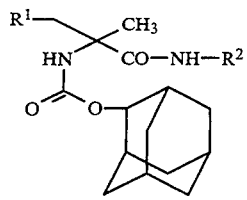

wherein $R^1$ is a group of the formula

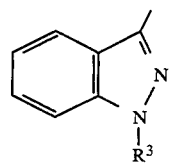

wherein $R^3$ is a hydrogen atom and $R^2$ is

   i)

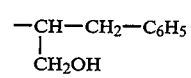   ii)

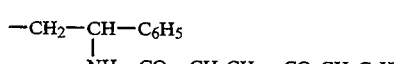   iii)

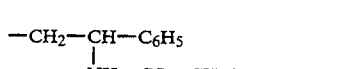   iv)

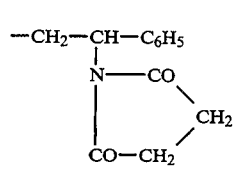   v)

A key intermediate in the preparation of compounds of formula I is a compound of formula below:

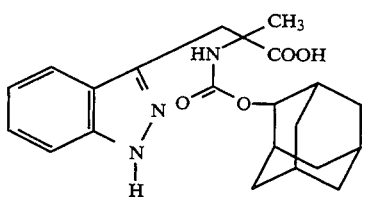

Compounds of formula I can be synthesized as shown in Scheme X and Scheme XI.

Scheme VIII (Route A) and Scheme IX (Route B) illustrate processes for the preparation of a compound of the above formula for the intermediate.

One process (Scheme VIII) involves reacting the quaternary salt 1 with the aldimine 3 in the presence of sodium hydride in dimethylsulfoxide (cf, for example, EP A 0037271). The Schiff base thus formed is not isolated and is subjected to hydrolysis with 1N hydrochloric acid to give the free amine 3. This is condensed with 2-adamantyl chloroformate (4) to give the methyl ester 5 which is hydrolyzed with lithium hydroxide in dioxane/water followed by further acid work up to give the free acid 6.

In another process (Scheme IX), the indazole methyl-3-carboxylate (7) is protected on the indazole 1-nitrogen by tosylation to give which is reduced by Red-A1 to the corresponding 3-hydroxymethyl compound 9. The alcohol is converted into the corresponding chloride 10 using thionyl chloride in toluene. The chloride 10 is used to alkylate the anion of the aldimine 2 (of, for example J. Heterocyclic Chem. 16:333, 1979). The above intermediate is not isolated and is subjected to hydrolysis with 1N hydrochloric acid to give the free amine 11. This amine is condensed with 2-adamantyl chloroformate (4) to give the methyl ester 12. which is hydrolyzed with potassium hydroxide in dioxane/water followed by further acid work-up to give the free carboxylic acid 6.

The acid 6 is condensed with amines such as illustrated in Scheme X to produce final products, for example, condensation of 6 with phenylethylamine gives compound 13a with (S)-(−)-2-amino-3-phenyl-1-propanol gives compound 13b and with (R)-4-[[(2-amino-1-phenyl)ethyl]amino]-4-oxobutanoic acid benzyl ester to give 13c and 13d.

The benzyl ester 13c is reduced to the free carboxylic acid 14 using hydrogen and 20% Pd(OH)$_2$ on carbon catalyst (Scheme XI).

BIOLOGICAL ACTIVITY

The biological activity of compounds of the present invention was evaluated employing an initial screening test which rapidly and accurately measured the binding of the tested compound to known CCK receptor sites. Specific CCK receptors have been shown to exist in the central nervous system. (See Hays, et al, *Neuropeptides* 1:53–62, 1980; and Satuer, et al, *Science* 208:1155–1156, 1980.)

In this screening test the cerebral cortices taken from male CFLP mice weighing between 30 to 40 g were dissected on ice, weighed, and homogenized in 10 volumes of 50 mM Tris-HCl buffer (pH 7.4 at 0° to 4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM MgCl$_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations of competitive test compound. In each case, the nonspecific binding was defined as that persisting in the presence of the unlabeled octapeptide CCK$_{26-33}$ (10$^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated pentagastrin were placed in polyethylene vials with 4 mL of scintillation cocktail, and the radioactivity was estimated by liquid scintillation spectrometry (efficiency 47% to 52%).

The specific binding to CCK receptor sites was defined as the total bound tritiated pentagastrin minus the amount of tritiated pentagastrin bound in the presence of 10$^{-6}$ octapeptide, CCK$_{26-33}$.

Saturation curves for specific tritiated pentagastrin binding to mouse cortical membranes were analyzed by the methods of Scatchard (*Ann. New York Acad. Sci.* 51:660–672, 1949; Hill, *J. Physiol.* 40:IV–VIII, 1910) to provide estimates for the maximum number of binding sites ($\beta_{max}$) and the equilibrium dissociation constant ($K_a$).

In displacement experiments, inhibition curves were analyzed by either logit-log plots or the iterative curve fitting computer program ALLFIT (DeLean, Munson, and Redbard, 1978) to provide estimates of the IC$_{50}$ and nH (apparent Hill coefficient) values). IC$_{50}$ values were defined as the concentration of test compound required to produce 50% inhibition of specific binding).

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table II.

Compounds of the present invention are expected to be useful as appetite suppressants as based on the tests described hereinbelow.

In the Palatable Diet Feeding assay, adult male hooded Lister rats weighing between 200 to 400 g were housed individually and trained to eat a palatable diet. This diet consisted of Nestles sweetened condensed milk, powdered rat food, and rat water which, when blended together, set to a firm consistency. Each rat was presented with 20 to 30 g of the palatable diet for 30 minutes per day during the light phase of the light-dark cycle over a training period of 5 days. The intake of palatable diet was measured by weighing the food container before and after the 30-minute access period (limits of accuracy 0.1 g). Care was taken to collect and correct for any spillage of the diet. Rats had free access to pellet food and water except during the 30-minute test period.

After the training period, dose-response curves were constructed for CCK8 and several representative compounds of the present invention (n=8 to 10 rats per dose level). MPE$_{50}$ values (±95% confidence limits) were obtained for the anorectic effects of these compounds.

In therapeutic use as appetite suppression agents, the compounds of the instant invention are administered to the patient at dosage levels of from about 200 to about 2800 mg per day.

Table II above shows the binding data for representative compounds of the invention.

Male hooded Lister rats (175–250 g) are housed individually and fasted overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of the acid secretion in the rat", *Brit. J. Pharmac.* 13:54–61, 1956, as described by Parsons in "Quantitative Studies of Drug-Induced Gastric Acid Secretion" (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.9% w/v NaCl. Basal pH is allowed to stabilize before administration of compounds is begun. Typically, 30 minutes elapses between surgery and the first compound administration.

The compounds of the instant invention are also expected to be useful as antiulcer agents as discussed hereinbelow.

Aspirin-induced gastric damage is assessed in groups of 10 rats each.

All animals are fasted for 24 hours before and throughout the experiment. Drug or vehicle is given 10 minutes before an oral dose of 1 mL of a 45-mg/mL suspension of aspirin in 0.5% carboxymethylcelulose (CMC).

The animals are sacrificed 5 hours after aspirin administration and the stomachs removed and opened for examination.

Gastric damage is scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages employed, however, may be varied depending upon the patient, the severity of the condition being treated, and the activity of the compound employed. Determination of optimum dosages is within the skill of the art.

The compounds of the instant invention are also expected to be useful as anxiolytic agents as described and discussed below.

Anxiolytic activity is assessed in the light/dark exploration test in the mouse (B. J. Jones, et al, Brit. J. Pharmac. 93:985-993, 1988). The compound is given PO in 0.1-, 1-, and 10-mg/kg doses.

The apparatus is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for 5 minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs are dissolved in water or saline and administered either subcutaneously, intraperitoneaily, or by mouth (PO) via a stomach needle.

The compounds of the instant invention are expected to be useful as antipsychotic agents. Compounds are tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12-hour light-dark cycle of lights-on between 07 hours, 00 minutes and 20 hours, 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14-day recovery period using stainless steel stylers, 0.3 mm diameter, which extended 0.5 mm beyond the guide tips.

Rats are manually restrained and the stylers removed. Intracerebral injection cannulae, 0.3 mm diameter, are inserted and drugs delivered in a volume of 0.5 µL over 5 seconds (a further 55 seconds was allowed for deposition) from Hamilton syringes attached via polythene tubing to the injection units. Animals are used on a single occasion only.

Behavioral experiments are conducted between 07 hours, 30 minutes and 21 hours, 30 minutes in a quiet room maintained at 22°±2° C. Rats are taken from the holding room and allowed 1 hour to adapt to the new environment. Locomotor activity is assessed in individual screened Perspex cages (25×15×15 cm (high)) (banked in groups of 30), each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time, animals are also observed for the presence of any nonspecific change in locomotor activity, e.g., sedation, prostration, stereotyped movements, that could interfere with the recording of locomotor activity.

The abilities of the compounds to inhibit the hyperactivity caused by the injection of amphetamine into the nucleus accumbens of the rat is measured.

An increase in locomotor activity follows the bilateral injection of amphetamine (20 µg) into the nucleus accumbens; peak hyperactivity (50 to 60 counts 5 minutes$^{-1}$) occurs 20 to 40 minutes after injection.

Intraperitoneal injection of the rats with a compound at 10, 20, or 30 mg/kg reduces the hyperactivity caused by the intra-accumbens injection of amphetamine. This test is known to be predictive of antipsychotic activity (Costall, Domehey & Naylor & tyers, *Brit. J. Pharmac.* 92:881–894).

The compounds of the instant invention are expected to prevent and treat the withdrawal response produced when chronic treatment by a drug is stopped or when alcohol abuse is stopped. These compounds are therefore useful as therapeutic agents in the treatment of drug or alcohol abuse as discussed and described below.

The effect of the compounds of the instant invention is illustrated, for example, in the mouse "light/dark box" test.

Animals are given nicotine, 0.1 mg/kg i.p. b.d. for 14 days. After a 24-hour withdrawal period, a compound is typically given at 0.1 to 100 mg/kg i.p. b.d. The increased time spent in the light area is a sensitive measure of the effect of the compound as an agent to treat withdrawal effects from nicotine.

The effect of long-term treatment and withdrawal from diazepam with intervention with a compound can be shown. Five mice are given diazepam at 10 mg/kg i.p. b.d. for 7 days. Withdrawal is for a 24-hour period; a compound of the invention is typically given at 0.01 to 100 mg/kg i.p. b.d. The increased time spent in the light section shows the effect of the compound.

The effect of a compound of the invention on the long-term treatment and withdrawal from diazepam. Five mice are given diazepam at 10 mg/kg j.p.b.d. for 7 days. The amount of time spent in the light section after the compound is administered demonstrates the effectiveness of the compound.

The effect of a compound of the invention on the long-term treatment and withdrawal from alcohol can be shown. Five mice are given alcohol in drinking water 8% w/v for 14 days. After a withdrawal period of 24 hours, a compound is typically given at 1.0 mg/kg j.p.b.d. The amount of time spent in the light section after the compound is administered demonstrates the effectiveness of the compound.

The effect of a compound of the invention on long-term treatment and withdrawal from alcohol can be shown. Five mice were given alcohol in drinking water, 8% w/v for 14 days. After a withdrawal period of 24 hours, the compound was given at 10 mg/kg i.p. b.d. The increased time spent in the light section shows the effect of the compound on the mice.

The effectiveness in the long-term treatment and withdrawal from cocaine can be shown. Five mice are given cocaine as 1.0 mg/kg i.p. b.d. for 14 days. The increased time in the light section illustrates the effectiveness of the compound in the treatment.

The effect of long-term treatment and withdrawal from cocaine with the intervention of a compound of the invention can be shown. Five mice are given cocaine at 1.0 mg/kg i.p. b.d. for 14 days after a withdrawal period of 24 hours, the compound is given at 1.0 mg/kg i.p. b.d. The effect of intervention with the compound is shown by the increase in time spent in the light section.

The anxiolytic effects of a compound of the invention in the Rat Social Interaction Test on a dose range of 0.001 to 1.0 mg/kg when paired rats are dosed s.c. The anxiolytic effect of the compound is indicated by the increase in time spent in social interaction compared with the control value C. (Costall, B., University of Bradford.)

The anxiolytic effects of a compound of the invention in the Rat Elevated X-Maze Test on a dose range of 0.01 to 1.0 mg/kg s.c. The anxiolytic effect is indicated by the time spent in the open arm end section compared with control C.

Compounds of the invention depress the flexor response in a stimulated spinalized decerebrated rat preparation similar to morphine. The effect of giving a compound with morphine greatly potentiates the effect which lasts for about 3 hours.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

A preferred pharmaceutically acceptable salt is the N-methyl glucamine salt.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

The following Examples 1–52 are illustrative of methods for preparing compounds of the instant invention. They are not intended to limit the scope of the invention.

Coupling Procedure

To a stirred solution of the urethane protected acid (0.5 mmol) in ethyl acetate (10 mL) was added pentafluorophenol or N-hydroxybenzotriazole (0.55 mmol) followed by DCC (0.6 mmol). The dicyclohexylurea formed was filtered off before the addition of the amino component (phenethylamine or L-phenylalaninol; 0.7 mmol) wherein the mixture was stirred overnight with a brief period at reflux if TLC indicated that activated ester was still present. The ethyl acetate solution was cooled, washed with dilute aqueous citric acid solution, dilute aqueous sodium bicarbonate solution, and finally saline solution before being dried (MgSO$_4$) and evaporated. The residual material was purified as indicated.

Scheme II above illustrates the preparation of compounds wherein Ar$^2$ is the sidechain for a genetically coded amino acid. The carboxylic acid 6 is esterified by treatment of a methanolic solution of the acid with thionyl chloride. The two free amines are then protected as the tert-butyl urethanes by treatment with di-tert-butyldicarbonate yielding 3. Treatment of this with benzylchloromethylether in dichloromethane gave the N-BOM-protected imidazole ring 9. The ester group was then hydrolyzed with lithium hydroxide in aqueous methanol to 10 and the pentafluorophenyl ester made using N,N'-dicyclohexyl carbodiimide. This active ester was then treated with 2-phenethylamine to give the amide 11 and the ring deprotected by hydrogenation using Pearlman's catalyst in ethanol yielding 12 (Example 13).

EXAMPLE 1

2-Adoc-α-methyl-DL-3(1-naphthyl)alanyl phenethylamide

A white powder was isolated in 39% yield from 2-Adoc-(α-methyl-DL-3(1-naphthyl)alanine following chromatography as described above, m.p. 184°-6° C. NMR (CDCl$_3$) δ 1.43 (3H, s), 1.51-2.01 (14H, m), 2.57 (2H, t, J=7Hz), 3.37 (2H, m, J=7Hz), 3.73 (2H, dd), 4.82 (1H, s), 5.16 (1H, s), 5.94 (1H, br.s), 7.01-8.11 (13H, m). IR (film); 1663, 1703 cm$^{-1}$. FAB-MS M+1:511.

EXAMPLE 2

2-Adoc-α-methyl-DL-3(1-naphthyl)alanyl-L-(1'-hydroxymethyl)phenethylamide

This was prepared in 47% yield from 2-Adoc-α-methyl-DL-3(2-naphthyl)alanine using a water soluble carbodiimide in place of DCC. Purification was by chromatography as described above and gave a noncrystalline solid. NMR (CDCl$_3$ δ 1.56 (3H, s), 1.61-2.07 (14H, m), 2.60-2.81 (2H, m), 3.37-3.57 (2H, m), 3.7-3.86 (2H, m), 3.98 & 4.17 (total 1H, 2br.s), 4.78 & 4.86 (total 1H, 2br .m) , 4.92 & 5.15 (total 1H, 2s), 6.05 (1H, m), 7.03-8.11 (13H, m). IR (film); 1665, 1700 cm$^{-1}$.

EXAMPLE 3

2-Adoc-α-methyl-DL-3 (2-naphthyl)alanyl phenethylamide

Starting from 2-Adoc-α-methyl-DL-3 (2-naphthyl) alanine this was isolated as a colorless solid following column chromatography as described above in 66% yield, m.p. 121°-128° C. NMR (CDCl$_3$) 8 1.45 (3H, s), 1.51-2.08 (14H, m), 2.79 (2H, m), 3.4 (2H, dd), 3.49-3.56 (2H, m), 2.91 (2H, br.d), 6.27 (1H, br.s), 7.12-7.28 (6H, m), 7.45 (2H, m), 7.55 (1H, s), 7.72-7.82 (3H, m) . IR (film); 1664 cm$^{-1}$. FAB-MS M+1:511.

EXAMPLE 4

2-Adoc-α-methyl-DL-3 (2-naphthyl)alanyl-L-(1'-hydroxymethyl)phenethylamide

Starting from 2-Adoc-α-methyl-DL-3 (2-naphthyl) alanine and following column chromatography (silica gel; 5% MeOH—CH$_2$Cl$_2$+1% AcOH) a white, noncrystalline solid was isolated in 36% yield. NMR (CDCl$_3$) δ 1.28 & 1.43 (3H, 2s), 1.54-2.15 (14H, m), 2.85 (2H, m), 3.23-3.52 (2.5H, m), 3.67 (1H, qd), 3.84 (0.5 H, dd), 4.08 & 4.24 (1H, 2m, 4.83 (1H, s), 4.89 & 5.01 (1H, s), 6.22 & 6.31 (1H, 2d), 7.13-7.27 (6H, m), 7.42-7.55 (3H, m), 7.71-7.82 (3H, m). IR (film); 1665, 1695 cm$^{-1}$. FAB-MS M+ +1:541.

EXAMPLE 5

2-Adoc-α-methyl-3(3-benzothienyl)alanyl phenethylamide

Starting with 2-Adoc-α-methyl-DL-3 (benzothienyl) alanine, column chromatography (silica gel; 4% MeOH—CH$_2$Cl$_2$) of the crude product gave a white solid in 80% yield, m.p. 129°-137° C. NMR (CDCl$_3$ δ 1.46 (3H, s), 1.5-1.98 (14H, m), 2.65 2H, t), 3.45 (2H, m), 3.53 (2H, dd), 4.81 (1H, s), 5.16 (1H, s ), 6.15 (1H, br.t), 7.07 (3H, m), 7.15-7.27 (3H, m), 7.3-7.39 (2H, m), 7.77-7.85 (2H, m). IR (film) 1644, 1677, 1704 cm$^{-1}$. FAB-MS M+ +1:517.

EXAMPLE 6

2-Adoc-(α-methyl-DL-3 (3-benzothienyl)alanyl-L-(1'-hydroxymethyl)phenethylamide

From 2-Adoc-α-methyl-DL-3 (benzothienyl)alanine and purification, as described above, yielded 67% of product as a white powder, m.p. 86°-91° C. NMR (CDCl$_3$) δ 1.29 & 1.47 (3H, 28), 1.53-1.98 (14H, m), 2.64-2.81 (3H, m), 3.32-3.61 (3.5H, m), 3.78 (0.5H, m), 4.03 & 4.22 (1H, 2m), 4.82 (1H, 28), 4.99 & 5.17 (1H, 2s), 6.16 & 6.23 (1H, d), 7.02-7.4 (10H, m), 7.75-7.86 (2H, m). IR (film) 1683 cm$^{-1}$. FAB-MS M+ +1:547.

EXAMPLE 7

2-Adoc-α-methyl-DL-3(2-bromo-3-benzofuranyl)alanylphenylethylamide

This was prepared from 2-Adoc-α-methyl-DL-3(2-bromo-3-benzofuranyl)alanine using a water soluble carbodiimide in place of DCC. Crude product was purified by column chromatography (silica gel; hexane-EtOAc:6-4) yielding 91% of a tan-colored noncrystalline solid. NMR (CDCl$_3$) δ 1.54 (3H, s), 1.55-2.03 (14H, m), 2.62 (2H, t), 3.29 (2H, dd), 3.41 (2H, m), 4.83 (1H, S), 5.27 (1H, br.s), 6.07 (1H, br.t), 7.05 (2H, d), 7.16-7.27 (5H, m), 7.41 (1H, d), 7.49 (1H, d). IR (film) 1665, 1704 cm$^{-1}$.

EXAMPLE 8

2-Adoc-α-methyl-DL-3(2 -bromo-3-benzofuranyl)alanyl-L-(1'-hydroxymethyl) phenethylamide Standard reaction of 2-Adoc-α-methyl-DL-3(2-bromo-3-benzofuranyl)alanine yielded a pale pink, noncrystalline solid in 89% yield which needed no further purification. NMR (CDCl$_3$) δ 1.34 & 1.55 (3H, 2s), 1.42-2.04 (14H, m), 2.54 & 2.69 (2H, 2m), 3.06-4.11 (4H, mm), 4.83 (1H, br.d), 5.05 & 5.25 (1H, 2s), 6.04 & 6.12 91H, 2d), 7.01-7.51 (9H, m). IR (film) 1668, 1698 cm$^{-1}$.

EXAMPLE 9

2-Adoc-α-methyl-DL-3 (2-benzimidazolyl)alanylphenethylamide

This was prepared in 24% overall yield from 2-Adoc-α-methyl-DL-3 (2-benzimidazolyl) alanine via the pentafluorophenyl ester as a white solid, m.p. 209°-211° C. IR (film) 1703, 1642 cm$^{-1}$. NMR (CDCl$_3$) δ 1.47-1.96 (17H, m), 2.68-2.82 (2H, m), 3.36-3.60 (4H, m), 4.73

(1H, s), 6.47 s), 7.06–7.25 (7H, m), 7.4–7.54 (3H, m) . FAB-MS M+:501 (100).

EXAMPLE 10

2-Adoc-α-methyl-DL-3(2-benzimidazolyl)alanyl-L-(1'-hydroxymethyl)phenethylamide Prepared via the pentafluorophenyl ester of 2-Adoc-α-methyl-DL-3 (2-benzimidazolyl) alanine as described above. Chromatography yielded the diastereomeric mixture as a white solid, m.p. 96°–103° C., in 13% overall yield. IR (film) 1696, 1658 cm$^{-1}$. NMR (CDCl$_3$) δ 1.48–2.03 (17H, m), 2.79–2.99 (2H, m), 3.46 (1H, dd, J=7.1 Hz), 3.51–3.93 (3H, m), 4.13–4.28 (1H, m), 4.73 & 4.8 (1H, 2s), 6.26 & 6.64 (1H, 2s), 6.87–7.52 (11 H, m). FAB-MS M+:531.

EXAMPLE 11

2-Adoc-α-methyl-DL-3(benzofuranyl)alanyl phenethylamide

A solution of the 2-bromo compound 2-Adoc-α-methyl-DL-3 (2-bromo-3-benzofuranyl)-alanylphenethylamide (0.33 mmol) in methanol (15 mL) was treated with DIPEA (0.42 mmol), 1,4-cyclohexadiene (4 mL) and 10% Pd/C. After a short induction period heat was evolved. Stirring was continued overnight, after which the catalyst was removed and all volatiles evaporated. The residue was taken up in ethyl acetate and this washed with water followed by dilute aqueous citric acid solution and finally dried. Evaporation of the solvent followed by chromatography of the residue as described above yielded a white foam containing no bromine atoms. NMR (CDCl$_3$) δ 1.36 (3H, s), 1.51–2.04 (14H, m), 2.73 (2H, t), 3.35 (4H, m), 4.74 (1H, s), 6.9 (1H, s), 7.22–7.34 (6H, m), 7.57 (3H,m), 7.91 (1H, m). IR (film) 1779 cm$^{-1}$.

The same product was isolated following debromination of the intermediate acid 2-Adoc-α-methyl-DL-3(2-bromo-3-benzofuranyl) alanine followed by coupling of the crude, unpurified intermediate to phenethylamine.

EXAMPLE 12

2-Adoc-α-methyl-DL-3(3-benzofuranyl)alanyl-L-(1'-hydroxymethyl)phenethylamide Debromination, as described above, starting from 2-Adoc-α-methyl-DL-3 (2-bromo-3-benzofuranyl)alanyl-L-(1'-hydroxymethyl)phenethylamide and phenylalaninol) noncrystalline. NMR (DMSO-d$_6$) δ 1.25 & 1.32 (3H, 2s), 1.48 (2H, m), 1.7–1.94 (12H, m), 2.67–2.91 (2H, m), 3.11–3.42 (4H, m), 3.97 (1H, m), 4.69 (1H, s), 6.75 & 6.92 (1H, 2s), 7.19–7.31 (7H, m), 7.54 (3H, m). IR (film) 1660, 1695 cm$^{-1}$.

EXAMPLE 13

Boc-α-methyl-DL-histidyl phenethylamide

Step 1

α-Methyl histidine (4.1 mmol) was esterified using thionyl chloride (30 mmol)/methanol (25 mL), giving the methyl ester dihydrochloride in 81% yield. NMR (D$_2$O) δ 1.64 (3H, s), 3.24 (1H, d, J=15.4 Hz) 3.38 (1H, d, J=15.8 Hz), 3.85 (3H, s), 7.25 (1H, s), 8.2 (1H, s).

Step 2

The methyl ester dihydrochloride (3.36 mmol) in methanol (10 mL) was treated with triethylamine (7.1 mmol) followed by di-tert butyl dicarbonate (7.4 mmol) and the mixture stirred at room temperature overnight. Removal of the solvent was followed by extraction of the residue with chloroform and this washed with 5% aqueous citric acid solution and water. The extracts were dried and evaporated to an oil, N$^α$,N$^τ$-bis-BOC histidine methyl ester, in 74% yield. NMR (CDCl$_3$) δ 1.44 (9H, s), 1.52 (3H, s), 1.61 (9H, s), 3.15–3.25 (2H, m), 3.76 (3H, s), 5.8 (1H, s), 7.12 (1H, s), 7.98 (1H, s).

Step 3

The methyl ester from Step 2 (2.5 mmol) was dissolved in dry dichloromethane (10 mL) and benzylchloromethyl ether (5.03 mmol) added. The mixture was stirred overnight. Removal of the solvent left a residue which was precipitated from methanol, giving the N$^α$-BOC, N$^π$Bom-histidine methyl ester hydrochloride, 100% yield. NMR (CDCl$_3$) δ 1.42 (9H, s), 1.49 (3H, s), 3.41 (2H, s), 3.46 (3H, s), 4.64–4.71 (4H, m), 5.7–5.8 (1H, m), 7.1 (1H, s), 7.27–7.36 (5H, m), 9.63 (1H, s).

Step 4

The ester from Step 3 (1.54 mmol) was treated with lithium hydroxide hydrate (7.7 mmol) in methanol (15 mL) at reflux for 2.5 hours. Removal of the solvent was followed by extraction of the residue with ether and this washed with water. Combined aqueous phases were acidified to pH 4.5 with aqueous 1N HCl solution and extracted with chloroform. After drying the extracts they were filtered and evaporated to a solid foam, the free acid, in 40% yield. NMR (CDCl$_3$) δ 1.44 (9H, s), 1.71 (3H, s), 3.19 (1H, d, J=15.2 Hz), 3.74 (1H, d, J=15.7 Hz), 4.45 (2H, s), 5.41 (1H, d, J=10.8 Hz), 5.46 (1H, d, J=10.8 Hz), 6.15 (1H, s), 6.92 (1H, s), 7.23–7.34 (5H, m), 7.77 (1H, br.s), 7.98 (1H, s).

Step 5

The free acid (0.62 mmol) was coupled to phenethylamine as described above for Examples 26–37. The crude product was isolated as an oil which could not be crystallized. 94%, IR (film) 1709, 1657 cm$^{-1}$. NMR (CDCl$_3$) δ 1.39 (12H, s), 2.75–2.82 (2H, m), 3.23 (1H, d, J=15.8 Hz), 3.38 (1H, d, J=15.8 Hz), 3.4–3.51 (2H, m), 4.48 (2H, s), 5.24–5.33 (2H, m), 5.74 (1H, s), 6.68–6.7 (1H, m), 6.9 (1H, s), 7.13–7.36 (10H, m), 7.71 (1H, s).

Step 6

The π-Bom group was removed from the imidazole ring of the intermediate from Step 5 (0.58 mmol) by hydrogenolysis in ethanol (50 mL) containing palladium hydroxide (70 mg) at a pressure of 50 psi at 500° C. for 6 hours. After removal of the catalyst and solvent, the residue was chromatographed (silica gel, MeOH—CH$_2$Cl$_2$ gradient 4–10% MeOH) giving the pure product as a white foam, 60%. IR (film) 1701, 1651 cm$^{-1}$. NMR (CDCl$_3$) δ 1.41 (9H, s) , 1.49 (3H, s), 2.76–2.81 (2H, m), 2.94 (1H, d, J=14.7 Hz), 3.18 (1H, d, J=14.7 Hz), 3.45–3.58 (2H, m), 5.8 (1H, br.s), 6.86 (1H, s), 7.15–7.32 (5H, m), 7.54 (1H, s). FAB-MS M+:373.

This BOC-α-methyl-DL-histidyl phenethylamide is then converted to a compound of the invention by . . .

EXAMPLE 14

(±)-[1-[(2-Hydroxyphenyl)methyl]-1-methyl-2-oxo-2-phenylethyl)amino]ethyl]carbamic acid tricyclo[3.3.1.1$^{3,7}$]dec-2-ylester (21)

Step 1 (14)

To a stored suspension of aqueous NaOH (33 g in H$_2$O, 33 mL, 0.83 mmol) in CH$_2$Cl$_2$ (250 mL) was added in one portion 2-hydroxybenzaldehyde (10 g, 81–87 mmol). After 30 minutes at room temperature, tetra-n-butyl ammonium bromide (2.64 g, 8.2 mmol) was added followed by dropwise addition of benzylbromide (9.8 mL, 82–39 mmol) over 10 minutes. The mixture was stirred at room temperature for 24 hours and the CH$_2$Cl$_2$ layer separated. This was washed with water (2×100 mL), dried over MgSO$_4$, filtered and the solvent removed in vacuo. Purification by chromatography over silica using 50% n-hexane/50% CH$_2$Cl$_2$ as eluant gave the product (15.31 g, 95%) as an oil; IR (film) 1688 and 1599 cm$^{-1}$. NMR (CDCl$_3$) δ 5.15 (2H, s), 6.97–0.03 (2H, m), 7.29–7.52 (6H, m), 7.83 (1H, dd, J 8.6, 2.6 Hz), 1.55

Step 2 (15)

NaBH$_4$ (2.0 g, 52–87 mmol) was added in portions to MeOH (20 mL) and stirred at 0° C. The aldehyde (5.0 g, 25.48 mmol) in MeOH (15 mL) was then added dropwise over 10 minutes and the cold mixture stirred for 30 minutes and then for 2 hours at room temperature. This was followed by dropwise addition of 1N NaOH (51 mL, 51.0 mmol) and stirring continued for 15 minutes. The mixture was extracted with Et$_2$O (2×50 mL), Et$_2$O dried over MgSO$_4$, filtered, and the solvent removed in vacuo to give the product as a syrup (4.45 g, 88%). IR (film) 3398, 3064, 3034, 1603, and 1590 cm$^{-1}$. NMR (CDCl$_3$) 2.37 (1H, bs), 4.71 (2H, s), b.09 (2H, s), 6.91–6.97 (2H, m), 7.21–7.42 (7H, m).

Step 3 (16)

Bromine (0.3 mL, 5.86 mmol) in CCl$_4$ (5 mL) was added dropwise to a stirred solution of triphenylphosphine (1.53 g, 5.83 mmol) in CCl$_4$ (25 mL), causing a yellow solid to precipitate. The mixture was stirred for 10 minutes at room temperature and then the alcohol (1.16 g, 5.83 mmol) and triethylamine (0.81 mL, 5.83 mmol) in CCl$_4$ (10 mL) was added dropwise over 10 minutes. The mixture was stirred for 5 hours at room temperature and the triphenylphosphine oxide which had precipitated was filtered off and the solvents removed in vacuo. n-Hexane (25 mL) was added to the residue, causing more triphenylphosphine oxide to precipitate. This was filtered off and the n-hexane removed in vacuo to give the product (1.30 g, 86%) as a syrup. IR (film) 3032 and 1601 cm$^{-1}$. NMR (CDCl$_3$) δ 4.60 (2H, s), 5.14 (2H, s), 6.89–6.94 (2H, m).

Step 4

To a stirred solution of alanine methyl ester hydrochloride (10 g, 71.64 mmol) and excess MgSO$_4$ in CH$_2$Cl$_2$ (100 mL) at room temperature was added f-chlorobenzaldehyde (10.06 g, 71.64 mmol) and then dropwise addition of triethylamine (10 mL, 71.64 mmol). After stirring at room temperature for 20 hours, the mixture was filtered and the solvent removed in vacuo. The residue was stirred in Et$_2$O and triethylamine hydrochloride filtered off and the Et$_2$O extract removed in vacuo, giving the product as an oil (15.69 g, 97%). IR (film) 1746 and 1645 cm$^{-1}$. NMR (CDCl$_3$) δ 1.52 (3H, d, J=6.7 Hz), 3.73 (3H, s), 4.16 (1H, q, J=6.7 Hz), 7.37 (2H, d, J=8.27 Hz), 7.70 (2H, d, J=8.4 Hz), 8.26 (1H, s).

Step 5 (17)

n-BuLi (4.9 mL) of a 16M solution in n-hexane, 7.84 mmol) was added via syringe to a stirred solution of diisopropylamine (1.1 mL, 7.89 mmol) in anhydrous THF (20 mL) at −78° C. under dry N$_2$. The cold solution was stirred for 30 minutes and then the Schiff base (1.58 g, 7.01 mmol) in anhydrous THF (10 mL) was added dropwise over 2 minutes. The mixture was stirred for 30 minutes at −78° C. and then 2-benzyloxy-benzyl bromide (1.83 g, 7.01 mmol) in anhydrous THF (10 mL) was added and the mixture stirred overnight at room temperature. The solvents were removed in vacuo and the syrup stirred for 1 hour in 1N HCl (15 mL, 15 mmol). The acidic solution was extracted once with Et$_2$O (20 mL), made pH 10 with 1N Na and extracted with Et$_2$O (2×25 mL). The Et$_2$O was dried to give the product (1.25 g, 60%) as a syrup. IR (film) 3370, 1732, and 1601 cm$^{-1}$. NMR (CDCl$_3$) δ 1.40 (3H, s), 2.53 (2H, b), 3.05 (1H, d, J=13.4 Hz), 3.16 (1H, d, J=13.3 Hz), 3.58 (3H, s), 5.06 (2H, s), 6.87–6.92 (2H, m), 7.12–7.44 (7H, m).

Step 6 (18)

Triethylamine (0.642 mL, 4.60 mmol) was added to a stirred solution of the amino ester (1.25 g, 4.18 mmol) in anhydrous THF (10 mL). This was followed by dropwise addition of 2-adamantylchloroformate (1.00 g, 4.60 mmol) in anhydrous THF (10 mL) over 10 minutes. After 3 hours at room temperature, the triethylamine hydrochloride was filtered off and the THF removed in vacuo. The residue was dissolved in Et$_2$O (25 mL) and washed with water (2×25 mL), Et$_2$O dried over MgSO$_4$, filtered, and the solvent removed in vacuo to give the product (1.80 g, 90%) as a foam. NMR (CDCl$_3$) δ 1.43–1.96 (17H, m), 3.13–3.23 (2H, m), 3.60 (3H, s), 4.74 (1H, s), 5.13 (2H, s), 6.10 (1H, b), 6.88–6.96 (2H, m), 7.05–7.08 (1H, m), 7.19–7.48 (6H, m).

Step 7 (19)

LiOH.H$_2$O (0.79 g, 18.85 mmol) was added in one portion to a stirred solution of the methyl ester (1.80 g, 3.77 mmol) in MeOH (20 mL) and the mixture heated at reflux for 6 hours. The MeOH was removed in vacuo and the residue partitioned between EtOAc (25 mL) and 1N HCl (25 mL). EtOAc dried over MgSO$_4$, filtered, and the solvent removed in vacuo to give the product (997 mg, 57%) as a foam. NMR (DMSO-d$_6$) δ 1.20 (3H, s), 1.24–2.04 (14H, m), 3.15 (1H, d, J=13.3 Hz), 3.22 (1H, d, J=13.4 Hz), 4.60 (1H, s), 5.11 (2H, s), 6.83–6.88 (1H, m), 6.99–7.07 (2H, m), 7.17–7.23 (1H, m), 7.30–7.48 (5H, m).

Step 8 (20)

1-Hydroxybenzotriazole monohydrate (0.092 g, 0.60 mmol) was added to a stirred solution of the acid (0.25 g, 0.54 mmol) in EtOAc (25 mL) and the mixture cooled to 0° C. To this stirred solution was added N,N'-dicyclohexylcarbodiimide (0.122 g, 0.59 mmol) and the mixture stirred for 1 hour. This was followed by 4-dimethylaminopyridine (0.017 g, 0.14 mmol) and then a solution of 2-phenethylamine (0.098 g, 0.81 mmol) in EtOAc (1 mL) and the mixture stirred at room temperature for 24 hours. The N,N'-dicyclohexylurea was filtered off and the EtOAc washed with aqueous 5% citric acid solution (2×25 mL), saturated NHCO₃ (2×25 mL), aqueous 5% citric acid solution (25 mL) and brine (25 mL). The EtOAc solution was dried over MgSO₄, filtered, and the solvent removed in vacuo. The residue was purified by chromatography over silica using 2% MeOH/98% CH₂Cl₂ as eluant which gave the product as a foam (0.232 g, 76%). IR (film) 3369, 1713, and 1658 cm⁻¹. NMR (CDCl₃) δ 1.42–1.88 (17H, m), 2.62–2.69 (2H, m), 3.14–3.19 (2H, m), 3.38–3.50 (2H, m), 4.70 (1H, s), 5.13 (1H, d, J=12.12 Hz), 5.17 (1H, d, J=12.1 Hz), 6.23 (1H, b), 6.35 (1H, b), 6.90–7.48 (14H, m).

Step 9

A solution of the benzyl ester (0.232 g, 0.41 mmol) in absolute EtOH (30 mL) was hydrogenated over 20% Pd (OH) 2-H₂O/C (0.1 g) at 30° C. under an H₂ atmosphere at 45 psi for 5 hours. The catalyst was filtered off and the solvents removed in vacuo and the residue purified by chromatography over silica using 2% MeOH/98% CH₂Cl₂ as eluant, giving the product (0.156 g, 80%) as a foam, m.p. 75°–84° C. IR (film) 3325, 1701, and 1651 cm⁻¹. NMR (CDCl₃ δ 1.51–1.93 (17H, m), 2.65–2.75 (2H, m), 3.06 (1H, d, J=14.2 Hz), 3.21 (1H, d, J=14.3 Hz), 3.40–3.51 (2H, m), 4.77 (1H, s), 5.97 (1H, b), 6.52 (1H, b), 6.80–7.27 (9H, m), 8.63 (1H, bs). Anal. (C₂₉H₃₆N₂O₄ 0.25 n-hexane); C, H, N.

EXAMPLE 15

(±)-tricyclo[3.3.1.1³,⁷]dec-2-ylester-[1-[2-aminophenyl)methyl]-1-methyl-2-oxo-2-](2-phenylethyl)-amino]ethyl]carbamic acid

Step 1

To a stirred solution of triphenylphosphine (2.76 g, 10.51 mmol) in CCl₄ (50 mL) was added a solution of bromine (0.54 mL, 10.54 mmol) in CCl₄ (5 mL) dropwise over 5 minutes. After 15 minutes, a solution of O-nitrobenzylalcohol (1.61 g, 10.51 mmol) and triethylamine (1.5 mL, 10.51 mmol) in CCH₄ (50 mL) was added dropwise over 15 minutes and the mixture stirred at room temperature for 4 hours. Triphenylphosphine oxide was filtered off and the solvent removed in vacuo to give a syrup. Addition of n-hexane (50 mL) caused more triphenylphosphine oxide to precipitate, which was removed by filtration and the solvent removed in vacuo to give the product (1.93 g, 85%) as a yellow crystalline solid.

Step 2

To a stirred solution of alanine methyl ester hydrochloride (10 g, 71.64 mmol) and excess MgSO₄ in CH₂Cl₂ (100 mL) at room temperature was added p-chlorobenzaldehyde (10.06 g, 71.64 mmol) and then dropwise addition of triethylamine (10 mL, 71.64 mmol). After stirring at room temperature for 20 hours, the mixture was filtered and the solvent removed in vacuo. The residue was stirred in Et₂O and triethylamine hydrochloride filtered off and the Et₂O extract removed in vacuo, giving the product as an oil (15.69 g, 97%). IR (film) 1746 and 1645 cm⁻¹. NMR (CDCl₃) δ 1.52 (3H, d, J=6.7 Hz), 3.73 (3H, s), 4.16 (1H, q, J=6.7 Hz), 7.37 (2H, d, J=8.2 Hz), 7.70 (2H, d, J=8.4 Hz), 8.26 (1H, s).

Step 3

To a stirred solution of diisopropylamine (1.1 mL, 7.63 mmol) in anhydrous THF (25 mL) at −78° C. was added n-BuLi (4.8 mL of a 1.6M solution in n-hexane, 7.68 mmol) via syringe. After 30 minutes at −78° C. the Schiff base (1.57 g, 6.94 mmol) in anhydrous THF (5 mL) was added dropwise over 5 minutes and stirring at −78° C. continued for a further 30 minutes. This was followed by a solution of o-nitrobenzyl bromide (1.5 g, 6.94 mmol) in anhydrous THF (5 mL) added over 5 minutes and the resulting mixture stirred overnight at room temperature. The solvents were removed in vacuo and the orange syrup stirred for 1 hour in 1N HCl (15 mL, 15 mmol). The aqueous solution was extracted once with Et₂O (25 mL), the aqueous solution made pH 10 with 1N NaOH, and over MgSO₄, filtered and the solvent removed in vacuo to give the product (0.814 g, 49%) as a syrup. NMR (CDCl₃) δ 1.32 (3H, s), 1.60 (2H, bs), 3.27 (1H, d, J=13.6 Hz), 3.55 91H, d, J=13.6 Hz), 3.69 (3H, s), 7.34–7.53 (3H, m), 7.84 (1H, dd, J=8.3, 1.4 Hz).

Step 4

Triethylamine (0.524 mL, 3.76 mmol) was added to a stirred solution of the amino ester (0.814 g, 3.42 mmol) in anhydrous THF (10 mL) at room temperature. This was followed by a solution of 2-adamantylchloroformate (0.808 g, 3.76 mmol) in anhydrous THF (10 mL) added dropwise over 10 minutes. The mixture was stirred at room temperature for 4 hours and the solvent removed in vacuo to give a syrup which was dissolved in Et₂O (25 mL) and washed with 1N HCl (25 mL) and brine (25 mL). The Et₂O was dried over MgSO₄, filtered, and the solvent removed in vacuo to give the product (1.33 g, 94%) as a foam. IR (film) 1742, 1713, and 1530 cm⁻¹.

Step 5

Lithium hydroxide monohydrate (0.67 g, 15.97 mmol) was added in one portion to a solution of the methyl ester (1.33 g, 3.19 mmol) in MeOH (25 mL) and the mixture heated at reflux for 6 hours. The solvent was removed in vacuo and the residue dissolved in EtOAc (25 mL) and washed with 1N HCl (25 mL) and brine (25 mL). EtOAc dried over MgSO₄, filtered, and the solvent removed in vacuo to give the product (1.1 g, 86%) as a foam. IR (film) 1714 cm⁻¹. NMR (DMSO-d₆) 1.05 (3H, s), 1.48–2.03 (14H, m), 3.46 (1H, d, J=13.9 Hz), 3.65 (1H, d, J=13.9 Hz), 4.65 (1H, s), 7.14 (1H, bs), 7.28 (1H, d, J=7.8 Hz), 7.45–7.61 (2H, m), 7.85 (1H, dd, J=8.0, 1.1 Hz), 12.58 (1H, bs).

Step 6

1-Hydroxybenzotriazole monohydrate (0.126 g, 0.82 mmol) and N,N'-dicyclohexylcarbodiimide (0.170 g, 0.83 mmol) were added to a stirred solution of the acid (0.300 g, 0.75 mmol) in EtOAc (10 mL) at 0° C. and the mixture stirred for 1 hour. This was followed by 4-dimethylaminopyridine (0.023 g, 0.19 mmol) and 2-phenethylamine (0.137 g, 1.13 mmol) in EtOAc (2 mL) and the mixture stirred at 0° C. for 2 hours and then at room temperature for 48 hours. The N,N'-dicyclohexylurea was filtered off and the EtOAc washed with aqueous 5% citric acid solution (2×10 mL), saturated NaHCO₃ solution (2×10 mL), 5% citric acid solution (10 mL), and brine (10 mL). The EtOAc was dried over MgSO₄, filtered, and the solvent removed in vacuo. Using 2% MeOH/98% CH₂Cl as eluant gave the product (0.243 g, 64%) as a white solid, m.p. 164.5°–169° C. IR (film) 1711, 1656, and 1527 cm⁻¹. NMR (CDCl₃) δ

1.47–1.96 (17H, m), 2.76 (2H, t, J=7.1 Hz), 3.38–3.55 (3H, m), 3.66 (1H, d, J=14.2 Hz), 4.78 (1H, s), 5.67 (1H, bs), 6.17 (1H, m), 7.12–7.46 (8H, m), 7.80 (1H, dd, J=8.0, 1.3 Hz). Anal. ($C_{29}H_{35}N_3O_5$) C, H, N.

Step 7

A solution of the product from Step 6 (0.187 g, 0.37 mmol) in absolute EtOH (40 mL) was hydrogenated over 10% Pd/C (40 mg) at 30° C. under an $H_2$ atmosphere at 45 psi for 6 hours. The catalyst was filtered and washed with EtOH (40 mL) and the solvent removed in vacuo. Purification of the residue by chromatography over silica using 2% MeOH/98% $CH_2Cl_2$ as eluant gave the product (0.157 g, 89%) as a white solid, m.p. 66°–72° C. IR (film) 3346, 1705, and 1659 cm$^{-1}$. NMR (CDCl$_3$) δ 1.54–1.94 (7H, m), 2.65–2.76 (2H, m), 2.94 (1H, d, J=14.5 Hz), 3.17 (1H, d, J=14.5 Hz), 3.37–3.51 (2H, m), 3.85 (2H, bs), 4.76 (1H, s), 6.93–7.27 (7H, m). Anal. ($C_{29}H_{37}N_3O_3$) C, H, N.

EXAMPLE 16

Step 1

β-(2,3-Dihydro-1-methyl-5-phenyl-1H-1,4-benzodiazepin-2-yl)-α-methyl-alanine methyl ester diastereomeric mixture A suspension of sodium hydride (0.76 g, 25.5 mmol) in 70 mL dimethylsulfoxide was heated for 90 minutes under nitrogen at 70° C. After cooling to room temperature a solution of methyl N-benzalalanate (J. W. Tilley, P. Levitan, R. W. Kirstead, *J. Heterocyclic Chem.*, 16, 333 (1979) (4.9 g, 25.5 mmol) in 10 mL dimethylsulfoxide was added. After stirring 30 minutes at room temperature, the dark red solution became dark green.

A solution of 2-chloromethyl-2,3-dihydro-1-methyl-5-phenyl-1H-1,4-benzodiazepine (U.S. Pat. No. 4,325,957) (7.23 g, 25.5 mmol) in a mixture of 25 mL dimethylsulfoxide and 15 mL tetrahydrofuran was added. The resulting slurry was stirred 30 minutes at room temperature and 90 minutes at 70° C.

The reaction mixture was diluted with 250 mL water and extracted with ether. The ethereal phase was washed with water, dried over magnesium sulfate, and concentrated in vacuo. The oily residue (10 g) was purified by column chromatography on silica gel with a mixture of methylene chloride/methanol (98:2) as eluant.

The first fraction was educt (1.28 g), followed by 2,3-dihydro-2-hydroxymethyl-1-methyl-5-phenyl-1H-1,4-benzodiazepine (0.62 g) and the desired product (3.36 g, 37% yield) as a dark red oil.

Step 2

N-[(2-Adamantyloxy)carbonyl]-β-(2,3-dihydro-1-methyl-5-phenyl-1H-1,4-benzodiazepin-2-yl)-α-methyl-alanine methyl ester diastereomeric mixture To a stirred solution of β-(2,3-dihydro-1-methyl-5-phenyl-1H-1,4-benzodiazepin-2-yl) -α-methyl-alanine methyl ester (diastereomeric mixture, 0.35 g, 1 mmol) in 10 mL tetrahydrofuran at 4° C. was added a solution of 2-adamantyl chloroformate (0.25 g, 1.16 mmol) in 3 mL tetrahydrofuran, followed by dropwise addition of N-ethyldiisopropylamine (0.3 g, 2.3 mmol), dissolved in 3 mL tetrahydrofuran.

After 24 hours, the reaction mixture was filtered, the solvent removed in vacuo, and the oily residue diluted with ethyl acetate. The ethyl acetate solution was washed twice with 5% citric acid and once with saturated brine. The organic layer was dried over magnesium sulfate. The solvent was removed in vacuo to give an oil residue (0.6 g), which was purified by flash chromatography on silica gel to yield the title compound (0.39 g, 65% yield) as a yellow oil.

Step 3

N-[(2-Adamantyloxy)carbonyl]-β-(2,3-dihydro-1-methyl-5-phenyl-1H-1,4-benzodiazepin-2-yl)-α-methyl-alanine diastereomeric mixture To a stirred solution of N-[(2-adamantyloxy)carbonyl]-β-(2,3-dihydro-1-methyl-5-phenyl-1H-1,4-benzodiazepin-2-yl )-α-methyl-alanine methyl ester (diastereomeric mixture, 5.3 g, 10 mmol) in a mixture of 150 mL dioxane and 75 mL water was added lithium hydroxide (0.72 g, 30 mmol).

After stirring overnight, dioxane was removed in vacuo. The aqueous phase was extracted with ethyl acetate to remove unreacted ester. The basic phase was acidified with 5% citric acid, pH 3, and extracted with ethyl acetate. The organic layer was dried over magnesium sulfate and concentrated in vacuo to yield the title compound as an orange foam (5.27 g, quantitative).

Step 4

N-[(2-Adamantyloxy)carbonyl]-β-(2,3-dihydro-1-methyl-5-phenyl-1H-1,4-benzodiazepin-2-yl)-α-methyl-alanine-2-phenyethylamide diastereomeric mixture To a stirred suspension of N-[(2-adamantyloxy)-carbonyl]-β-(2,3-dihydro-1-methyl-5-phenyl-1H-2,4-benzodiazepin-2-yl)-α-methyl-alanine (diastereomeric mixture, 0.52 g, 1 mmol) in 15 mL dry ethyl acetate at room temperature was added pentafluorophenol (0.2 g, 1.1 mmol) followed by addition of a solution of N,N-dicyclohexylcarbodiimide (0.23 g, 1.1 mmol) in 5 mL dry ethyl acetate at 4° C. The reaction mixture was kept at this temperature for 16 hours. The precipitate was filtered off and 2-phenylethylamine (0.133 g, 1.1 mmol) was added. After stirring 16 hours at room temperature the solvent was removed in vacuo. The oily residue was separated by flash chromatography using a mixture of methylene chloride and ethyl acetate (9:1 to 3:1).

Diastereomer 1

Diastereomer 1 was obtained as yellow crystals (0.09 g), m.p. 140°–145° C. Rf=0.34 (methylene chloride-:ethyl acetate=3:1).

Diastereomer 2

A second crystalline fraction was obtained as a yellow foam (0.16), m.p. 60°–70° C. It was a mixture of nine parts diastereomer 2 and four parts diastereomer 1. Rf=0.41 (methylene chloride:ethyl acetate=3:1).

EXAMPLE 17

Step A

α-Methyl-β-(2-pyridyl-1-oxide)-D,L-alanine methyl ester

To a suspension of potassium t-butoxide (11.22 g, 100 mmol) in 300 mL tetrahydrofuran at −30° C. was added a solution of methyl N-benzalalanate (J. W. Tilley, P. Levitan, R. W. Kierstead, *J. Heterocyclic Chem*, 16, 333 (1979) (19.12 g, 100 mmol) in 100 mL dry tetrahydrofuran. The mixture was stirred for 30 minutes at this temperature followed by addition of a solution of 2-chloromethyl-pyridine-1-oxide (14.36 g, 100 mmol) in 100 mL DMSO. This mixture was stirred for 3 hours at −25° C. and then warmed to room temperature. The reaction mixture was diluted with 1.5 L of methylene chloride, washed with water (5×), and dried over magnesium sulfate. Methylene chloride was removed in vacuo to give the Schiff base (25.65 g, 86% yield). To the stirred solution of the Schiff base in 500 mL methanol at 0° C. was added gaseous HCl. After 1 hour methanol was removed in vacuo to give the dihydrochloride of α-methyl-β-(2-pyridyl-1-oxide)-D,L-alanine methyl ester (20,6 g, 85% yield) as a white solid after recrystallization from methanol/diethyl ether, m.p. 144°–147° C.

Step B

N-[(2-Adamantyloxy)carbonyl]-α-methyl-β-(2-pyridyl-1-oxide)-D,L-alanine methyl ester To a stirred suspension of α-methyl-β-(2-pyridyl-1-oxide)-D,L-alanine methyl ester dihydrochloride (4.25 g, 15 mmol) in 50 mL dry tetrahydrofuran at room temperature was added diisopropylethylamine (4.52 g, 35 mmol). The mixture was stirred for 30 minutes followed by addition of a solution of 2-adamantyl chloroformate (3.22 g, 15 mmol) in 10 mL tetrahydrofuran and a solution of diisopropylethylamine (2.33 g, 18 mmol) in 10 mL tetrahydrofuran. After 24 hours, the reaction mixture was filtered, the solvent removed in vacuo, and the oily residue diluted with ethyl acetate. After filtration, the ethyl acetate solution was washed twice with 5% citric acid and once with saturated brine. The organic phase was dried over magnesium sulfate and the solvent removed in vacuo to yield the title compound as a colorless foam (5.68 g, 97% yield).

Step C

N-[(2-Adamantyloxy)carbonyl]-α-methyl-β-(2-pyridyl-1-oxide)-D,L-alanine

To a stirred solution of N-[(2-adamantyloxy)carbonyl]-α-methyl-β-(2-pyridyl-1-oxide)-D,L-alanine methyl ester (5.83 g, 15 mmol) in a mixture of 150 mL dioxane and 100 mL water was added under nitrogen lithium hydroxide (1.2 g, 50 mmol). After stirring overnight, dioxane was removed in vacuo. The aqueous phase was extracted with ethyl acetate to remove unreacted ester. The basic phase was acidified with 5% citric acid to pH 3 and extracted with ethyl acetate (and a little bit ethanol). The organic layer was dried over magnesium sulfate and concentrated in vacuo to yield the title compound as a white solid (5.39 g, 96% yield), m.p. 230°–242° C.

Step D, Method A

N-[(2-Adamantyloxy)carbonyl-α-methyl-β-(2-pyridyl-1-oxide)-D,L-alanine-2-phenylethylamide To a stirred suspension of N-[(2-adamantyloxy)carbonyl)-α-methyl-β-(2-pyridyl-1-oxide)-D,L-alanine (2.43 g, 6.5 mmol) in 150 mL dry tetrahydrofuran at −20° C. was added N-methylmorpholine (0.76 g, 7.5 mmol) and isobutyl chloroformate (1.02 g, 7.5 mmol). The mixture was stirred for 20 minutes at this temperature followed by addition of 2-phenethylamine (1.21 g, 10 mmol), stirred for 3 hours at −25° C., and then warmed to room temperature. The solvent was removed in vacuo at room temperature, and the residue was diluted with ethyl acetate and water. The solution was washed with 5% citric acid (3×) and water (2×) followed by 5% potassium hydrogen carbonate (3×), water (2×), and brine. The organic phase was dried over magnesium sulfate. The solvent was removed in vacuo to yield an oily residue which crystallized by addition of diethyl ether/n-hexane (2.76 g, 89% yield), m.p. 76°–80° C.

Step D, Method B

N-[(2-Adamantyloxy)carbonyl]-α-methyl-β-(4l-pyridyl-1-oxide)-D,L-alanine-2-phenylethylamide To a stirred suspension of N-[(2-adamantyloxy)-carbonyl)-α-methyl-β-(4-pyridyl-1-oxide)-D,L-alanine (0.37 g, 1 mmol) in 20 mL dry tetrahydrofuran at room temperature was added N,N-carbonyldiimidazole (0.16 g, 1 mmol). The mixture was stirred for 3 hours followed by addition of 2-phenylethylamine (0.12 g, 1 mmol). After stirring overnight the intermediate imidazoide could still be detected by TLC (methylenechloride: methanol=4:1). Additional amount of 2-phenylethylamine (0.12 g, 1 mmol) was added. After stirring 4 hours at room temperature no imidazolide could be detected. The solvent was removed in vacuo at 40° C. The crystalline residue was washed with water and recrystallized from ethyl acetate to yield the title compound (0.28 g, 59% yield), m.p. 120°–126° C.

Step D, Method C

N-[(2-Adamantyloxy)carbonyl]-α-methyl-β-(4-pyridyl-1-oxide)-D,L-alanine-(1S-hydroxyethyl-2-phenyl)ethylamide mixture of diastereomers To a stirred suspension of N-[(2-adamantyloxy)-carbonyl)-α-methyl-β-(4-pyridyl-1-oxide)-D,L-alanine (0.75 g, 2 mmol) in 40 mL dry ethyl acetate at room temperature was added pentafluorophenol (0.41 g, 2.2 mmol) followed by addition of a solution of N,N'-dicyclohexylcarbodiimide (0.45 g, 2.2 mmol) in 8 mL dry ethyl acetate at 4° C. The reaction mixture was stirred 48 hours at this temperature. The precipitate was filtered and a solution and a solution of (S)-(—)-2-amino-3-phenyl-propanol in 10 mL dry ethyl acetate was added. After stirring 16 hours at room temperature the solvent was removed in vacuo. The residue was separated by flash chromatography using ethyl acetate:ethanol=9:1. Diastereomer 1 was obtained as a foam (0.42 g, 41% yield). Diastereomer 2 was obtained as a foam (0.50 g, 49% yield).

Step E (±)-Tricyclo[3.3.1.1$^{3,7}$]dec-2-yl [1-methyl-2-oxo-2-[(2-phenylethyl)amino]-1-[(2-pyridinyl)methyl]ethyl]-carbamate A solution of N-[(2-adamantyloxy) carbonyl]-α-methyl-β-(2-pyridyl-1-oxide)-D,L-alanine-2-phenethylamide (1.64 g, 3.4 mmol) in 50 mL ethyl acetate was hydrogenated (30 bar hydrogen pressure, room temperature) over 350 mg of 10% palladium on charcoal overnight. The reaction mixture was filtered and evaporated to give an oil, which was purified by flash chromatography with ethyl acetate. The solvent was removed in vacuo to yield the title compound as an oil, which solidified on cooling (0.34 g, 21% yield), softening at 40°–43° C.

EXAMPLE 18

N-[(2-Adamantyloxy)carbonyl]-α-methyl-β-(3-pyridyl-1-oxide)-D,L-alanine-2-phenylethylamide

Step A

α-Methyl-β-(3-pyridyl-1-oxide)-D,L-alanine methyl ester

The method is as described in Step A, Example 17, except 3-chloromethyl-pyridine-1-oxide was used. An extremely hygroscopic dihydrochloride was obtained in 99% yield.

Step B

N-[(2-Adamantyloxy)carbonyl]-α-methyl-β-(3-pyridyl-1-oxide)-D,L-alanine methyl ester The method is as described in Step B, Example 17, except α-methyl-β-(3-pyridyl-1-oxide)-D,L-alanine methyl ester dihydrochloride was used. The desired product was obtained in 26% yield as colorless crystals, m.p. 160°–163° C. Rf=0.64 [chloroform:methanol:N-H₄OH(conc.)=250:50:8].

Step C

N-[(2-Adamantyloxy)carbonyl]-α-methyl-β-(3-pyridyl-1-oxide)-D,L-alanine

The method is as described in Step C, Example 17, except N-[(2-adamantyloxy)carbonyl]-α-methyl-β-(3-pyridyl-1-oxide)-D,L-alanine methyl ester was used. The title compound was isolated in 88% yield as a white solid, m.p. 228°–231° C.

Step D

N-[(2-Adamantyloxy)carbonyl]-α-methyl-β-(3-pyridyl-1-oxide)-D,L-alanine-2-phenylethylamide The method is as described in Step D, Method A, Example 17, except N-[(2-adamantyloxy)carbonyl]-α-methyl-β-(3-pyridyl-1-oxide )-D,L-alanine was used. The product was obtained in 89% yield as a white solid, m.p. 76°–80° C. Rf=0.72 [chloroform:methanol:N-H₄OH (conc.)=250:50:8.

EXAMPLE 19

Step A

α-Methyl-β-(4-pyridyl-1-oxide)-D,L-alanine methyl ester

The method is as described in Step A, Example 17, except 4-chloromethyl-pyridine-1-oxide was used. A very hygroscopic dihydrochloride was obtained in 89% yield. Rf(base)=0.47 (methylene chloride:methanol=4:1).

Step B

N-[(2-Adamantyloxy)carbonyl]-α-methyl-β-(4-pyridyl-1-oxide)-D,L-alanine methyl ester The method is as described in Step B, Example 17, except α-methyl-β-(4-pyridyl-1-oxide)-D,L-alanine methyl ester dihydrochloride was used. The waxy product was obtained in 77% yield. Rf=0.77 (methylene chloride:methanol=4:1).

Step C

N-[(2-Adamantyloxy)carbonyl]-α-methyl-β-(4-pyridyl-1-oxide)-D,L-alanine

The method is as described in Step C, Example 17, except N-[(2-adamantyloxy)carbonyl]-α-methyl-β-(4-pyridyl-1-oxide)-D,L-alanine methyl ester was used. The product was obtained in 45% yield as a white solid, m.p. 224°–225° C.

EXAMPLE 19A

N-[(2-Adamantyloxy)carbonyl]-α-methyl-β-(2-pyridyl-1-oxide)-D,L-alanine-(1S-hydroxymethyl-2-phenyl)ethylamide mixture of diastereomers The method is as described in Step D, Method A, except (S)-(−)-2-amino-3-phenyl-propanol was used. The diastereomeric mixture, obtained in 85% yield, was separated by flash chromatography using methylene chloride at first and afterwards methylene chloride:methanol=98:2. Diastereomer 1 was obtained as a foam softens at 74°–76° C. Rf=0.27 (methylene chloride:methanol=95:5). Diastereomer 2 was obtained as a foam softens at 59°–67° C. Rf=0.16 (methylene chloride:methanol=95:5).

EXAMPLE 20

Carbonic acid, 2-[[2-methyl-1-oxo-3-(3-pyridinyl-1-oxide)-2-[[(tricyclo[3.3.1.1³,⁷]dec-2-yloxy)carbonyl]amino]propyl]-amino]-3-phenylpropyl-2-methylpropylester (Pyridine center RS, other center S) and Carbamic acid, [2-[[1-(hydroxymethyl)-2-phenylethyl]amino]-1-methyl-2-oxo-1-[(3-pyridinyl N-oxide)methyl]ethyl], tricyclo[3.3.1.1³,⁷]dec-2-yl ester (Hydroxymethyl center S, other center R or S) mixture of diastereomers The method is as described in Example 17, Method A, except N-[(2-adamantyloxy)carbonyl]-α-methyl-β-(3-pyridyl-1-oxide)-D,L-alanine and (S)-(−)-2-amino-3-phenyl-propanol were used. The complex reaction mixture was separated by flash chromatography using ethyl acetate:methanol=3:1.

Carbonic acid ester

The ester was obtained in 6% yield as a colorless foam softens at 77°–80° C. Rf=0.54 (ethyl acetate:methanol=3:1).

Carbamic acid esters

Diastereomer 1 was obtained in 7% yield as a colorless foam softens at 94°–98° C. Rf=0.36 (ethyl acetate:methanol=3:1). Diastereomer 2 was obtained in 2% yield as a colorless foam softens at 98°–102° C.

EXAMPLE 21

Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]-carbamate (Hydroxymethyl center S, other center R or S) (Diastereomer 1)

The method is as described in Example 17, except diastereomer 1 of Example 19A was used. The product was obtained in 26% yield as a colorless foam softens at 62°–65° C. Rf=0.34 (ethyl acetate).

EXAMPLE 22

Tricyclo[3.3.1.1$^{3,7}$]dec-2-yl
[2-[[1-(hydroxymethyl)-2-phenylethyl]amino]-1-methyl-2-oxo-1-(2-pyridinylmethyl)ethyl]-carbamate hydroxymethyl center S, other center R or S)
(Diastereomer 2)

The method is as described in Example 17, except diastereomer 2 of Example 19A was used. The product was obtained in 37% yield as a colorless foam softens at 61°–64° C. Rf=0.35 (ethyl acetate).

EXAMPLE 23

(±)-Tricyclo[3.3.1.1$^{3,7}$]dec-2-yl
[1-methyl-2-oxo-2-[(2-phenylethyl)amino]-1-(3-pyridinylmethyl)ethyl]-carbamate The method is as described in Example 17, except the phenylethylamide of Example 18 was used. The product was obtained in 54% yield as a colorless solid, m.p. 167°–169° C. Rf=0.24 (ethyl acetate).

EXAMPLE 24

Carbonic acid,
2-[[2-methyl-1-oxo-3-(3-pyridinyl)-2-[[(tricyclo[3.3.1.1$^{3,7}$]dec-2-yloxy)carbonyl]amino]-propyl]amino]-3-phenylpropyl2-methylpropyl ester (Pyridine center RS, other center S)

The method is as described in Example 17, except carbonic ester of Example 9 was used. The product was obtained in 31% yield as a colorless foam softens at 56°–58° C. Rf=0.43 (ethyl acetate).

EXAMPLE 25

Tricyclo[3.3.1.1$^{3,7}$]dec-2-yl[2-[[1-(hydroxymethyl)-2-phenylethyl]amino]-1-methyl-2-oxo-1-(3-pyridinylmethyl)ethyl]-carbamate (hydroxymethyl center S, other center R or S) (Diastereomer 1)

The method is as described in Example 17, except diastereomer 1 of Example 20 was used. The product was obtained in 77% yield as a colorless solid, m.p. 163°–164° C. Rf=0.65 (ethyl acetate:methanol=3:1).

EXAMPLE 26

Tricyclo[3.3.1.1$^{3,7}$]dec-2-yl
[2-[[1-(hydroxymethyl)-2-phenylethyl]amino]-1-methyl-2-oxo-1-(3-pyridinylmethy)ethyl]-carbamate (hydroxymethyl center S, other center R or S)
(Diastereomer 2)

The method is as described in Example 17, except diastereomer 2 of Example 20 was used. The product was obtained in 50% yield as a colorless solid, m.p. 63°–67° C. Rf=0.62 (ethyl acetate:methanol=3:1).

EXAMPLE 27

(±)-Tricyclo[3.3.1.1$^{3,7}$]dec-2-yl
[1-methyl-2-oxo-[(2-phenylethyl)amino]-1-(4-pyridinylmethyl)ethyl]-carbamate The method is as described in Example 17, except the phenylethylamide of Example 17/Step D, Method B was used. The product was obtained in 35% yield as a colorless solid, m.p. 176° C. Rf=0.55 (methylene chloride:methanol=9:1).

EXAMPLE 28

Tricyclo[3.3.1.1.$^{3,7}$]dec-2-yl[2-[[1-(hdroxymethyl)-2-phenylethyl]amino]-1-methyl-2-oxo-1-(4-(pyridinylmethyl)ethyl]-carbamate (hydroxymethyl center S, other center R or S). (Diastereomer 1)

The method is as described in Example 17, except diastereomer 1 of Example 17, Step D, Method C was used. The product was obtained in 34% yield as colorless crystals, m.p. 169°–171° C. Rf=0.46 (methylene chloride:methanol=9:1).

EXAMPLE 29

Tricyclo [3.3.1.1$^{3,7}$]dec-2-yl
[2-[[1-(hydroxymethyl)-2-phenylethyl]amino]-1-methyl-2-oxo-1-(4-pyridinymethyl)ethyl]-carbamate (hydroxymethyl center S, other center R or S)
(Diastereomer 2)

The method is as described in Example 17, except diastereomer 2 of Example 17, Step D, Method C was used. The product was obtained in 56% yield as a beige amorphous powder, m.p. 90°–100° C. Rf=0.44 (methylene chloride:methanol=9:1).

EXAMPLE 30

Tricyclo[3.3.1.1$^{3,7}$]dec-2-yl[1-methyl-2-oxo-2-[(2-phenylethyl)amino]-1-(1-[methylsulfonyl]pyrido[3,4-b]indol-3-yl-methyl)ethyl]carbamate, (±)

Step 1

To a stirred solution of 1H-β-carboline-3-carboxylic acid methylester (4.44 g, 19.6 mmol) in THF (500 mL) was added LiBH$_4$ (2.56 g, 118 mmol) and the reaction mixture was stirred for 8 hours. The solution was cooled in an ice/water bath, treated with 65 mL water and stirred on while warming to room temperature. The mixture was evaporated in vacuum, diluted with 400 mL water and extracted with ethyl acetate (400 mL) followed with methylene chloride (400 mL). The combined organic layers were dried over Na$_2$SO$_4$ and evaporated in vacuum. The residue was treated with 2N HCl (100 mL) and the solution was extracted with methylene chloride. The aqueous solution was made basic with 2N NaOH (pH=9–10) and the precipitate was filtered, washed with water and dried in vacuum (2.25 g, 57.8%).

Step 2

A solution of 3-(hydroxymethyl)-1H-β-carboline (1.38 g, 7 mmol) in methylene chloride (30 mL) was cooled to −20° C. and diisopropylethylamine was added. To this solution was added mesyl chloride (1.60 g, 14 mmol) dropwise with stirring. After 5 minutes ice water was added, the organic layer was separated, washed with water, dried over Na$_2$SO$_4$ and methylene chloride was evaporated in vacuum at room temperature. 25 mL THF were added and the solution was used for the next step.

Step 3

The Schiffs' base (1.34 g, 7.0 mmol), derived from alanine methyl ester and benzaldehyde was dissolved in THF (25 mL), and cooled to −76° C. To this was added a solution of LDA (11.6 mL of 10% in n-hexane) in THF (15 mL). After stirring for 30 minutes this solution was treated with 3-(methylsulfonylmethyl)-9-methyl-sulfonyl-β-carboline (25 Ml in THF) from Step 2, warmed to room temperature and stirred over night. The brown suspension was evaporated in vacuum, the residue dissolved in ethyl acetate and the solution was washed with water, combined with 100 mL 1N HCl and was stirred for 1 hour at room temperature. The organic layer was separated and the aqueous solution was treated with Na$_2$CO$_3$ to pH 8–9. This was extracted with ethyl acetate (2×100 mL), dried over Na$_2$SO$_4$ and the organic solvent was evaporated in vacuum. The residue was flash chromatographed on silica gel using 5% methanol/methylene chloride to yield 2-[9-(methylsulfonyl)-β-carbolin-3-yl]-alanine methyl ester (0.53 g, 21.2%) as a yellow oil.

Step 4

To a stirred solution of 2-[9-(methylsulfonyl)-β-carbolin-3-yl]-alanine methylester (0.5 g, 1.4 mmol) in THF (10 mL) was added 2-adamantyloxycarbonyl chloride (345 mg, 1.7 mmol) and the solution was treated with diisopropyl ethylamine (219 mg, 1.7 mmol) in THF (5 mL). The reaction mixture was stirred for 4 hours at room temperature, evaporated in vacuum and partitioned between ethyl acetate (100 mL) and water (50 mL). The organic layer was separated, washed successively with 7.5% citric acid solution (50 mL), 8% NaHCO$_3$ solution (50 mL) and then dried over Na$_2$SO$_4$. The solvent was evaporated in vacuum and N-(2-adamantyloxy-carbonyl)-2-[9-(methylsulfonyl)-β-carbolin-3-yl]-alanine methylester was isolated as a yellow oil which solidified upon drying (0.73 g, 97.7%).

Step 5

In a mixture of dioxane (10 mL) and water (5 mL) was stirred N-(2-adamantyloxycarbonyl)-2-[9-(methylsulfonyl)-β-carbolin-3-yl]-alanine methylester (0.73 g, 1.4 mmol) and lithium hydroxide (131 mg, 5.5 mmol) over 16 hours at room temperature. Dioxane was evaporated in vacuum, the residue was diluted with water (10 mL), 7.5% citric acid solution was added (ph=6) and the organic components were extracted with ethyl acetate (50 mL). The organic extract was washed with saturated salt solution and dried over Na$_2$SO$_4$. After removing the solvent in vacuum N-(2 -adamantyloxycarbonyl)-2- [9-(methylsulfonyl)-β-carbolin-3-yl]-alanine was isolated as a yellow foam (0.68 g, 95.5%).

Step 6

N-(2-adamantyloxy-carbonyl)-2-[9-(methylsulfonyl)-β-carbolin-3-yl]-alanine (330 mg, 0.63 mmol) was dissolved in DMF (5 mL) and cooled to 0° C. To this was added sequentially with stirring (in 3 minute intervals) hydroxybenzotriazole (85 mg, 0.63 mmol), dicyclohexylcarbodiimide (130 mg, 0.63 mmol) and phenylethylamine (76 mg, 0.63 mmol) in DMF (3 mL). The solution slowly warmed to room temperature and stirred over 16 hours. The reaction mixture was filtered free of precipitate and evaporated in vacuum. The residue was dissolved in ethyl acetate (50 mL) and washed successively with 7.5% citric acid solution, saturated NaHCO$_3$ solution (50 mL) and saturated salt solution (50 mL). The organic layer was dried over Na$_2$SO$_4$ and evaporated in vacuum to give a foam. The reaction mixture was separated on silica gel with ethyl acetate:methylene chloride=1:1. Carbamic acid, [1-methyl-2-oxo-2-[(2-phenylethyl)amino]-1-[3[9-(methylsulfonyl)]β-carbolinyl]methyl]ethyl]-tricyclo[3.3.1.1$^{3,7}$]-dec-2-yl ester (0.215 g, 54.4%) was isolated as a white foam. m.p. 89°–92° C.

EXAMPLE 31

Tricyclo[3.3.1.3,7]dec-2-yl[2-[[1-(hydroxymethyl)-2-phenylethyl]amino]-1-methyl-2-oxo-1-(1-[methylsufonyl]-pyrido[3,4-b]-indol-3-ylmethyl)ethyl]carbamate (mixture of diastereomers, phenylethyl center is R)

Synthetic method was as described for Example 30 Step 6 but using (S)-(−)-2-amino-3-phenyl-1-propanol. The crude residue was chromatographed over silica gel using ethyl acetate:methylene chloride 1:1 as eluant to obtain the title compound (0.135 g, 35.9%) as a foam, m.p. 78°–83° C.

EXAMPLE 32

Tricyclo[3.3.1.1$^{3,7}$]dec-2-yl [1-methyl-2-oxo-2-[(2-phenylethyl)-amino]-1-(1H-pyrido[3,4-b]indol-3-yl-methyl)ethyl]carbamate, (±)

Step 1

To thionylchloride (50 mL) was added 3-(hydroxymethyl)-1H-β-carboline (2.60 g, 13.12 mmol) and the reaction mixture was refluxed for 1 hour. After cooling down to room temperature the mixture was evaporated in the vacuum and treated with ether (300 mL). The gray solid was collected by filtration, washed with ether and dried in the vacuum to give 3-(chloromethyl)-1H-β-carboline hydrochloride (3.3 g, 100%).

Step 2

In THF (85 mL) was dissolved the Schiffs' Base (2.45 g, 12.8 mmol), derived from alanine methyl ester and benzaldehyde, and cooled to −40° C. To this was added potassium-t-butoxide (2.92 g, 26 mmol) and the orange solution stirred under nitrogen at −40° C. for 30 minutes. To this was added 3-(chloromethyl)-1H-β-carboline hydrochloride salt (3.24 g, 12.8 mmol), the reaction mixture stirred for another 30 minutes at −40° C. and then slowly warmed to room temperature overnight. The black solution was evaporated in the vacuum and then partitioned between ethyl acetate (150 mL) and water (50 mL). To the organic layer was added 1N HCl (100 mL) and the mixture was stirred for 2 hours. Then the organic was separated, washed with Na$_2$CO$_3$ solution, dried over Na$_2$SO$_4$ and evaporated in the vacuum to give 2-(9H-β-carboline-3-yl)-alanine methyl ester (2.4 g, 50.5%) as a light tan foam.

Step 3

Synthetic method was as described for Example 30, Step 4, but using 2-(9H-β-carboline-3-yl)-alanine methyl ester (2.4 g, 8.4 mmol) from Step 2 to give N-(2-adamantyloxy-carbonyl)-2-(9H-β- carboline-3-yl)-alanine methyl ester (1.1 g, 28.2 g).

Step 4

Method was as described for Example 30, step 5, but using N-(2-adamantyloxy-carbonyl)-2-(9H-β-carboline-3-yl )-alanine methyl ester (1.0 g, 2.2 mmol). N-(2-adamantyloxy-carbonyl)-2 -(9 H-β-carboline-3-yl )-alanine (0.9 g, 93.1%) was isolated as a yellow solid.

Step 5

Synthetic method was as described for Example 30 Step 6 but using N-(2-adamantyloxy-carbonyl)-2-(9H-β-carboline-3-yl)-alanine. The crude residue was chromatographed over silica gel using ethyl acetate:methylene chloride=5:1 as eluant to obtain the title compound (0.46 g, 83.5%). top. 94°-103° C.

EXAMPLE 33

Tricyclo [3.3.1.1$^{3,7}$]dec-2-yl[2-[[1-(hydroxymethyl)-2-(phenylethyl]amino]-1-methyl-2-oxo-1-(1H-pyrido[3,4-b]indol-3-ylmethyl)ethyl]carbamate (mixture of diastereomers, phenylethyl center is R)

Synthetic method was as described for Example 30, Step 6, but using (S)-(−)-2-amino-3-phenyl-1-propanol. The crude residue was chromatographed on silica gel using ethyl acetate:methylene chloride=5:1 as eluant to obtain the title compound (0.21 g, 36.2%). m.p. 76°-92° C.

EXAMPLE 34

Carbamic acid, [1-methyl-2-oxo-2-[(2-phenylethyl)-amino]-1-[(2-quinolinyl)methyl]ethyl]tricyclo-[3.3.1.1$^{3,7}$]dec-2-yl ester, (±)-

Step 1

To a solution of chinaldine (14.3 g, 0.1 mmol) and N-bromosuccinimide (17.8 g, 0.1 mmol)in CCl$_4$ (150 mL) was added benzoylperoxide (2.6 g, 0.025 mol) and the mixture was heated under reflux for 4 hours. The reaction mixture was cooled to room temperature and evaporated in vacuum. The residue was treated with 5% HBr solution, the precipitate was filtered off and the filtrate was treated with celite and then basified with NaHCO$_3$ solution. The product was extracted with ether and crystallized from petrolether to yield 2-(bromomethyl)-quinoline (2.8 g, 12.6%) as light tan crystals.

Step 2

Method was as described for Example 30, Step 3 but using 2-(bromo-methyl)-quinoline (7.0 g, 30 mmol) and Schiff's Base (6.03 g, 30 mmol). The product was obtained without chromatography but with crystallization methods using diethylether (3.4 g, 38.6%).

Step 3

A solution of 2-quinolinyl-2-methyl-alanine methyl ester (4.1 g, 16.8 mmol) (40 ml) and 2-adamantyloxycarbonyl chloride (4.5 g, 20.8 mmol) in anhydrous THF (40 mL) at room temperature was treated with pyridine (1.6 g, 20.8 mmol). The reaction mixture was stirred for 2 hours at RT, the organic solvent was evaporated in vacuum and the residue was dissolved in ethyl acetate. The precipitate was filtered, the filtrate evaporated in vacuum and the residue dissolved in ether and filtered again. The filtrate evaporated in vacuum to obtain N-(2-adamantyloxycarbonyl)-2-(quinolinyl)-alanine methyl ester (3.6 g, 38.0%) as a light tan solid.

Step 4

Method was as described for Example 30, Step 5, but using N-(2-adamantyloxy-carbonyl)-2-(quinolin-yl)-alanine methyl ester (3.5 g, 8.3 mmol) to obtain N-(2-adamantyloxy-carbonyl)-2-(quinolin-yl)-alanine (2.0 g, 59.0%) as a beige solid from n-pentane.

Step 5

Synthetic method was as described for Example 30, Step 6, but using N-(2-adamantyloxy-carbonyl)-2-(quinolin-yl)-alanine (0.40 g, 1 mmol). The crude residue was chromatographed on silica gel using dichloromethane:methanol=18:1 as eluant to yield the title compound (0.12 g, 24%) as a solid from ether/pentane, m.p. 75°-76° C.

EXAMPLE 35

Carbamic acid, [2-[[1-(hydroxymethyl)-2-phenylethyl]amino]-1-methyl-2-oxo-1-(2-quinolinylmethyl)ethyl], tricylo[3.3.1.1$^{3,7}$]dec-2-ester (hydroxymethyl center is S, other center is R,S)

Method was as described for Example 30, Step 6, but using N-(2-adamantyloxy-carbonyl)-2-(quinolin-yl)-alanine (0.40 g, 1 mmol) prepared in Example 34, Step 4. The crude residue was chromatographed on silica gel using dichloromethane/methanol (18:1) as eluant to yield the title compound (40 mg, 10%), m.p. 75°-86° C.

EXAMPLE 36

Carbamic acid, [1-methyl-2-oxo-2-[(2-phenylethyl)amino]-1-[(3-quinolinyl)methyl]ethyl]-, tricyclo[3.3.1.1$^{3,7}$]dec-2-yl ester, (±)-

Step 1

To a solution of quinoline-3-carboxylic acid (25 g, 0.14 mmol) in dry THF (100 mL) was added N,N'-carbonyldiimidazole (23.4 g, 0.14 mmol) in portions and the reaction mixture was stirred at room temperature for 2 hours. The organic solvent was evaporated in vacuum and the residue was dissolved in dry ethanol (200 mL). Sodium (0.1 g) was added and the reaction mixture was refluxed for 2 hours. The alcohol was evaporated in vacuum and quinoline-3-carboxylic ethyl ester (27.1 g, 93.5%) was isolated from ethanol/water=1:1 (150 mL) at 5° C. as a white crystalline compound.

Step 2

To a solution of quinoline-3-carboxylic ethyl ester (10.0 g, 50 mmol) in anhydrous diethylether (250 mL) was added at −15° C. LAH (2.5 g, 66 mmol) in portions over 10 minutes. The reaction mixture was stirred for 2 hours at room temperature and 4 mL water was added. The organic layer was separated and the precipitate of the hydroxides was treated with hot ethanol (100 mL). The organic solutions were combined and treated with 47% HBr solution. The oily phase washed with ether, dissolved in ethanol (40 mL) and the product was separated by addition of diethyl ether. The precipitate was separated and treated with ethyl acetate to yield 3-(hydroxymethyl)-quinoline hydrobromide (3.0 g). After evaporating the ethanol/ether mixture and treating the residue with ethyl acetate another 5.3 g of the product was isolated. Yield: 8.3 g (69.7%).

Step 3

A solution of 3-(hydroxymethyl)-quinoline hydrobromide (5.3 g, 22 mmol) in thionylchloride (15 mL) was heated to reflux for 30 minutes. The reaction mixture was evaporated in vacuum, the residue was taken up in ethyl acetate and washed with NaHCO$_3$solution. The dark brown organic solution was washed with water, decolorized with celite, dried over Na$_2$SO$_4$ and evaporated in vacuum. 3-(Chloromethyl)-quinoline (2.2 g, 37.3%) crystallized from n-pentane in white needles (turning brown standing at room temperature)

Step 4

Synthetic method was as described for Example 32, Step 2, but using 3-(chloromethyl)-quinoline (2.2 g, 12 mmol). The reaction mixture was chromatographed on silica gel using ethyl acetate:ethanol (9:1) to give 3-quinolinyl-2-methyl-alanine methyl ester 0.7 g, 23.1%) as a light brown solid.

Step 5

Method was as described for Example 30, Step 4, but using 3-quinolinyl-2-methyl-alanine methyl ester (0.7 g, 3 mmol). N-(2-adamantyloxy-carbonyl)-3-(quinolin-yl)-alanine methylester (1.0 g, 83.3%) was obtained as a solid after drying.

Step 6

Method was as described for Example 30, Step 5, but using N-(2-adamantyloxy-carbonyl)-3-(quinolin-yl)-alanine methylester (1.0 g, 2 mmol) to obtain N-(2-adamantyloxy-carbonyl)-3-(quinolin-yl)-alanine (0.41 g, 42.4%) as a solid from n-pentane.

Step 7

Synthetic method was as described for Example 30, Step 6, but using N-(2-adamantyloxy-carbonyl)-3-(quinolin-yl)-alanine (0.40 g, 1 mmol). The residue chromatographed on silica gel using ethyl acetate as eluant to obtain the title compound as a solid from n-pentane, m.p. 130°-133° C.

EXAMPLE 37

Carbamic acid,
[1-methyl-2-oxo-2-[(2-phenylethyl)amino]-1-[(4-quinolinyl)methyl]ethyl]-tricyclo-[3.3.1.1$^{3,7}$]dec-2-yl ester, ($\pm$)-

Step 1

Method was as described for Example 36, Step 1, but using quinoline-4-carboxylic acid. The crude reaction mixture was chromatographed on silica gel using ethyl acetate as a eluant to obtain quinoline-4-carboxylic acid methylester (28.6 g, 98.6%) as a oil.

Step 2

To a solution of quinoline-4-carboxylic acid methylester (10.0 g, 50 mmol) in anhydrous diethylether (250 mL) was added LAH (2.5 g, 66 mmol) in portions over a period of 20 minutes at $-10°$ C. The reaction mixture stirred for 1 hour at 0° C. and then water (4 mL) was added. The organic layer was separated and the precipitate of the hydroxides was treated with hot ethanol (50 mL). The combined organic solutions were treated with 47% HBr, the red precipitate was filtered off and treated with methanol. 4-(Hydroxymethyl)-quinoline hydrobromide (200 mg) was isolated as a white solid. The diethylether/ethanol mixture was concentrated in vacuum to yield 4.0 g (33.6%) of the product.

Step 3

A reaction mixture of 4-(hydroxymethyl)-quinoline hydrobromide (2.0 g, 12.6 mmol) and thionylchloride (20 mL) was heated to reflux for 2 hours. This was allowed to cool and then concentrated in vacuum. The green solid was treated with ethyl ether, filtered, washed with ethyl ether and dried in vacuum to yield 4-(chloromethyl)-quinoline hydrochloride (2.17 g, 80.7%).

Step 4

Method was as described for Example 32, Step 2, but using 4-(chloromethyl)-quinoline, (derived from 4-(chloromethyl)-quinoline hydrochloride (5.5 g, (30 mmol) and NaHCO$_3$). The crude reaction mixture was chromatographed on silica gel (flash) using ethyl acetate/cyclohexane=4:1 as an eluant to separate the impurities and then ethyl acetate/ethanol=9:1 to obtain 4-quinolinyl-2-methyl-alanine methylester (1.8 g, 25.7%) as a solid from n-pentane.

Step 5

Method was as described for Example 30, Step 4, but using 4-quinolinyl-2-methyl-alanine methyl ester to obtain N-(2-adamantyloxy-carbonyl)-3-(quinolin-yl)-alanine methyl-ester (3.2 g, 74.4%) as a light brown solid upon drying.

Step 6

Method was as described for Example 30, Step 5, but using N-(2-adamantyloxy-carbonyl)-4-(quinolin-yl)-alanine methylester to yield N-(2-adamantyloxy-carbonyl)-3-(quinolin-yl)-alanine (2.3 g, 74.2%) as a solid from n-pentane.

Step 7

Method was as described for Example 30, Step 6, but using N-(2-adamantyloxy-carbonyl)-4-(quinolin-yl)-alanine. The crude product mixture was extracted with 7.5% citric acid solution, dried over Na$_2$SO$_4$ and evaporated in vacuum. The residue was chromatographed on silica gel using ethyl acetate as eluant to obtain the title compound (80 mg, 40.0%) as a light brown solid from ethylether/n-pentane, m.p. 83°-85° C.

EXAMPLE 38

Carbamic acid,
[2-[[1-(hydroxymethyl)-2-phenylethyl]-amino]-1-methyl-2-oxo-1-(4-quinolinylmethyl)ethyl]-,
tricylo-[3.3.1.1$^{3,7}$]dec-2-yl ester (hydroxymethyl center is S, other center is R,S)

Method was as described for Example 30 but using N-(2-adamantyloxy-carbonyl)-4 -(quinolin-yl)-alanine from Example 37, Step 6. The crude product mixture was extracted with 7.5% citric acid solution, dried over Na$_2$SO$_4$ and evaporated in vacuum. The residue was chromatographed on silica gel using ethyl acetate as eluant to obtain the title compound which was crystalized from ether/n-pentane to give a solid (40 mg, 8%). m.p. 85°-90° C.

EXAMPLE 39

4-[[2-[[2-methyl-1-oxo-2-(2-quinolinyl)-2-[[tricyclo-[3.3.1.1$^{3,7}$]dec-2-yloxy)carbonyl]amino]propyl]amino]-1-phenylethyl]amino]-4-oxobutanoic acid (mixture of [R-(R*,R*)] and [R-(R*,S*)] isomers

Step 1

A reaction mixture of N-(2-adamantyloxy-carbonyl)-2-methyl-3-(quinolin-2yl)-alanine (1.54 g, 3.8 mmol) from Example 34, Step 4 and N,N-carbonyldiimidazole (0.68 g, 4.2 mmol) was dissolved in THF (15 mL) and stirred at room temperature overnight. The reaction mixture was cooled down with ice and a solution of 2-(N-BOC-amino)-2-phenylamine (1.13 g, 4.2 mmol) in THF (4.0 mL) was added. After reaction overnight the organic solvent was evaporated in vacuo, the residue dissolved in ethyl acetate, washed with 7.5% citric acid and NaHCO$_3$ solution, and dried in vacuo. The organic solution was evaporated in vacuo and the residue flash chromatographed on silica gel using toluene/ethanol (1% to 3%) as eluant to give carbamic acid, [2-[[2-(N-BOc-amino)-2-phenyl]amino]-1-methyl-2-oxo-1-(2-quinolinylmethyl)ethyl]-, tricyclo[3.3.1.1$^{3,7}$]dec-2-yl ester as a solid from ether (400 mg).

Step 2

To a solution of carbamic acid, [2-[[2-(N-BOC-amino)-2-phenyl]amino]-1-methyl-2-oxo-1-(2-quinolinylmethyl)ethyl]-, tricyclo [3.3.1.1$^{3,7}$]dec-2-yl ester (200 mg, 0.32 mmol) in dichloromethane (8 mL) was added p-toluenesulphonic acid monohydrate (76 mg) and the reaction mixture stirred over 24 hours. Another portion of p-toluenesulphonic acid monohydrate (76 mg) was added, the reaction mixture was stirred overnight, diluted with ethyl acetate, and washed with 1N NaOH. The organic layer was dried over Na$_2$SO$_4$, evaporated in vacuo and carbamic acid, [2-[[2-amino-2-phenyl]amino]-1-methyl-2-oxo-1-(2-quinolinylmethy)ethyl]-, tricyclo[3.3.1.1$^{3,7}$]dec-2-yl ester ws isolated as a solid (180 mg).

Step 3

A solution of [2-[[2-amino-2-phenyl]amino]-1-methyl-2-oxo-1-(2-quinolinylmethyl)ethyl]-, tricyclo[3.3.1.1$^{3,7}$]-dec-2-yl ester (112 mg, 0.21 mmol) in dry ethyl acetate (2 mL) was given to a mixture of succinic anhydride (22 mg, 0.22 mmol) and DMAP (26 mg, 0.22 mmol) in dry ethyl acetate (2 mL) and heated to reflux for 2.5 hours. The reaction mixture was cooled to room temperature and ethyl acetate was added (50 mL). The solution was washed with 7.5% citric acid solution, dried over N$_2$SO$_4$ and evaporated in vacuo to isolate the title compound (140 mg, 93%), m.p. 93°–106° C. (D-(−)-N-methylglucamate salt).

EXAMPLE 40

Butanoic acid,
4-[[2-(4-quinolinylmethyl)-1-oxo-2-[[(tricyclo[3.3.1.1$^{3,7}$]dec-2-yl]carbonyloxy)amino]-propyl]-amino]-1-phenylethyl]amino]-4-oxo-, [R-(R*,R*)]-

Step 1

A reaction mixture of N-(2-adamantyloxycarbonyl)-4-(quinolinyl)alanine (610 mg, 1.25 mmol) and N,N'-carbonyldiimiazole (245 mg, 1.6 mmol) was dissolved in dry THF (5 mL) and stirred overnight at room temperature. Then a solution of 1N-(benzyloxycarbonyl)-1-phenyl-2-amino-ethane (from PD-6352) (385 mg, 1.5 mmol) was added and the reaction mixture was stirred for another 22 hours, then filtered and the filtrate was evaporated in vacuo. The residue was dissolved in ethyl acetate and successively washed with 7.5% citric acid solution, water, NaHCO$_3$ solution and water again. After drying over Na$_2$SO$_4$ and evaporating of the water again. After drying over Na$_2$SO$_4$ and evaporating of the solvent the residue was chromatographed on silica gel using toluene/ethanol (5%) as a eluant to isolate the product (480 mg, 58%) as a solid from n-pentane.

Step 2

A solution of carbamic acid, [2-[[2-(N-benzyloxycarbonylamino)-2-phenyl]amino]-1-methyl-2-oxo-1-(4-quinolinylmethyl)ethyl]-, tricyclo[3.3.1.1$^{3,7}$]dec-2-yl ester (480 mg, 0.73 mmol) in ethanol (25 mL) was treated with 20% palladium on carbon (150 mg, 50% water) and put under an atmosphere of hydrogen of 80 bar at room temperature with agitation. After 15 hours when no more hydrogen was seen to be taken up, the mixture was filtered over celite and concentrated in vacuo to isolate a mixture of carbamic acid, [2-[[2-amino-2-phenyl]amino]-1-methyl-2-oxo-1 -(4-quinolinylmethyl)ethyl]-, tricyclo[3.3.1.1$^{3,7}$]dec-2-yl ester (1) and carbamic acid, [2-[[2-amino-2-phenyl]amino]-1-methyl-2-oxo-1-(4-1,2,3,4-tetrahydro)-quinolinylmethyl)ethyl]-, tricyclo[3.3.1.1$^{3,7}$]dec-2-yl ester (2) and which were separated by chromatography on silica gel using ethyl acetate/methanol (3% to 55) as an eluant. Yield: Compound 1 (R$_F$=0.11, EE/-MeOH=9:1): 195 mg.

Compound 2 (R$_F$=0.17, EE/MeOH=9:1):85 mg.

Step 3

Method was as described for Example 39, Step 3, but using carbamic acid, [2-[[2-amino-2-phenyl]amino]-1-methyl-2-oxo-1-(4-quinolinyl)ethyl]-, tricyclo[3.3.1.1$^{3,7}$]dec-2-yl ester (195 mg, 0.37 μmol) from Step 2 to yield the title compound (190 mg, 82%), m.p. 120°–132° C. (D-(−)-N-methylglucamate salt).

EXAMPLE 40A

Butanoic acid,
4-[[2-[2-(1,2,3,4-tetrahydro)quinolinylmethyl]-1-oxo-2-[[(tricyclo[3.3.1.1$^{3,7}$]dec-2-yloxy)carbonyl]amino]-propyl]amino]-1-phenylethyl]-amino]-4-oxo-

Step 1

Method was as described for Example 40, Step 1, but using N-(2-adamantyloxy-carbonyl)-2-methyl-3-(quinolin-2-yl) alanine (1.42 g, 3.5 mmol) prepared in Example 34, Step 4. The crude residue was flash chromatographed on silica gel using toluene/ethanol (0.8% to 1.5%) as eluant to yield carbamic acid, [2-[[2-(N-benzyloxy-carbonyl-amino)-2-phenyl]amino]-1-methyl-2-oxo-1-(2 -quinolin-yl-methyl) ethyl]-, tricyclo[3.3.1.1$^{3,7}$]dec-2-yl ester (1.7 g, 71.3%) as a light brown solid.

Step 2

Method was as described for Example 40, Step 2, but using carbamic acid, [2-[[2-(N-benzyloxy-carbonyl-amino)-2-phenyl]amino]-1-methyl-2-oxo-1-(2-quinolinyl-methyl)ethyl]-, tricyclo[3.3.1.1$^{3,7}$]dec-2-yl ester from Step 1. The crude reaction mixture was chromatographed on silica gel using toluene/ethanol (1 to 2.5%) as eluant to yield carbamic acid, [2-[[2-amino-2-phenyl]amino]-1-methyl-2-oxo-1-(2-(1,2,3,4-tetrahydrl-)quinolinylmethyl)ethyl]-, tricyclo[3.3.1.1$^{3,7}$]dec-2-yl ester (1) (R$_F$=0.38) (0.28 g) and carbamic acid, [2-[[2-amino-2-phenyl]-amino]-1-methyl-2-oxo-1-(2-(1,2-dihydro) quinolinylmethyl)ethyl]-, tricyclo[3.3.1.1$^{3,7}$]dec-2-yl ester (2) (R$_F$=0.15) (0.50 g).

Step 3

Method was as described for Example 39, Step 3, but using carbamic acid, [2-[[2-amino-2-phenyl]amino]-1-methyl-2-oxo-1-(2-(1,2,3,4-tetrahydro)quinolinylmethyl)ethyl]-, tricyclo[3.3.1.1$^{3,7}$]dec-2-yl ester (95 mg, 0.18 mmol) from Step 2. The reaction mixture was heated to reflux for 9 hours and worked up in a usual manner. The crude residue was chromatographed on silica gel using ethyl acetate/methanol (1% to 10%) as eluant to yield the title compound (48 mg), m.p. 165°-173° C. (D-(−)-N-methylglucamate salt).

EXAMPLE 40B

Butanoic acid, 4-[[2-[2-(1,2-dihydro)quinolinylmethyl]-1-oxo-2-[[(tricyclo[3.3.1.1$^{3,7}$]dec-2-yloxy)-carbonyl]amino]-propyl]amino]-1-phenylethyl]amino]-4-oxo-

Step 1

Method was as described for Example 39, Step 3, but using carbamic acid, [2-[[2-amino-2-phenyl]amino] 1-methyl-2-oxo-1-(2-(1,2-dihydro)quinolinylmethyl)ethyl]-, tricyclo[3.3.1.1$^{3,7}$]dec-2-yl ester (95 mg, 0.18 mmol) from Example 40A, Step 2. The reaction mixture was heated to reflux for 6 hours and worked up in the usual manner to isolate the title compound (62 mg), m.p. 102°-112° C. (D-(−)-N-methylglucamate salt).

EXAMPLE 41

N-[Tricyclo[3.3.1.1$^{3,7}$]dec-2-yloxy]-2-[3-(1,3-dihydro-1-methyl-5-phenyl-2H-1,4-benzodiazepin-2-one-yl)]methyl-alanine

Step 1

A reaction mixture of 1,3-dihydro-1-methyl-5-phenyl-2H-1,4-benzodiazepin-2-one (*J. Org. Chem.* 52, 3232, (1987)) (12.6 g, 50 mmol), formaline-solution (37% in water, 75 mL) and sodium hydroxide (4.4 g, 110 mmol) was heated to reflux for 4.5 hours. Then additional formaline solution (35 mL) and sodium hydroxide (2.2 g) was added and the reaction mixture was heated for 4 hours. The cooled suspension was diluted with ethyl acetate, the organic layer separated, washed with water and dried over Na$_2$SO$_4$. The organic solution was evaporated in vacuum and the residue flash-chromatographed on silica gel using toluene/ethanol (3.5%) as eluant to give 1,3-dihydro-3-hydroxymethyl-1-methyl-5-phenyl-2H-1,4-benzodiazepin-2-one (2.15 g, 15%).

Step 2

1,3-dihydro-3-hydroymethyl-1-methyl-5-phenyl-2H-1,4-benzodiazepin-2-one (980 mg, 3.5 mmol) was dissolved in methylene chloride and thionylchloride (1.65 g, 14 mmol) was added in portions. The reaction mixture was heated to reflux for 3 hours and then allowed to cool to room temperature overnight. The reaction mixture was evaporated in vacuum, dissolved in methylene chloride and the organic solution was basified with aqueous NaHCO$_3$ in water. The organic layer was separated, dried over Na$_2$SO$_4$ and evaporated in vacuum to give crude 1,3-dihydro-3-chloromethyl-1-methyl-5-phenyl-2H-1,4-benzodiazepin-2-one (1.1 g) which was used for the next step.

Step 3

Synthetic method was as described for Example 32, Step 2, but using 1,3-dihydro-3-chloromethyl-1-methyl-5-phenyl-2H-1,4-benzodiazepin-2-one (1.0 g, 3.5 mmol) from Step 2. The crude residue was chromatographed on silica gel (flash) using ethyl acetate:ethanol (3.5%) as eluant to obtain 2-[3-(1,3-dihydro-1-methyl-5-phenyl-2H-1,4-benzodiazepin-2-one-yl) methyl-alanine methylester (460 mg, 36%).

Step 4

Method was as described for Example 30, Step 4, but using 2-[3-(1,3-dihydro-1-methyl-5-phenyl-2H-1,4-benzodiazepin-2-one-yl) methyl-alanine methylester (770 mg, 2.1 mmol) to obtain N-(adamantyloxycarbonyl-2-[3-(1,3-dihydro-1-methyl-5-phenyl-2H-1,4-benzodiazepin-2-one-yl)]methyl-alanine methylester (1.2 g, 100%) as a light yellow foam.

Step 5

Method was as described for Example 30, Step 5, but using the ester synthesized in Step 4 this example. After working up in the usual manner N-(adamantyloxycarbonyl-2-[3-(1,3-dihydro-1-methyl-5-phenyl-2H-1,4-benzodiazepin-2-one-yl)]methylalanine (1.2 g, 100%) was isolated as a yellow solid.

EXAMPLE 42

Carbamic acid [1-(1H-indazol-3-ylmethyl)-1-methyl-2-oxo-2-(2-phenylethyl)aminoethyl]tricyclo[3.3.1.1$^{3,7}$]dec-2-yl ester, (±)-

To a solution of racemic N-[(2-adamantyloxy)-carbonyl]- 3-(1H-indazol-3-yl)-2-methyl-alanine (0.45 g, 1.1 mmol) in dry THF (20 mL) was added 1,1′-carbonyldiimidazole (0.18 g, 1.1 mmol) and stirred for 1 hour. To this mixture was added dropwise a solution of 2-phenethylamine (0.24 g, 2.0 mmol) in dry THF (5 mL) and the resultant mixture left stirring for 3 hours. After removing the solvent in vacuo the residue was partitioned between water (20 mL) and CH$_2$Cl$_2$ (30 mL). The organic phase was dried over MgSO$_4$ and the solvent evaporated. The residue was purified by chromatography over silica gel using MeOH:CH$_2$Cl$_2$ 2:98 (v/v) as eluant to give the title compound (0.14 g, 25%) as a colorless amorphous solid, m.p. 86°-87° C.

Intermediate

Racemic N-[(2-Adamantyloxy)carbonyl]-3-(1H-indazol-3-yl)-2-methyl-alanine

Route A, Step 1

Racemic 3-(1H-indazol-3-yl)-2-methyl-alanine methyl ester

To a stirred suspension of sodium hydride (0.60 g, 20 mmol, 80% in paraffin oil) in dry DMSO (20 mL) was added dropwise a solution of N-(phenylmethylene)-DL-alanine methyl ester (3.82 g, 20 mmol) in dry DMSO (15 mL) under nitrogen and stirred for 1 hour. The reaction mixture was then cooled to 10° C. and a solution of methiodide of 3-dimethylaminomethylindazolo (H. R. Snyder, Crayton B. Thompson, and R. L. Hinman, *J. Am. Chem. Soc*, 74, 2009 (1952)) (6.4 g, 20 mmol) in dry DMSO (40 mL) was added in one portion and the resultant mixture left stirring for 24 hours at room temperature. After removing the solvent in vacuo the residue was partitioned between water (30 mL) and CH$_2$Cl$_2$ (200 mL). The organic phase was dried over MgSO$_4$ and the solvent evaporated. The residue was stirred with ethyl ether (2×250 mL) until forming of a fine precipitate. This was removed by filtration and the filtrate evaporated. The resulting oil was stirred for 4 hours with 1N hydrochloric acid (20 mL) and ethyl ether (20 mL), the aqueous phase was made basic with potassium carbonate, extracted with CH$_2$Cl$_2$ and dried over MgSO$_4$. After removing the solvent in vacuo, the residue was chromatographed over silica gel using MeOH/CH$_2$Cl$_2$ 2:98, then MeOH:CH$_2$Cl$_2$ 5:95 (v/v) as eluants to yield the required compound (0.45 g, 10%) as a yellow oil which solidified upon standing. IR (KBr) 1729 cm$^{-1}$. NMR (CDCl$_3$), δ 1.50 (3H, s) , 2.20 (2H, br.s), 3.25 (1H, d, J=15.0 Hz), 3.55 (1H, d, J=15. Hz), 3.60 (3H, s), 7.10–7.68 (4H, m), 10.5 (1H, br.s).

Step 2

Racemic N-[(2-Adamantyloxy)carbonyl]-3-[[1-(2-adamantyloxy)carbonyl]-1H-indazol-3-yl]-2-methyl-alanine methyl ester To a stirred solution of 2-adamantyl chloroformate (0.60 g, 2.8 mmol) in dry THF (10 mL) was added a solution of compound of Step 1 (0.46 g, 2.0 mmol) in dry THF (20 mL) followed by a solution of triethylamine (0.51 g, 5.0 mmol) in dry THF (10 mL) dropwise. After 4 hours, the reaction mixture was filtered, the solvent removed in vacuo and the residue chromatographed over silica gel using MeOH:CH$_2$Cl$_2$ 2:98 (v/v) as eluant to provide 0.80 g (73%) of product as a colorless amorphous solid, m.p. 79°–82° C. MS (70 ev):m/z 589 (H*, 7.89), 135 (100).

Step 3

To a solution of compound of Step 2 (0.80 g, 1.4 mmol) in a mixture of 1.4-dioxan (20 mL) and water (8 mL) was added LiOH (0.30 g, 12.5 mmol) and stirred for 48 hours. After removing the solvent in vacuo the residue was partitioned between water (30 mL) and ethyl ether (30 mL) and stirred. The clear water phase was separated, acidified with 1M citric acid solution to pH 4.5, and extracted with ethyl acetate. The organic phase was dried over MgSO$_4$ and evaporated in vacuo to yield the title compound (0.48 g, 87%) as an amorphous solid, sintering at 140° C., used without further purification.

Route B

Step 1

1-(4-Methylphenyl)sulfonyl-1H-indazole-3-carboxylic acid methyl ester

To a suspension of sodium hydride (4.6 g, 150 mmol, 80% in paraffin oil) in dry THF (100 mL), a solution of 3-indazolecarboxylic acid methyl ester [(J. Am. Chem. soc, 74, 2009 (1952)] (22.0 g, 125 mmol) in dry THF (100 mL) was added dropwise with stirring while the inner temperature was maintained under 30° C. The reaction mixture was stirred for 30 minutes and then a solution of p-toluenesulphonyl chloride (28.0 g, 150 mmol) in dry THE (100 mL) was added dropwise to the stirring reactant. After 4 hours, the solvent was evaporated in vacuo and the residue partitioned between water and CH$_2$Cl$_2$. The organic phase was separated, dried over Na$_2$SO$_4$ and the solvent evaporated to leave a solid which was recrystallized from ethyl acetate (31.0 g, 75%), m.p. 163°–165° C.

Step 2

3-Hydroxymethyl-1-(4-methylphenyl)sulfonyl-1H-indazole

To a stirred suspension of ester of Step 1 (31.0 g, 94 mmol) in dry THF (600 mL) cooled at 5° C. and under nitrogen was added dropwise and at this temperature a solution of Red-A1 (sodium dihydro-bis (2-methoxyethoxy)aluminate—70% in toluene) (34 mL, 114 mmol) in dry THF (30 mL). After stirring 2 hours at 5° C., and then 1 hour at room temperature the mixture was cooled at 10° C. and treated dropwise with 2N NaOH (100 mL) to effect hydrolysis of the intermediate complex. The organic phase was separated and the solvent in vacuo evaporated. The residue was chromatographed over silica gel using MeOH/CH$_2$Cl$_2$ 5:95 (v/v) as eluant to give the required alcohol (13.5 g, 54%) as a yellow oil which solidified upon standing, m.p. 95°–98° C.

Step 3

3-Chloromethyl-1-(4-methylphenyl)sulfonyl]-1H-indazole

To a stirred suspension of the alcohol from Step 2 (12.0 g, 40 mmol) in dry toluene (100 mL) was added dropwise SOCl$_2$ (15 mL) and the mixture was heated at 75°–80° C. for 30 minutes. Excess SOCl$_2$ and the solvent were removed in vacuo and the residue triturated with ethyl ether (50 mL) to give the desired product (9.5 g, 74%) as a beige crystalline solid, m.p. 150°–153° C.

Step 4

Racemic 2-Methyl-3-[[1-(4-methylphenyl)sulfonyl]-1H-indazol-3-yl]-alanine methyl ester To a stirred suspension of sodium hydride (0.60 g, 20 mmol, 80% in paraffin oil) in dry DMSO (20 mL) was added dropwise a solution of N-(phenylmethylene)-DL-alanine methyl ester (3.82 g, 20 mmol) in dry DMSO (20 mL) under nitrogen and stirred for 1 hour. The reaction mixture was then cooled to 10° C. and a solution of the compound from Step 3 (5.78 g, 18 mmol) in dry DMSO (100 mL) was added in one portion and the resultant mixture left stirring for 24 hours at room temperature. After removing the solvent in vacuo the residue was partitioned between water (30 mL) and CH$_2$Cl$_2$ (200 mL). The organic extract was dried (Na$_2$SO$_4$) and evaporated. The resulting oil was stirred for 4 hours with 1N hydrochloric acid (50 mL) and ethyl ether (50 mL), the aqueous phase was separated, made basic with potassium carbonate, extracted with CH$_2$Cl$_2$ and dried (Na$_2$SO$_4$). After removing the solvent in vacuo, the residue was purified by chromatography over silica using MeOH/CH$_2$Cl$_2$ 2:98 (v/v) as eluant to give the desired compound (5.5 g, 79%) as a yellow oil which solidified upon standing. IR (film) 1736 cm$^{-1}$.

Step 5

Racemic N-[(2-Adamantyloxy)carbonyl]-2-methyl-3-[[1-(4-methylphenyl)sulfonyl]-1H-indazol-3-yl]-alanine methyl ester To a stirred solution of 2-adamantyl chloroformate (6.4 g, 30 mmol) in dry THF (15 mL) was added a solution of compound of Step 4 (8.9 g, 23 mmol) in dry THF (100 mL) followed by a solution of triethylamine (6.1 g, 56 mmol) in dry THF (15 mL) dropwise. After 1 hour, the reaction mixture was filtered, the solvent removed in vacuo, and the residue triturated with ethyl ether to give the desired compound (9.2 g, 71% ) as a white solid, m.p. 136°–138° C.

Step 6

A stirred mixture of the ester from Step 5 (4.96 g, 8.8 mmol), dioxan (100 mL), KOH (5.0 g), and water (50 mL) was heated at 75°–80° C. for 8 hours. After removing the solvents in vacuo the residue was dissolved in water (125 mL), the clear water solution acidified with 1M citric acid solution to pH 4.5 and extracted with $CH_2Cl_2$. The organic extract was dried over $Na_2SO_4$, evaporated in vacuo, and the residue triturated with petroleum ether to give the title compound (3.2 g, 91%) as a colorless amorphous solid, sintering at 139° C.

EXAMPLE 43

Carbamic acid, [2-[1-(hydroxymethyl)-2-phenylethyl]amino-1-(1H-indazo-1-3-yl-methyl)-1-methyl-2-oxo]ethyl-, tricyclo[3.3.1.1$^{3,7}$]dec-2-yl ester (hydroxymethyl center is S, other center is RS)

To a solution of racemic N-[(2-adamantyloxy)carbonyl]-3-(1H-indazol-3-yl)-2-methylalanine (0.36 g, 0.9 mmol) in dry THF (20 mL) was added 1,1'-carbonyldiiimidazole (0.18 g, 1.0 mmol) and stirred for 1 hour. To this mixture was added dropwise a solution of (S)-(−)-2-amino-3-phenyl-1-propanol (0.15 g, 1.0 mmol) in dry THF (10 mL) and the resultant mixture left stirring for 12 hours. After removing the solvent in vacuo, the residue was partitioned between water (20 mL) and $CH_2Cl_2$ (40 mL). The organic phase was dried over $MgSO_4$ and the solvent evaporated. The residue was subjected to silica gel chromatography using ethyl acetate as eluant to give the title compound (0.20 g, 42%) as a colorless, amorphous solid and a mixture of two diastereomers, m.p. 80°–85° C.

EXAMPLE 44

4-[[2-[3-(1H-indazol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid benzyl ester (mixture of isomers)

Method was as described for Example 43 above but instead using 4-[[(2-amino-1-phenyl)ethyl]amino]-4-oxobutanoic acid benzyl ester as amine. The crude residue was chromatographed over silica gel using MeOH:$CH_2Cl_2$ 0.5–1/99.5–99 (v/v) as eluant to give the title compound (100 mg, 6%) as a colorless gum, the compounds of Example 46 (see Scheme X, compound 13d) and the benzyl ester of the starting carboxylic acid. MS (70 ev): m/e (DCI:$CH_4$) 708 (M+H)$^+$; Rf=0.35 (MeOH/$CH_2Cl_2$ 1:9).

EXAMPLE 45

4-[[2-[3-(1H-indazol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid (mixture of isomers)

A solution of benzyl ester of Example 44 (0.080 g, 0.12 mmol) in absolute ethanol (10 mL) was treated with 20% Pd(OH)$_2$ on carbon and placed under an atmosphere of hydrogen at 25° C. for 15 hours. The reactions mixture was then filtered and the filtrate concentrated in vacuo to give the desired compound (35 mg, 52%) as an amorphous solid and a mixture of two diastereomers, m.p. 108°–122° C.; IR (KBr) 1698 and 1659 cm$^{-1}$; MS (70 ev): m/e (DCI-$NH_2$) 614 (M−1)$^+$.

EXAMPLES 46A AND 46B

Tricyclo[3.3.1.1$^{3,7}$]dec-2-yl-(R or S,R)-[2-[[2-(2,5-dioxo-1-pyrrolidinyl)-2-phenylethy]amino]-1-(1H indazol-3-ylmethyl]-1-methyl-2-oxoethyl]carbamate and Tricyclo[3.3.1.1$^{3,7}$]dec-2-yl-(S or R,R)-[2-[[2-(2,5-dioxo-1-pyrrolidinyl)-2-phenylethyl]amino]-1-(1H -indazol-3-ylmethyl)-1-methyl-2-oxoethyl]carbamate The compounds were isolated by chromatographic separation of the crude residue of Example 44.

Diastereomer 1 (46A): (160 mg, 10%) white amorphous solid, m.p. 101°–108° C. MS (70 ev):m/z (DCI+$NH_3$) 598 (M+H)$^+$; Rf=0.45 (MeOH/$CH_2Cl_2$ 1:9).

Diastereomer 2 (46B): (65 mg, 6.5%) white amorphous solid, m.p. 128°–130° C. MS (70 ev):m/z (DCI+$NH_3$) 598 (M+H)$^+$; RF=0.42 (MeOH/$CH_2Cl_2$ 1:9).

EXAMPLE 47

Tricyclo[3.3.1.1$^{3,7}$]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*), 2R*]] and [1S-[1R*(S*), 2R*]] isomers)

Step A: Preparation of methyl α-methyl-N-[(tricyclo[3.3.1.1$^{3,7}$]dec-2-yloxy)carbonyl]-DL-tyrosinate To a solution of tricyclo[3.3.1.1$^{3,7}$]dec-2-yl carbonchloridate [5.77 g, 0.026 mmol, prepared from 2-adamantanol and fis (trichloromethyl)carbonate (Horwell, D. C., et al, *J. Med. Chem.* 1991, 34, 404–414)] in 60 mL THF, a solution of DL-α-methyltyrosine methyl ester (5.0 g, 0.0238 mol, prepared from the DL-α-methyltyrosine methyl ester hydrochloride using 1M $K_2CO_3$ and EtOAc) in 320 mL THF was added dropwise via an addition funnel, keeping the temperature below 25° C. A solution of triethylamine (4.81 g, 0.047 mol) in 120 mL THF was then added dropwise and the heterogeneous reaction mixture was stirred for 16 hours at room temperature under a nitrogen atmosphere. The amine salt was filtered and the filtrate was concentrated in vacuo to give a tan, fluffy solid. Purification by flash chromatography (silica gel, 10% EtOAc/hexane) yielded the title compound. MS: 388 (MH+); 387 (M+).

Step B

Preparation of methyl α-methyl-O-(phenylmethyl)-N-[(tricyclo[3.3.1.1$^{3,7}$]dec-2-yloxy)carbonyl]-DL-tyrosinate To a solution of methyl α-methyl-N-[(tricyclo[3.3.1.1$^{3,7}$]dec-2-yloxy)carbonyl]-D,L-tyrosinate (1.0 g, 0.0025 mmol) in 12.5 mL acetonitrile, potassium carbonate (0.51 g, 0.0038 mol, 1.5 eq) was added, followed by the addition of benzyl chloride (0.49 g, 0.0038 mol, 1.5 eq). This reaction mixture was then heated to reflux for 6 hours under a nitrogen atmosphere. After cooling to room temperature, the reaction mixture was concentrated in vacuo to give a tan residue. The residue was diluted with water and ethyl acetate. The layers were separated and the aqueous layer was extracted two times with ethyl acetate. The combined organic layers were washed with brine, dried ($Na_2SO_4$), and concentrated in vacuo to yield the desired product in quantitative yield. MS: 478.1 (MH+).

Step C

Preparation of
α-methyl-O-(phenylmethyl)-N-[(tricyclo[3.3.1.1$^{3,7}$]dec-2-yloxy)carbonyl]-DL-tyrosine To a stirred solution of methyl α-methyl-O-(phenylmethyl)-N-[(tricyclo[3.3.1.1$^{3,7}$]dec-2-yloxy)-carbonyl]-DL-tyrosinate (1.10 g, 0.0023 mol) in 8.8 mL dioxane and 4.4 mL water, lithium hydroxide monohydrate (0.145 g, 0.003 mmol, 1.5 eq) was added. This reaction mixture was then stirred for 48 hours at room temperature. The reaction mixture was then concentrated in vacuo and the resulting white syrup was diluted with 20 mL H$_2$O. This basic solution (pH 13) was then acidified (pH 2) with 1 mL 10% HCl, upon which white solid precipitated. This acidified aqueous suspension was then extracted three times each with ether. The combined organic layers were dried (Na$_2$SO$_4$) and concentrated in vacuo to give the desired product (0.78 g, 0.0016 mmol, 73%). MS: 464.3 (MH+); 463.3 (M+).

Step D

Preparation of
Tricyclo[3.3.1.1$^{3,7}$]dec-2-yl[2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers)

To a solution of α-methyl-O-(phenylmethyl)-N-[(tricyclo[3.3.1.1$^{3,7}$]dec-2-yloxy)carbonyl]-DL-tyrosine (300 mg, 0.647 mmol) in 10 mL ethyl acetate, 1-hydroxybenzotriazole (96.2 mg, 0.71 mmol, 1.1 eq) was added followed by the addition of N,N'-dicyclohexylcarbodiimide (160 mg, 0.77 mmol, 1.2 eq). This turbid mixture was then stirred for 3 hours at room temperature under a nitrogen atmosphere. The white solid (dicyclohexyl urea) was filtered off and to the clear filtrate was added a warm solution of (1S, 2S)-(+)-2-amino-1-phenyl-1,3-propanediol (150 mg, 0.90 mmol, 1.4 eq) in 10 mL ethyl acetate. Upon addition of this diol, a white solid precipitated out of solution immediately. This white heterogeneous mixture was stirred for 16 hours at room temperature under a nitrogen atmosphere. The white solid was filtered and the mother liquor was concentrated in vacuo to give a crude oil. Purification by flash chromatography (silica gel, 75% EtOAc/hexane) yielded the title compound (151.6 mg, 0.247 mmol, 38.2%).

Analysis for C$_{37}$H$_{44}$N$_2$O$_6$.2 mmol H$_2$O: Calcd: C, 68.49; H, 7.45; N, 4.31. Found: C, 68.15; H, 6.94; N, 4.27. MS: 613.5 (MH+).

EXAMPLE 48

Tricyclo[3.3.1.1$^{3,7}$]dec-2-yl
[2-[[2.hydroxyl-1-(hydroxymethyl)-2-phenylethyl]amino]-1-[(4-hydroxyphenyl)-methyl]-1-methyl-2-oxoethyl]carbamate (Mixture of [1S-[1R8(R*),2R*]] and [1S-[1R8(S*),2R*]] isomers)

Step A

Preparation of
α-methyl-N-[(tricyclo3.3.1.1$^{3,7}$]dec-2-yloxy)carbonyl]-DL-tyrosine The title compound was prepared from methyl α-methyl-N-[(tricyclo[3.3.1.1$^{3,7}$]dec-2-yloxy)carbonyl]-DL-tyrosinate (482 mg, 1.24 mmol, prepared using the procedure described in Example 47, Step A) and lithium hydroxide monohydrate (156.6 mg, 3.72 mmol) using the procedure described in Example 1, Step C.

Analysis for C$_{21}$H$_{27}$NO$_5$.0.75 mol H$_2$O: Calcd: C, 65.18; H, 7.42; N, 3.61. Found: C, 65.17; H, 7.63; N, 3.44. MS: 374 (MH+), 373 (M+).

Step B

Preparation of Tricyclo[3.3.1.1$^{3,7}$]dec-2-yl
[2-[[2-hydroxy-1-(hydroxymethyl)-2-phenylethyl]amino]-1-[(4-hydroxypheny)methyl]-1-methyl-2-oxoethyl]carbamate (Mixture of [1S-[1R*(R*),2R*]] and [1S-[1R*(S*),2R*]] isomers)

The title compound was prepared from α-methyl-N-[(tricyclo[3.3.1.1$^{3,7}$]dec-2-yloxy)carbonyl]-DL-tyrosine (250 mg, 0.669 mmol), 1-hydroxybenzotriazole (156.7 mg, 0.937 mmol), N,N'-dicyclohexylcarbodiimide (165.6 mg, 0.802 mmol), and (1S,2S)-(+)-2-amino-1-phenyl-1,3-propanediol (156.7 mg, 0.937 mmol) using the procedure described in Example 47, Step D. Purification by flash chromatography (silica gel, 100% EtOAc) yielded the title compound (124.5 mg, 0.238 mmol, 35.5%).

Analysis for C$_{30}$H$_{38}$N$_2$O$_6$.1.9 mol EtOAc: Calcd: C, 65.42; H, 7.76; N, 4.08. Found: C, 65.76; H, 7.77; N, 4.41. MS: 523.3 MH+).

EXAMPLE 49

Tricyclo[3.3.1.1$^{3,7}$]dec-2-yl[2-[[2-hydroxyl-1-(hydroxymethyl)-2-phenylethyl]amino]-1-[(4-methoxyphenyl)-methyl]-1-methyl-2-oxoethyl]carbamate (Mixture of [1S-[1R*(R*),2R*)]] and [1S-[1R*(S*),2R*]] isomers)

Step A

Preparation of methyl
O,α-dimethyl-N-[(tricyclo[3.3.1.1$^{3,7}$]dec-2-yloxy)carbonyl]-DL-tyrosinate The title compound was prepared from methyl α-methyl-N-[(tricyclo[3.3.1.1$^{3,7}$]dec-2-yloxy)carbonyl]-DL-tyrosinate (0.671 g, 0.0017 mol, prepared using the procedure described in Example 47, Step A), potassium carbonate (0.345 g, 0.0025 mol) and iodomethane (0.368 g, 0.0025 mol) using the procedure described in Example 47, Step B. MS: 402.4 (MH+).

Step B

Preparation of
O,α-dimethyl-N-[(tricyclo[3.3.1.1$^{3,7}$]dec-2-yloxy)carbonyl]-DL-tyrosine The title compound was prepared from methyl O,α-dimethyl-N-[(tricyclo[3.3.1.1$^{3,7}$]dec-2-yloxy)carbonyl]-DL-tyrosinate (0.40 g, 0.001 mol) and lithium hydroxide monohydrate (0.066 g, 0.001 mol, 1.5 eq) using the procedure described in Example 47, Step C. MS: 388.0 (MH+); 387.0 (M+).

Step C

Preparation of
Tricyclo[3.3.1.1$^{3,7}$]dec-2-yl[2-[[2-hydroxy-1-(hydroxymethyl)-2-phenylethyl]amino]-1-[(4-methoxyphenyl)methyl]-1-methyl-2-oxoethyl]carbamate (Mixture of [1S-[1R*(R*),2R*] and [1S-[1R*(S*),2R*]] isomers)

The title compound was prepared from O,α-dimethyl-N-[(tricyclo[3.3.1.1$^{3,7}$]dec-2-yloxy)carbonyl]-DL-tyrosine (250 mg, 0. 645 mmol), 1-hydroxybenzotriazole (95 mg, 0.709 mmol), N,N'-dicyclohexylcarbodiimide (160 mg, 0.774 mmol) and (1S, 2S)-(+)-2-amino-1-phenyl-1,3-propanediol (151 mg, 0.903 mmol) using the procedure described in Example 47, Step D. Purification by flash chromatography (silica gel, 75% EtOAc/hexane) yielded the title compound (190 mg, 0.354 mmol, 55%).

Analysis for $C_{31}H_{40}N_2O_6 \cdot 0.5$ mol $H_2O$: Calcd: C, 67.51; H, 7.74; N, 5.25. Found: C, 67.73; H, 7.57; N, 5.12. MS: 537.2 (MH+).

EXAMPLE 50

Tricyclo[3.3.1.1$^{3,7}$]dec-1-yl [2-[[2-hydroxy-1-(hydroxymethyl)-2-phenylethyl]amino]-1-methyl-2-oxo-1-[[4-(phenylmethoxy)phen/yl]methyl]ethyl]carbamate (Mixture of [1S-[1R*(R*),2R*]] and [1S-[1R*(S*),2R*]] isomers)

Step A

Preparation of methyl α-methyl-N-[(tricyclo[3.3.1.1$^{3,7}$]dec-1-yloxy)carbonyl]-DL-tyrosinate The title compound was prepared from tricyclo[3.3.1.1$^{3,7}$]dec-1-ylcarbonofluoridate (1.36 g, 0.0068 mol) and D,L-α-methyltyrosine methyl ester (1.50 g, 0.006 mol) using the procedure described in Example 47, Step A. MS: 388 (MH+); 387 (M+).

Step B

Preparation of methyl α-methyl-O-(phenylmethyl)-N-[(triyclo[3.3.1.1$^{3,7}$]dec-1-yloxy)carbonyl]DL-tyrosinate The title compound was prepared from methyl α-methyl-N-[(tricyclo[3.3.1.1$^{3,7}$]dec-1-yloxy)carbonyl]-DL-tyrosinate (0.97 g, 0.002 mol), potassium carbonate (0.35 g, 0.0025 mol), and benzyl chloride (0.475 g, 0.003 mol) using the procedure described in Example 1, Step B. MS: 478.3 (MH+); 477.2 (M+).

Step C

Preparation of α-methyl-O-(phenylmethyl)-N-[(tricyclo[3.3.1.1$^{3,7}$]dec-1-yloxy)carbonyl]-DL-tyrosine The title compound was prepared from methyl α-methyl-O-(phenylmethyl)-N-[(tricyclo[3.3.1.1$^{3,7}$]dec-1-yloxy)carbonyl]-DL-tyrosine (200 mg, 0.418 mmol) and lithium hydroxide monohydrate (26.3 mg, 0.628 mmol, 1.5 eq) using the procedure described in Example 47, Step C.

Step D

Preparation of Tricyclo[3.3.1.1$^{3,7}$]dec-1-yl [2-[[2-hydroxy, 1-(hydroxymethyl)]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers)

The title compound was prepared from α-methyl-O-(phenylmethyl)-N-[(tricyclo[3.3.1.1$^{3,7}$]dec-1-yloxy)-carbonyl]-DL-tyrosine (92.8 mg, 0.20 mmol), 1-hydroxybenzotriazole (28.6 mg, 0.21 mmol), N,N[-dicyclohexylcarbodiimide (46.6 mg, 0.22 mmol) and (1S,2S)-(+)-2-amino-1-phenyl-1,3-propanediol (33.4 mg, 0.20 mmol) using the procedure described in Example 47, Step D.

Analysis for $C_{37}H_{44}N_2O_6 \cdot 4$ mol $H_2O$: Calcd: C, 64.89; H, 7.65; N, 4.09. Found: C, 65.25; H, 7.57; N, 4.16. MS: 613.2 (MH+).

Alkylation Procedure (See Examples 51–57)

A solution of PhCh=N—CH(CH$_3$)CO$_2$CH$_3$ (50 mmol) in THF (150 mL) was added to a stirred solution of LDA (55 mmol) in THF at −78° C. The resulting yellow anion was further treated with a solution of the alkyl halide (ArCH$_2$) (50 mmol) and the resulting mixture allowed to stir overnight. Following removal of volatile materials the viscous residue was treated with 1N HCl solution (100 mmol) and stirred rapidly for 1 to 2 hours. Benzaldehyde was removed by extraction with ether and the aqueous phase made alkaline using 10% aqueous sodium bicarbonate solution. The amino ester

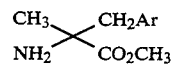

was extracted into ether, the organic phase dried (MgSO$_4$) and evaporated, leaving the crude product which was carried on without purification.

A solution of the desired amino ester (2 mmol) in dry THF (20 mL) was treated with 2-AdocCl (2.2 mmol) followed by the dropwise addition of triethylamine (2.2 mmol). The mixture was stirred for 4 hours at room temperature. Volatile material was removed under vacuum and the residue partitioned between ethyl acetate and water. The organic layer was washed with dilute aqueous citric acid solution followed by dilute sodium bicarbonate solution, then saline solution. After drying the solution (MgSO$_4$), the solvent was removed, leaving the crude protected ester.

Using 4-(chloromethyl)-3,5-dimethyl-isoxazole as the alkylating agent, the product was isolated after chromatography on silica gel using ethyl acetate/CH$_2$Cl$_2$/hexane 1/1/2 as eluant in 36% yield. NMR (CDCl$_3$) δ 1.46–2.05 (17H, m), 2.17 (3H, s), 2.29 (3H, s), 3.07 (2H, s), 3.77 (3H, s), 4.8 (1H, s), 5.25 (1H, s).

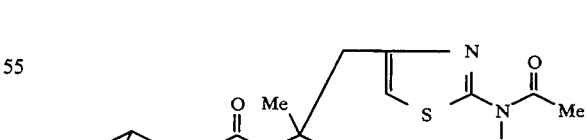

Using 2-acetamido-4-(chloromethyl)thiazole as the alkylating agent and 2 equivalents of the imine anion, the methyl ester was isolated in 41% yield after flash chromatography using CH$_2$Cl$_2$/MeOH 95/5 as eluant. NMR (CDCl$_3$) δ 1.45–2.05 (17H, m), 2.31 (3H, s), 3.15

(2H, m), 3.75 (3H, s), 4.75–4.85 (1H, m), 5.70–5.90 (1H, m), 6.63 (1H, s).

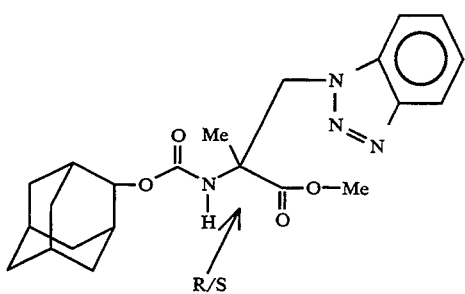

Using 1-chloromethylbenzotriazole as the alkylating agent, the methyl ester was isolated after chromatography on silica gel using CH$_2$Cl$_2$/MeOH 99.5/0.5 as eluant in 71% yield. NMR (CDCl$_3$) δ 1.35–2.10 (14H, m), 3.88 (3H, s), 4.75–4.85 (1H, m), 5.25–5.40 (3H, m), 7.25–7.50 (2H, m), 7.55 (1H, d), 8.05 (1H, d).

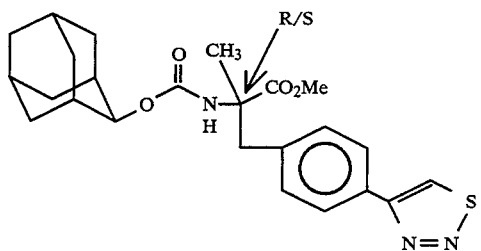

Using 4-(4-bromomethylphenyl-1,2,3-thiadiazole as alkylating agent, the product was isolated in 27% overall yield after chromatography (silica gel, 10% EtOAc-hexane) as a white foam. NMR (CDCl$_3$) δ 1.5–2.09 (17H, mult), 3.2–3.75 (4H, mult), 3.78 (3H, s), 4.8 (1H, broad singlet), 5.4 (1H, broad singlet), 7.2 (2H, doublet), 7.9 (2H, doublet), 8.6 (1H, singlet).

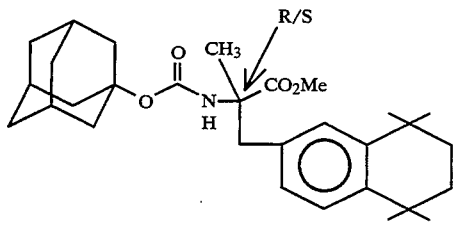

Using 7-chloromethy-1,1,4,4-tetramethyltetrahydro naphthalene as alkylating agent, the product was isolated in 28% overall yield after chromatography (silica gel, 10% EtOAc/hexane) as a clear glass. NMR (CDCl$_3$) δ 1.24 (6H, s), 1.25 (6H, s), 1.61–2.05 (19H, m), 3.18–3.3 (2H, m), 3.78 (3H, s), 4.86 (1H, broad singlet), 5.41 (1H, broad singlet), 6.79–7.19 (4H, m).

Saponification—coupling

The methyl ester (9 mmol) dissolved in dioxane (15 mL) and a 1N solution of lithium hydroxide was added (10 mmol). When TLC revealed completion of the reaction, the solvent was removed and the residue suspended between ethyl acetate and dilute aqueous citric acid solution. The organic layer was removed, washed once with water, dried, and evaporated to give the crude acid which was carried on without further purification.

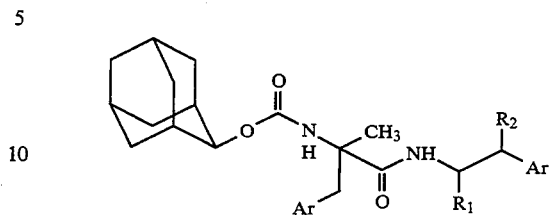

To a solution of the acid (0.45 mmol) in CH$_2$Cl$_2$ (10 mL) is added 1-(3-dimethylaminopropyl)-3-ethylcarbodiimide hydrochloride (0.5 mmol), triethylamine (0.5 mmol), and 1-hydroxybenzotriazole hydrate (0.6 mmol). The resulting mixture is stirred 2 hours at room temperature before (S)-(−)-2-amino-3-phenyl-1-propanol or (1S,2S)-(+)-2-amino-1-phenyl-1,3-propanediol or phenethyl amine (0.5 mmol) is added in one portion. The resulting mixture is stirred overnight at room temperature.

Workup A: The mixture is concentrated and the residue dissolved in chloroform and placed on a flash silica gel column. Elution with the appropriate solvent gave the pure desired product.

Workup B: The reaction is poured into CH$_2$Cl$_2$/H$_2$O and the aqueous layer extracted 2×CH$_2$Cl$_2$. The combined organic extracts are washed with saturated NaHCO$_3$, dried over MgSO$_4$, and concentrated in vacuo.

EXAMPLE 51

Tricyclo[3.3.1.1$^{3,7}$]dec-2-yl (±)-[1-[(3,5-dimethyl-4-isoxazolyl)methyl]-1-methyl-2-oxo-2-[(2-phenylethyl)amino]ethyl]carbamate

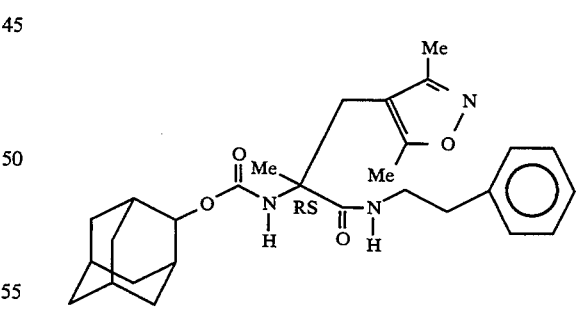

Using phenethylamine and Workup B in the coupling afforded a 71% yield of a solid after flash chromatography using CH$_2$Cl$_2$/MeOH 98/2 as eluant, m.p. 70°–73° C. Parent 508. IR (cm$^{-1}$) (CHCl$_3$) 3407, 3313, 3004, 2998, 1715, 1674, 1629, 1603, 1491. NMR (CDCl$_3$) δ 1.34 (3H, s), 1.35–2.01 (14H, m), 2.16 (3H, s), 2.27 (3H, s), 2.81 (2H, t), 2.90 (1H, d), 3.11 (1H, D), 3.53 (2H, M), 4.81 (1H, M), 4.85–5.20 (1H, m), 6.11 (1H, t), 7.15–7.31 (5H, m).

EXAMPLE 52

Tricyclo[3.3.1.1$^{3,7}$]dec-2-yl
(±)-[1-[[2-(acetylamino)-4-thiazolyl]methyl]-1-methyl-2-oxo-2-[(2-phenylethyl)amino]ethyl]carbamate

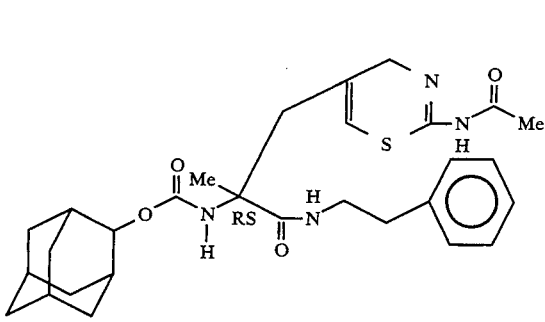

Using phenethylamine and Workup B in the coupling afforded a 35% yield of a white solid after flash chromatography using CH$_2$Cl$_2$/MeOH 98/2 as eluant. m.p. 93°–97° C. Mass spec (EI) parent 525. IR (cm$^{-1}$) (KBr) 3464, 3460, 2998, 1716, 1700, 1695, 1617, 1603, 1575. NMR (CDCl$_3$) δ 1.49 (3H, s), 1.49–2.00 (14H, m), 2.25 (3H, s), 2.50–2.85 (2H, m), 2.85–3.65 (5H, m), 4.77 (1H, s), 6.61 (1H, s), 6.60–7.00 (1H, m), 7.15–7.28 (5H, m).

EXAMPLE 53

Tricyclo[3.3.1.1$^{3,7}$]dec-2-yl
(±)-[1-(1H-benzotriazol-1-ylmethyl)-1-methyl-2-oxo-2-[(2-phenylethyl)amino]ethyl]carbamate

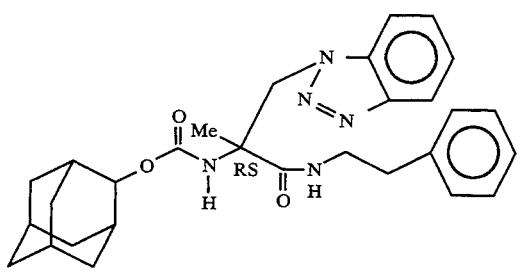

Using phenethylamine and Workup B in the coupling afforded a 10% yield of a solid after flash chromatography using 99/1 CH$_2$Cl$_2$/MeOH as eluant, m.p. 180°–185° C. Mass spec (EI) parent 501. IR (cm$^{-1}$) (CHCl$_3$) 2983, 2968, 1733, 1717, 1700, 1647. NMR (CDCl$_3$) δ 1.51 (3H, s), 1.35–2.05 (14H, m), 2.50–2.85 (2H, m), 3.46 (2H, q), 4.78 (1H, s), 5.00 (1H, d), 5.34 (1H, d), 5.37 (1H, s), 6.40 (1H, m), 7.09–7.62 (8H, m), 8.04 (1H, d).

EXAMPLE 54

Tricyclo[3.3.1.1$^{3,7}$]dec-2-yl (RS, S)
[2-[[1-(hydroxymethyl)-2-phenylethyl]amino]-1-methyl-2-oxo-1-[[4-(1,2,3-thiadiazol-4-yl)phenyl]methyl]ethyl]carbamate

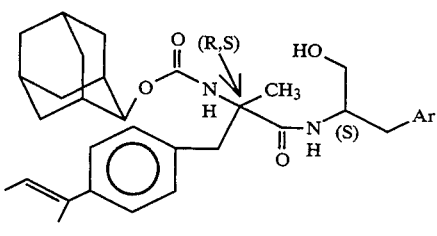

Starting from

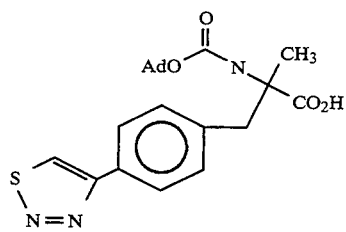

and (S)-(−)-2-amino-3-phenyl-1-propanol, the product was isolated by Workup A. Recrystallization from EtOAc-hexane gave 24% overall yield. Mixture of diastereomers. White solid, m.p. 97°–117° C.
Calcd: C, 66.87; H, 6.66; N, 9.75. Found: C, 66.83; H, 6.90; N, 9.34.

EXAMPLE 55

Tricyclo[3.3.1.1$^{3,7}$]dec-2-yl (S or R, S)-[2-[[2-hydroxy-1-(hydroxymethyl)-2-phenylethyl]amino]-1-methyl-2-oxo-1-[[4-(1,2,3-thiadiazol-4-yl)phenyl]methyl]ethyl]carbamate

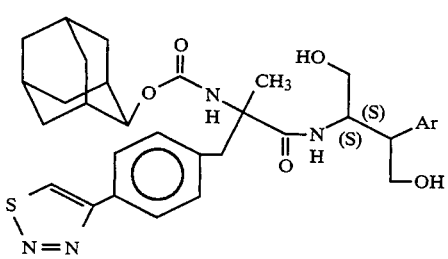

Using

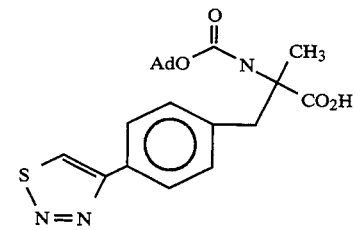

and (1S,2S)-(+)-2-amino-1-phenyl-1,3-propanediol the product was isolated by Workup A. The diastereomers were separated. Higher RF isomers. White solid. NMR (CDCl₃) δ 1.35 (3H, s), 1.5–2.15 (14H, m), 3.11–3.3 (2H, dd), 3.92–4.02 (4H, m), 4.84–5.16 (4H, m), 6.81 (1H, d), 7.12–7.41 (7H, m), 7.90 (2H, d), 8.63 (1H, s), 80% pure by HPLC, m.p. 120°–129° C. Lower RF isomer. White solid, m.p. 118°–124° C.

Calcd: C, 65.06; H, 6.48; N, 9.48. Found: C, 64.68; H, 6.57; N, 9.38.

EXAMPLE 56

Methyl 5-[(2-butyl-4-methyl-1H-benzimidazol-1-yl)methyl]-3-isoxazolecarboxylate

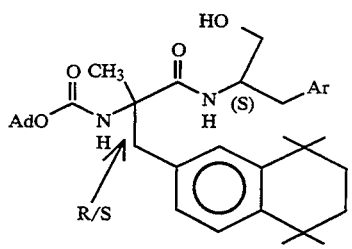

Using

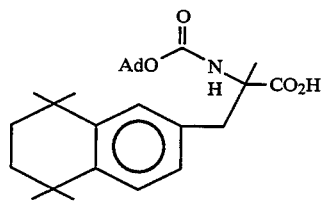

and (S)-(−)-2-amino-3-phenyl-1-propanol the product was isolated by Workup A. Recrystallization from t-butylmethyl ether-hexane gave 27% overall yield. Mixture of diastereomers. White solid. Isolated as 0.28 hydrate, m.p. 96°–101° C.

Calcd: C, 75.33; H, 8.74; N, 4.62. Found: C, 75.33; H, 8.55; N, 4.95.

EXAMPLE 57

Tricyclo[3.3.1.1³,⁷]dec-2-yl (±)-[1-methyl-2-oxo-2-[(2-phenylethyl)amino]-1-[5,6,7,8-tetrahydro-5,5,8,8-tetramethyl-2-naphthalenyl)-methyl]ethyl]carbamate

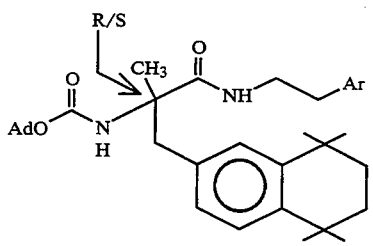

Using

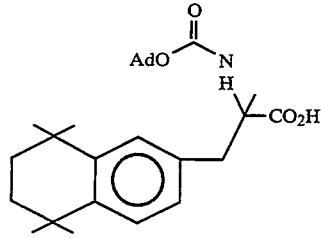

and phenethyl amine the product was isolated by Workup A. Crystallization from t-butylmethyl ether-hexane gave 62% overall yield. White solid. Isolated as 0.18 hydrate, m.p. 156°–159° C.

Calcd: C, 77.42; H, 8.84; N, 4.88. Found: C, 77.44; H, 8.85; N, 4.78.

INTERMEDIATES FOR EXAMPLES 58 AND 59

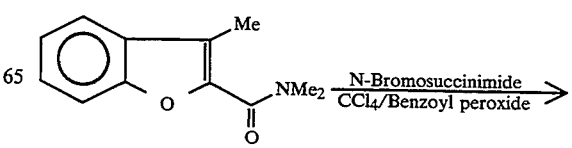

To a 100 mL reaction flask oven-dried under N₂ was added 3-methylbenzofuran-2-carboxylic acid (10 mmol), dimethyl amine hydrochloride (10.5 mmol), CH₂Cl₂ (50 mL), 1-hydroxybenzotriazole (10.5 mmol), 1-(3-dimethylaminopropyl)-3-ethylcarbodiimide hydrochloride (10.5 mmol), and triethylamine (21 mmol). The reaction was stirred at room temperature for 3 days and poured into CH₂Cl₂/.1N HCl (200 mL/200 mL). The aqueous layer was extracted with 3×200 mL of CH₂Cl₂, dried over MgSO₄, and then concentrated via roto evaporation. The crude reaction mixture was flash chromatographed on silica gel using 98/2 CH₂Cl₂/MeOH as eluant. Yielded 89% of NMR δ (CDCl₃) 2.46 (s, 3H), 3.13 (bs, 3H), 3.20 (bs, 3H), 7.25–7.60 (m, 4H). Mass Spec. (EI) parent ion at 203. IR (CHCl₃) cm⁻¹ 3009, 1628.

-continued

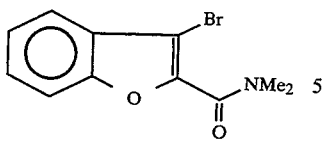

To a 50 mL reaction flask oven-dried under N₂ was added N,N,-3-trimethyl-2-benzofuran carboxamide (0.98 mmol), CCl₄ (10 mL), and N-bromosuccinimide (1.03 mmol), and finally benzoyl peroxide (0.049 mmol). The reaction was heated to reflux and refluxed for 30 minutes, cooled to room temperature, and filtered off solid. The mother liquors were concentrated and flash chromatographed on silica gel using hexane/ethyl acetate 75/25 as eluant. The product was isolated in 43% yield.

CHN: Calc: C, 51.09; H, 4.29; N, 4.96. Found: C, 51.19; H, 4.32; N, 5.04.

NMR (CDCl₃) δ 3.28 (bs, 3H), 3.39 (bs, 3H), 5.06 (s, 2H), 7.46–7.93 (m, 4H).

Using as the alkylating agent the product was isolated in 33% yield.

NMR (DMSO) δ 1.20–2.05 (m, 14H), 2.50 (s, 3H), 3.02 (s, 3H), 3.11 (s, 3H), 3.20–3.65 (m, 2H), 3.53 (s, 3H), 4.67 (s, 1H), 7.20–7.78 (m, 4H).

EXAMPLE 58

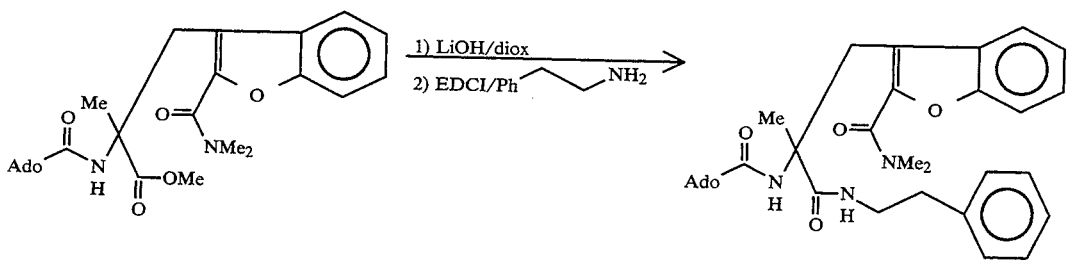

Utilizing workup B and phenethylamine the product was isolated as a white solid, m.p. 72°–83° C. in 34% yield after flash chromatography on silica gel using CH₂Cl₂/MeOH 97.5/2.5 as eluant. Mass Spec. FAB (thioglycerol) parent ion 572.

EXAMPLE 59

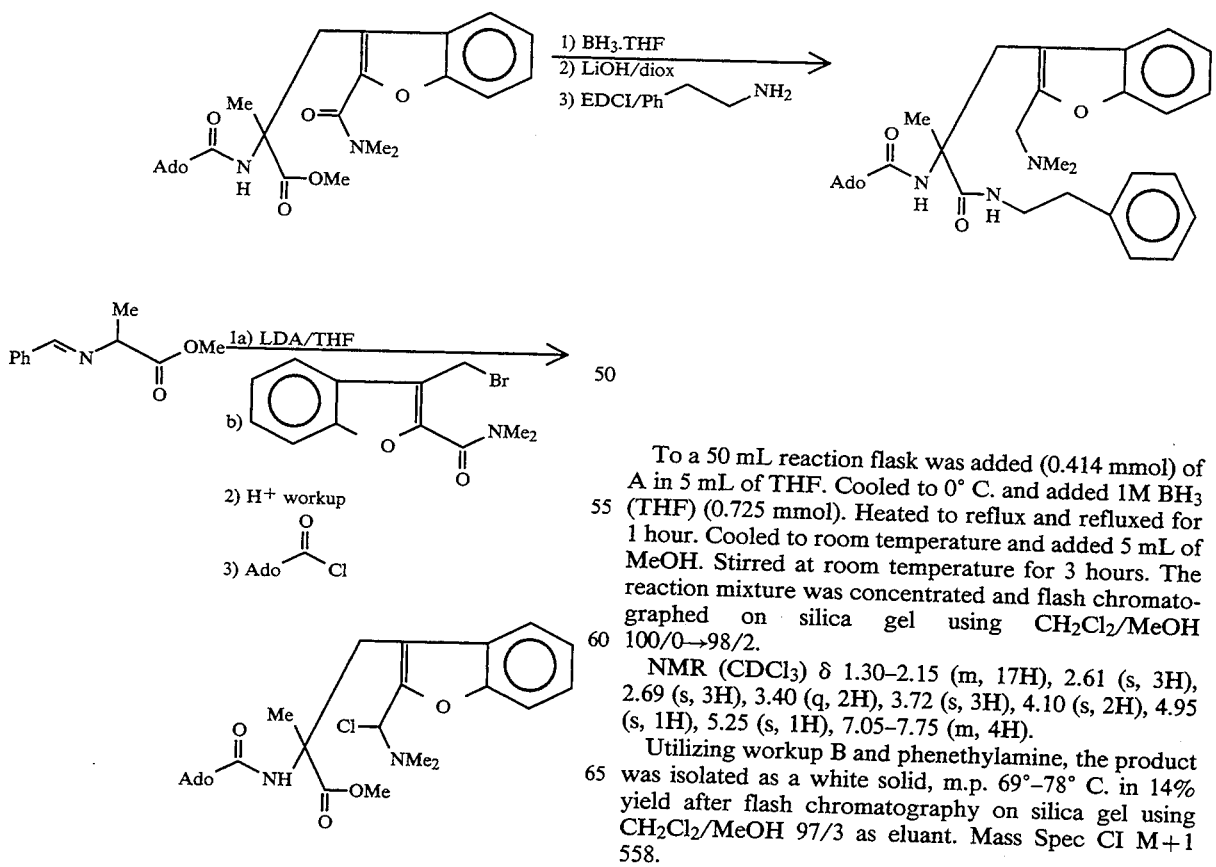

To a 50 mL reaction flask was added (0.414 mmol) of A in 5 mL of THF. Cooled to 0° C. and added 1M BH₃ (THF) (0.725 mmol). Heated to reflux and refluxed for 1 hour. Cooled to room temperature and added 5 mL of MeOH. Stirred at room temperature for 3 hours. The reaction mixture was concentrated and flash chromatographed on silica gel using CH₂Cl₂/MeOH 100/0→98/2.

NMR (CDCl₃) δ 1.30–2.15 (m, 17H), 2.61 (s, 3H), 2.69 (s, 3H), 3.40 (q, 2H), 3.72 (s, 3H), 4.10 (s, 2H), 4.95 (s, 1H), 5.25 (s, 1H), 7.05–7.75 (m, 4H).

Utilizing workup B and phenethylamine, the product was isolated as a white solid, m.p. 69°–78° C. in 14% yield after flash chromatography on silica gel using CH₂Cl₂/MeOH 97/3 as eluant. Mass Spec CI M+1 558.

EXAMPLE 60

Tricyclo[3.3.1.1³,⁷]dec-2-yl [S-[R*(R or S),R*]]-2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate

Step 1

α-Methyl-β-(3-1H-pyrrolo[2,3-b]pyridinyl-D,L-alanine methyl ester dihydrochloride To a suspension of potassium butoxide (560 mg, mmol) in 50 mL dry tetrahydrofuran at −30° C. was added a solution of methyl N-benzalalanate (J. W. Tilley, P. Levitan, R. W. Kirstead, *J. Heterocyclic Chem.* 16, 333 (1979)) (960 mg, 5 mmol) in 10 mL dry tetrahydrofuran. The mixture was stirred for 30 minutes at this temperature followed by addition of a solution of 3-dimethylaminomethyl-1H-pyrrolo[2,3-b]pyridine methiodide (1.58 g, 5 mmol), prepared in two steps by Mannich reaction of 1H-pyrrolo[2,3-b]pyridine with dimethylamine hydrochloride and paraformaldehyde in n-butanol (W. R. N. Williamson (*J. Chem. Soc.* (C) 2833 (1962)) and quaternization with methyl iodide (E. Benghiat, P. A. Crooks, *J. Heterocyclic Chem.* 20, 677 (1983)), in the minimum amount of DMSO. This mixture was stirred for 3 hours at −25° C. and then warmed to room temperature. Tetrahydrofuran was removed in vacuo, the residue was diluted with 500 mL water, followed by extraction with ethyl ether. The organic phase was dried over magnesium sulfate. The solvent was removed in vacuo to yield the Schiff base (1.2 g).

To the stirred solution of the crude Schiff base (1.2 g) in 100 mL methanol at 0° C. was added gaseous HCl. After 1 hour methanol was removed in vacuo to give the dihydrochloride of α-methyl-β-(3-1H-pyrrole[2,3-b]pyridinyl]-D,L-alanine methyl ester (1.14 g, 74.5% yield) as a colorless foam.

Steps 2 and 3

N-[(2-Adamantyloxy)carbonyl]-α-methyl-β-(3-1H-pyrrolo[2,3-b]pyridinyl)-D,L-alanine To a stirred suspension of crude α-methyl-β-(3-1H-pyrrolo[2,3-b]pyridinyl]-D,L-alanine methyl ester dihydrochloride (18.4 g, 60 mmol) in 400 mL dry tetrahydrofuran at room temperature was added diisopropylethylamine (19.4 g=26.1 mL, 150 mmol). The mixture was stirred for 30 minutes followed by addition of a solution of 2-adamantyl chloroformate (12.88 g, 60 mmol) in (12.88 g, 60 mmol) in 50 mL dry tetrahydrofuran and a solution of diisopropylethylamine (9.7 g=13.1 mL, 75 mmol) in 20 mL tetrahydrofuran.

After 24 hours, the solvent was removed in vacuo, the residue dissolved in 50 mL water and extracted with ethyl acetate. The ethyl acetate solution was washed twice with 5% citric acid and once with saturated brine. The organic phase was dried over magnesium sulfate and the solvent was removed in vacuo to yield a mixture of mono- and bis-[(2-adamantyloxy)carbonyl]adduct (26.19 g crude product).

To a stirred solution of the above crude product (19.41 g) in a mixture of 400 mL water and 200 mL dioxane was added under nitrogen lithium hydroxide (4.8 g, 200 mmol). After stirring overnight, dioxane was removed in vacuo. The aqueous phase was extracted with ethyl acetate to remove unreacted ester. The basic phase was acidified with 5% citric acid to pH 3 and extracted with ethyl acetate. The organic layer was dried over magnesium sulfate and concentrated in vacuo to yield the title compound as a colorless foam. The foam was dissolved in methanol and the acid precipitated by addition of water to yield a white powder (6.48 g, 36% overall yield), m.p. 145°–148° C.

Step 4

N-[(2-Adamantyloxy)carbonyl]-α-methyl-β-(3-1H-pyrrolo[2,3-b]pyridinyl)-D,L-alanine-(2S-hydroxy-1S-hydroxymethyl)-2-phenylethylamide To a stirred suspension of N-[(2-adamantyloxy)carbonyl]-α-methyl-β-(3-1H-pyrrolo[2,3-b]pyridinyl)-D,L-alanine (2.79 g, 7 mmol) and pentafluorophenol (1.37 g, 7.4 mmol) in 50 mL dry ethyl acetate at 0° C. was added N,N'-dicyclohexylcarbodiimide (1.53 g, 7.4 mmol). The reaction mixture was stirred 24 hours at this temperature. The precipitate was filtered and (1S,2S)-(+)-2-amino-1-phenyl-1,3-propandiol (1.24 g, 7.4 mmol) was added. This mixture was stirred 24 hours at room temperature, the solvent was removed in vacuo, and the resulting oily residue was separated by flash chromatography using ethyl acetate as solvent.

Diastereomer 1

Diastereomer 1 was obtained as a foam (0.96 g, 25% yield), softening at 85° C. RF=0.27 (ethyl acetate).

Diastereomer 2

Diastereomer 2 was obtained as a foam (0.85 g, 22% yield), softening at 80° C. Rf=0.16 (ethyl acetate).

EXAMPLE 61

Tricyclo[3.3.1.1³,⁷]dec-2-yl [1S-[1R*(R or S),2R*]]-2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate

Step 1

α-Methyl-β-(3-1H-pyrrolo[3,1-c]pyridinyl)-D,L-alanine methyl ester dihydrochloride To a suspension of potassium butoxide (2.8 g, 25 mmol) in 150 mL dry tetrahydrofuran at −30° C. was added a solution of methyl N-benzalalanate (J. W. Tilley, P. Levitan, R. W. Kirstead, *J. Heterocyclic Chem.,* 16, 333 (1979)) (4.76 g, 25 mmol) in 50 mL dry tetrahydrofuran. The mixture was stirred for 30 minutes at this temperature followed by addition of a solution of 3-dimethylaminomethyl-1H-pyrrolo[3,2-c]pyridine methiodide (7.95 g, 25 mmol), prepared in two steps by Mannich reaction of 1H-pyrrolo[3,2-c]pyridine with dimethylamine hydrochloride and paraformaldehyde in n-butanol (W. R. N. Williamson, *J. Chem. Soc.* (C) 2833 (1962)) and quaternization with methyl iodide (E. Benghiat, P. A. Crooks, *J. Heterocyclic Chem.,* 20, 677 (1983)), in the minimum amount of DMSO. This mixture was stirred for 3 hours at −25° C. and then warmed to room temperature. Tetrahydrofuran was removed in vacuo, the residue was diluted with 500 mL water, followed by extraction with ethyl ether. The organic phase was dried over magnesium sulfate. The solvent was removed in vacuo to yield the Schiff base (4.43 g).

To the stirred solution of the crude Schiff base (4.43 g) in 100 mL methanol at 0° C. was added gaseous HCl. After 18 hours methanol was removed in vacuo to give the dihydrochloride of α-methyl-B-(3-1H-pyrrolo-[3,2- c]pyridinyl)-D,L-alanine methyl ester (2.1 g, 50% yield) as a colorless powder.

Steps 2 and 3

N-[(2-Adamantyloxy)carbonyl]-α-methyl-β-(3-1H-pyrrolo[3,2-c]pyridinyl-D,L-alanine To a stirred suspension of crude α-methyl-β-(3-1H-pyrrolo[3,2-c]pyridinyl)-D,L-alanine methyl ester dihydrochloride (2.58 g, 7.5 mmol) in 60 mL dry tetrahydrofuran at room temperature was added diisopropylethylamine (3.88 g=5.23 mL, 30 mmol). The mixture was stirred for 60 minutes followed by addition of a solution of 2-adamantyl chloroformate (3.21 g, 15 mmol) in 20 mL dry tetrahydrofuran.

After 24 hours, the solvent was removed in vacuo, the residue dissolved in 500 mL water, and extracted with ethyl acetate. The ethyl acetate solution was washed twice with 5% citric acid and once with saturated brine. The organic phase was dried over magnesium sulfate and the solvent was removed in vacuo to yield a mixture of mono- and bis-[(2-adamantyloxy)carbonyl]adduct (4.03 g crude product).

To a stirred solution of the above crude product (4.03 g) in a mixture of 75 mL water and 150 mL dioxane was added under nitrogen lithium hydroxide (0.36 g, 15 mmol). After stirring overnight, dioxane was removed in vacuo. The aqueous phase was extracted with ethyl acetate to remove unreacted ester. The basic phase was acidified with 15 mL 1N HCl to pH 5 to yield the acid as a white precipitate (0.48 g, 16% overall yield), m.p. 245° C.

Step 4

N-[(2-Adamantyloxy)carbonyl]-α-methyl-β-(3-1H-pyrrolo[3,2-c]pyridinyl]-D,L-alanine-(2S-hydroxy-1S-hydroxymethyl)-2-phenylethyamide To a stirred suspension of N-[(2-adamantyloxy)carbonyl]-α-methyl-β-(3-1H-pyrrolo[2,3-b]pyridinyl)-D,L-alanine (397 mg, 1 mmol) and pentafluorophenol (190 mg, 1.03 mmol) in 40 mL dry ethyl acetate at was added N,N[-dicyclohexylcarbodiimide (230 mg, 1.12 mmol). The reaction mixture was stirred 24 hours at this temperature, followed by addition of N,N'-dicyclohexylcarbodiimide (230 mg, 1.12 mmol) and stirring this mixture at 60° C. for 3 hours. The precipitate was filtered and (1S,2S)-(+)-2-amino-1-phenyl-1,3-propandiol (167 mg, 1 mmol) was added. This mixture was stirred 48 hours at room temperature, the solvent was removed in vacuo, and the resulting foam was separated by column chromatography using methylene chloride/methanol 98/2 as solvent.

Diastereomer 1

Diastereomer 1 was obtained as a white powder (0.12 g, 22% yield), m.p. 150°–175° C. RF=0.5 (methylene chloride:methanol 4:1).

Diastereomer 2

Diastereomer 2 was obtained as a white powder (0.13 g, 22% yield), m.p. 155°–175° C.Rf=0.4 (methylene chloride: methanol 4:1).

EXAMPLE 62

Carbamic acid,
[1-[(2,3-dimethyl)-1H-pyrrol-4-ylmethyl]-1-methyl-2-oxo-2-[(2-phenylethyl)amino]ethyl-,
tricyclo[3.3.1.1$^{3,7}$]dec-2-yl ester Intermediate II
(compound 10, Scheme XIV)

Racemic
N-[(2-Adamantyloxy)carbonyl]-3-[(2,3-dimethyl)-1H-pyrrol-4-yl)]-2-methyl-alanine Step 1

2,3-Dimethyl-1-(4-methylphenyl)sulfonyl-1H-pyrrole-4-carboxylic acid methyl ester To a stirred solution of 2,3-dimethyl-1H-pyrrole-4-carboxylic acid methyl ester (*Heterocycles* 1977, 7, 77) (7.95 g, 51.9 mmol) in THF (160 mL) was added dropwise 50% NaOH (80 mL). The reaction mixture was stirred for 5 minutes and then a solution of p-toluenesulfonyl chloride (11.87 g, 62.3 mmol) in THF (160 mL) was added dropwise to the stirred mixture at room temperature. The mixture was stirred at room temperature for 30 minutes then cooled to 5 to 10° C. and treated dropwise with water (200 mL). The THF was evaporated in vacuo and the aqueous residue was thoroughly extracted with $CH_2Cl_2$. The organic extract was washed, dried ($Na_2SO_4$), and concentrated in vacuo. The residue was chromatographed over silica gel using toluene as eluant to give the required compound (13.6 g, 85%) as a pale yellow solid, m.p. 108°–114° C.

Step 2

2,3-Dimethyl-4-hydroxymethyl-1-(4-methylphenyl)-sulfonyl-1H-pyrrole

To a stirred solution of the ester of Step 1 (11.1 g, 36 mmol) in dry THF (60 mL), cooled to 10 to 15° C. and under nitrogen, was added dropwise a solution of Red-Al (18 mL) in dry THF (60 mL). After stirring for 3 hours at room temperature the mixture was cooled to 5° to 10° C. and hydrolyzed dropwise with 2N NaOH (40 mL). The organic phase was separated, dried ($Na_2SO_4$), and concentrated in vacuo. The residue was chromatographed over silica gel using toluene/ethyl acetate 95–90/5–10 (v/v) as eluant to give the desired alcohol (8.0 g, 80%) as a brownish solid, m.p. 83°–86° C.

Step 3

4-Chloromethyl-2,3-dimethyl-1-(4-methylphenyl)-sulfonyl-1H-pyrrole

To a stirred solution of the alcohol from Step 2 (6.8 g, 24.3 mmo 1 ) in dry toluene (70 mL) was added dropwise $SOCl_2$ (9.5 mL) and the mixture was stirred for 3 hours at room temperature. The excess of $SOCl_2$ and the solvent were removed in vacuo and the residue partitioned between water (10 mL) and diethyl ether (100 mL). The organic phase was separated, dried ($NaSO_4$), and concentrated in vacuo to give the required compound as a brown solid, m.p. 105°–109° C., which was used without further purification.

Step 4

Racemic
3-[[2,3-Dimethyl-1-(4-methylphenyl)sulfonyl]-1H-pyrrol-4-yl]-2-methyl-alanine methyl ester To a stirred suspension of sodium hydride (0.66 g, 80 Wt % in paraffin oil, 22 mmol) in dry DMSO (20 mL)

at room temperature under a nitrogen atmosphere was added dropwise a solution of N-(phenylmethylene)-DL-alanine methyl ester (4.2 g, 22 mmol) in dry DMSO (20 mL). After 1 hour stirring the reaction mixture was cooled to 10° to 15° C. and a solution of the compound from Step 3 (5.95 g, 20 mmol) in dry DMSO (30 mL) was added in one portion and the resultant mixture left stirring for 24 hours at room temperature. After removing the solvent in vacuo, the residue was partitioned between water (200 mL) and $CH_2Cl_2$ (400 mL). The organic extract was dried ($Na_2SO_4$) and evaporated. The resulting oil was stirred for 3 hours with 1N hydrochloric acid (80 mL) and diethyl ether (100 mL), the aqueous phase was separated, made basic with potassium carbonate, extracted with $CH_2Cl_2$, and dried ($Na_2SO_4$). After removing the solvent in vacuo, the residue was purified by chromatography over silica using $MeOH/CH_2Cl_2$ 1:99 (v/v) as eluant to give the desired compound (4.5 g, 62%) as a yellow oil, which solidified upon standing; IR (KBr) 1730 $cm^{-1}$.

Step 5

Racemic N-[(2-Adamantyloxy)carbonyl]3-[[2,3-dimethyl-1-(4-methylphenyl)sulfonyl]-1H-pyrrol-4-yl]-2-methylalanine methyl ester To a stirred solution of the compound of Step 4 (4.3 g, 11.8 mmol) in dry THF (60 mL) was added a solution of 2-adamantyl chloroformate (2.8 g, 13 mmol) in dry THF (10 mL) followed by a solution of triethylamine (1.3 g, 13 mmol) in dry THF (10 mL) dropwise. After 2 hours stirring, the reaction mixture was filtered, the solvent removed in vacuo, and the residue chromatographed over silica gel using ethanol/toluene 1:20 (v/v) as eluant to provide 6.1 g (95%) of product as a non-crystalline solid; IR (KBr) 1745 and 1720 $cm^{-1}$.

Step 6

A mixture of the ester of Step 5 (2.9 g, 5.3 mmol) and KOH (2.0 g, 35.6 mmol) in ethanol (40 mL) was refluxed for 26 hours. After removing the solvent in vacuo the residue was partitioned between water 9150 μL) and $CH_2Cl_2$ (50 mL). The water phase was separated, acidified with 1M citric acid solution to pH 4.5, and extracted with diethyl ether. The organic extract was dried ($Na_2SO_4$), treated with activated charcoal, and evaporated in vacuo to give the title compound (1.6 g, 80%) as a brownish amorphous solid, sintering at 120° C., used without further purification; IR (KBr) 1711 $cm^{-1}$; MS (70 e/v): m/z ($DCI+NH_3$) 375 $(M+H)^+$.

Carbamic acid, [1-[(2,3-dimethyl)-1H-pyrrol-4-ylmethyl]-1-methyl-2-oxo-2-[(2-phenylethyl)amino]ethyl]-, tricyclo[3.3.1.1$^{3,7}$]dec-2-yl ester To a solution of racemic N-[(2-adamantyloxy)carbonyl]-3-[[2,3-dimethyl)-1H-pyrrol-4-yl)]-2-methylalanine (0.375 g, 1 mmol) in dry THF (8 mL) was added 1,1'-carbonyldiimidazole (0.172 g, 1.1 mmol) and stirred for 1 hour. To this mixture was added dropwise a solution of phenylethylamine (0.121 g, 1 mmol) in dry THF (4 mL). After stirring for 20 hours the solvent was renored in vacuo and the residue was partitioned between water (50 mL) and diethyl ether (75 mL). The organic phase was separated, washed, dried ($Na_2SO_4$), and the solvent evaporated. The residue was chromatographed over silica gel using $MeOH/CH_2Cl_2$ 1:99 (v/v) as eluant to give the title compound (0.10 g, 22%) as a light brown amorphous solid, m.p. 81°–88° C.

EXAMPLE 63

Carbamic acid, [1-[(2,3-dimethyl)-1H-pyrrol-4-ylmethyl]-2-[[1-(hydroxymethyl)-2-hydroxy-2-phenylethyl]amino]-1-methylethyl]-, tricyclo[3.3.1.1$^{3,7}$]dec-2-yl ester (mixture of isomers)

Method was as described for Example 60 above, except the amine used was (1S,2S)-(−)-2-amino-1-phenyl-1,3-propanediol. Yield 0.090 g (13%) as a light brown amorphous solid, m.p. 113°–121° C.

EXAMPLE 64

Carbamic acid [1-(imidazo[1,5-a]pyridin-3-ylmethyl)-2-oxo-2-[(2-phenylethyl)amino]ethyl]-, tricyclo[3.3.1.1$^{3,7}$]dec-2-yl ester Intermediate II (see Compound 8, Scheme XVI)

Racemic N-[(2-Adamantyloxy)carbonyl]-3-(imidazo]1,5-a]pyridin-3-yl)-2-methyl-alanine Step 1

3-Dimethylaminomethyl-imidazo[1,5-a]pyridine

A mixture of 40% aqueous dimethylamine (10.2 g), formalin (7.4 g), and glacial acetic acid, cooled to 0° to 5° C., was given to imidazo[1,5-a]pyridine [*J. Chem. Soc.*, 1955, 2834](10.0 g, 84 mmol). The resulting dark mixture was left stirring for 48 hours at room temperature, then was made basic with 2N NaOH and extracted with $CH_2Cl_2$. The combined extracts (2×100 mL) were dried ($Na_2SO_4$) and evaporated. The residue was purified by chromatography over silica gel using $MeOH/CH_2Cl_2$ 2:98 as eluant to give the title compound (3.0 g, 20%) as an oil; MS (70 eV): m/z 175 ($M^+$).

Step 2

3-Dimethylaminomethyl-imidazo[1,5-a]pyridine methiodide

The compound of Step 1 (3.5 g, 20 mmol) was dissolved in a mixture of absolute ethanol (35 mL) and absolute tetrahydrofuran (28 mL) containing glacial acetic acid (0.18 mL). Methyl iodide (1.17 mL, 18.7 mmol) was added to the solution which was stirred at room temperature for 15 minutes and then kept at 4° C. for 3 hours. The resultant precipitate was filtered off and washed with diethyl ether to give the required compound (5.0 g, 80%) as an almost colorless solid, m.p. 251°–252° C.

Step 3

Racemic 3-(Imidazo[1,5-a]pyridin-3-yl)-2-methyl-alanine methyl ester

A solution of N-(phenylmethylene)-DL-alanine methyl ester (2.86 g, 15 mmol) in dry THF (20 mL) was added to a stirred solution of potassium t-butoxide (1.70 g, 15 mmol) in dry THF (90 mL) at −30° C. under a nitrogen atmosphere. The resulting bright red solution was stirred at −30° C. for 30 minutes and a solution of the methiodide of Step 2 (4.70 g, 14.8 mmol) in dry DMSO (20 mL) was added dropwise. The resulting mixture was stirred 2 hours at −20° to −30° C., then 48 hours at room temperature. After removing the solvent in vacuo, the residue was partitioned between water (100 mL) and $CH_2Cl_2$ (200 mL). The organic extract was dried ($Na_2SO_4$) and evaporated. The resulting oil was stirred for 3 hours with 1N hydrochloric acid (10 mL) and diethyl ether (10 mL), the aqueous phase was separated, made basic with potassium carbonate, extracted with $CH_2Cl_2$m dried ($Na_2SO_4$), and the solvent removed in vacuo to give the product (0.83 g, 24 %) as a syrup, which was used without further purification; IR (film) 1734 cm$^{-1}$.

Step 4

Racemic N-[(2-Adamantyloxy)carbonyl]-3-(imidazo[1,5-a]pyridin-3-yl)-2-methyl-alanine methyl ester To a stirred solution of the crude compound of Step 3 (0.83 g, 3.56 mmol) in dry THF (10 mL) was added a solution of 2-adamantyl chloroformate (0.80 g, 3.7 mmol) in dry THF (3 mL) followed by a solution of triethylamine (0.38 g, 3.8 mmol) in dry THF (5 mL) dropwise. After 2 hours stirring, the reaction mixture was filtered, and the solvent removed in vacuo to give the product (1.2 g, 82%) as a colorless amorphous solid, which was used without further purification; IR (KBr) 1737 and 1699 cm$^{-1}$.

Step 5

To a solution of the crude ester of Step 4 in a mixture of 1,4-dioxane (40 mL) and water (15 mL) was added LiOH (0.30 g, 12 mmol) and the mixture stirred for 4 hours. After removing the solvent in vacuo, the residue was partitioned between water (80 mL) and diethyl ether (30 mL). The water phase was separated, acidified with 1M citric acid solution to pH 4.5, and extracted with ethyl acetate. The organic extract was dried ($Na_2SO_4$) and evaporated in vacuo to give the title compound (0.80 g, 70%) as a pale yellow amorphous solid, which was used without further purification; IR (KBr) 1704 cm$^{-1}$.

Carbamic acid, [1-(imidazo[1,5a]pyridin-3-ylmethyl)-2-oxo-2-[(2-phenylethyl)amino]ethyl]-, tricyclo-[3.3.1.1$^{3,7}$]dec-2-yl ester To a solution of racemic N-[(2-adamantyloxy)carbonyl]-3-(imidazo[1,5-a]pyridin-3-yl)-2-methylalanine (0.30 g, 0.75 mmol) in dry THF (20 mL) was added 1,1'-carbonyldiimidazole (0.13 g, 0.80 mmol) and stirred for 1 hour. To this mixture was added dropwise a solution of phenylethylamine (90 mg, 0.75 mmol) in dry THF (3 mL). After stirring for 3 hours the solvent was removed in vacuo and the 30 residue was partitioned between water (50 mL) and $CH_2Cl_2$ (100 mL). The organic phase was separated, washed, dried ($Na_2SO_4$), and the solvent evaporated. The residue was chromatographed over silica gel using MeOH/$CH_2Cl_2$ 2:98 (v/v) as eluant to give the title compound which was triturated with dry diethyl ether to obtain a colorless solid, which was removed by filtration (60 mg, 22%), m.p. 171°-172° C.

EXAMPLE 65

Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1$^{3,7}$]dec-2-yl ester (mixture of isomers)

Method was as described for Example 64 above, except the amine used was (1S,2S)-(−)-2-amino-1-phenyl-1,3-propanediol. Yield 0.14 g (20%) as a colorless amorphous solid, sintering at 101° C.

The following compounds were made in an analogous manner:

4-[[2-[[2-Methyl-1-oxo-3-(4-pyridinyl)-2-[[(tricyclo[3.3.1.1$^{3,7}$]dec-2-yloxy)carbonyl]amino]propyl]amino]-1-phenylethyl]amino]-4-oxobutanoic acid, 4-[[2-[[3-(2,3-dihydro-1-methyl-5-phenyl-1H-benzodiazepin-2-yl)-2-methyl-1-oxo-2-[[(tricyclo-[3.3.1.1$^{3,7}$]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1$^{3,7}$]dec-2-yl [2-[[1-(hydroxymethyl)-2-phenylethyl]amino]-1-methyl-2-oxo-1-(2-pyridinylmethyl)ethyl]carbamate, N-oxide, Tricyclo[3.3.1.1$^{3,7}$]dec-2-yl [1-[(2,3-dihydro-1-methyl-5-phenyl-1H-1,4-benzodiazepin-2-yl) methyl]-1-methyl-2-[(2-phenylethyl)amino]-2-oxoethyl]carbamate, and Tricyclo[3.3.1.1$^{3,7}$]dec-2-yl [2-[[1-hydroxymethyl)-2-phenylethyl]amino]-1-methyl-2-oxo-1-(4-pyridinylmethyl)ethyl]carbamate.

We claim:

1. A compound of formula

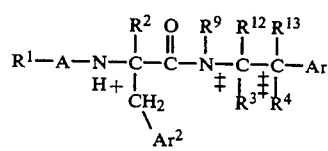

or a pharmaceutically acceptable salt thereof wherein:

$R^1$ is a cycloalkyl or polycycloalkyl hydocarbon of from three to twelve carbon atoms with from zero to four substituents each independently selected from the group consisting of alkyl, halogen, CN, OR*, SR*, $CO_2R$*, $CF_3$, $NR^5R^6$, and —($CH_2$)$_n$OR$^5$ wherein R* is hydrogen or alkyl, $R^5$ and $R^6$ are each independently hydrogen or alkyl and n is an integer from zero to six with the proviso that n is an integer from one to six where $R^1$ is —($CH_2$)$_n$OR$^5$;

A is —($CH_2$)$_n$CO—, —$SO_2$—, —S(═O)—, —NH-CO—,

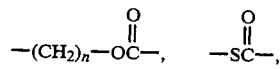

—O—($CH_2$)CO—,       —O—($CH_2$)$_2$CO—,
—O—($CH_2$)$_3$CO—,       —O—($CH_2$)$_4$CO—,
—O—($CH_2$)$_5$CO—,   —O—($CH_2$)$_6$CO—, or
—HC═CHCO— wherein n is an integer from zero to six;

$R^2$ is alkyl, —($CH_2$)$_n$—CH═$CH_2$, —($CH_2$)$_n$C≡CH, —($CH_2$)$_n$Ar, —($CH_2$)$_n$OR*, —($CH_2$)$_n$OAr, —($CH_2$)$_n$CO$_2$R*, or —($CH_2$)$_n$NR$^5$R$^6$ wherein n, R*, R⁵, and R⁶ are as defined above and Ar is as defined below;

R³ and R⁴ are each independently selected from hydrogen, R² and —(CH₂)$_{n'}$-β-D wherein:

n' is an integer of from zero to three;
β is a bond,
—OCO(CH₂)$_n$—,
—O(CH₂)$_n$—,
—NHCO—,
—NHCOCH₂—,
—NHCO(CH₂)₃—,
—NHCO(CH₂)₄—,
—NHCO(CH₂)₅—,
—NHCO(CH₂)₆—,
—CONH—,
—CONHCH₂—,
—CONH(CH₂)₃—,
—CONH(CH₂)₄—,
—CONH(CH₂)₅—,
—CONH(CH₂)₆—,
—COO(CH₂)$_n$—,
—CO(CH₂)$_n$—,
—S—(CH₂)$_n$—,
—S(=O)—(CH₂)$_n$—,
—SO₂—(CH₂)$_n$—,
—NHSO₂—(CH₂)$_n$—,
—SO₂NH(CH₂)$_n$—,

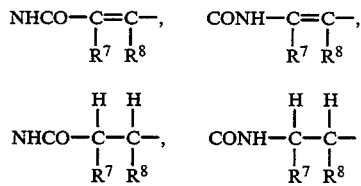

wherein R⁷ or R⁸ are independently selected from hydrogen and R² or together form a ring (CH₂)$_m$ wherein m is an integer of from 1 to 5 and n is as defined above;

D is
—COOR*,
—CH₂OR*,
—CHR²OR*,
—CH₂SR*,
—CHR²SR*,
—CONR⁵R⁶,
—CN,
—NR⁵R⁶,
—OH,
—H and the acid replacements

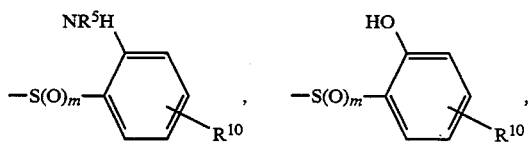

wherein R¹⁰ is OH, NH₂, CH₃ or Cl, wherein m is an integer of from 0 to 2, wherein R*, R², R⁵, and R⁶ are as defined above;

R⁹ is hydrogen or alkyl, —(CH₂)$_n$CO₂R*, —(CH₂)$_n$OAr', —(CH₂)$_n$NR⁵R⁶, wherein n, R*, R⁵, and R⁶ are as defined above or taken from R³ and Ar' is taken from Ar as defined below;

R¹² and R¹³ are each independently hydrogen;

Ar is an unsubstituted or substituted hydrocarbon ring system selected from a monocyclic 5- or 6-member ring or a bicyclic ring system wherein each ring is independently a 5- or 6-member ring and a tricyclic ring system wherein each ring is independently a 5- or 6-member ring wherein the substituent is independently selected from nitro, NR⁵R⁶, halogen, alkyl, hydroxy or alkoxy; and Ar² is selected from Ar as defined above or, naphthyl or the CH₂Ar² moiety of formula I is the sidechain of phenylalanine or tyrosine, the above alkyl or alkoxy groups have a straight or branched chain of from one to six carbon atoms.

2. A compound according to claim 1 wherein:
R¹ is a cycloalkyl or a polycycloalkyl of from six to ten carbon atoms with from zero to four substituents each independently selected from hydrogen, straight or branched alkyl of from one to six carbon atoms, CF₃, NR⁵R⁶, —(CH₂)$_n$CO₂R*, CN, F, Cl, Br, OR*, SR*, wherein R*, R⁵, and R⁶ are as defined in claim 1 and n is an integer of from 1 to 3;

A is —NHCO—, OC(=O)—, —SO₂—, —S(=O),

or —CH₂CO—;

R² is CH₃, —CH₂CO₂H or —CH₂C≡CH;
R³ is —(CH₂)$_{n'}$—β—D or H;
R⁴ is —(CH₂)$_{n'}$—β—D or H;
R⁹ is hydrogen or methyl;
R¹² is hydrogen;
R¹³ is hydrogen;

Ar is a hydrocarbon ring system selected from a monocyclic 5- or 6-member ring of a bicyclic ring system wherein each ring is independently a 5- or 6-member ring and a tricyclic ring system wherein each ring is independently a 5- or 6-member ring;

Ar² is selected from Ar or is naphthyl or the CH₂Ar² is the sidechain of phenylalanine.

3. A compound according to claim 1 wherein R¹ is an unsubstituted or substituted cycloalkyl or polycycloalkyl selected from

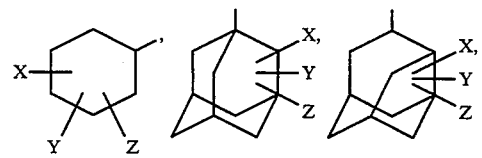

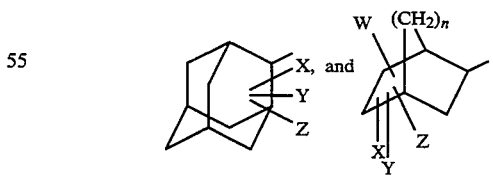

wherein
W, X, Y, and Z are each independently hydrogen, a straight or branched alkyl or from one to six carbon atoms, CF₃, NR⁵N⁶, —(CH₂)$_n$CO₂R*, CN, F, Cl, Br, OR*, SR*, wherein R*, R⁵, and R⁶ are as defined in claim 1 and n is an integer of from 1 to 3;

A is —NHCO—, OCO—, —SO₂—, —S(=O)— or —CH₂CO—;

123

$R^2$ is —$CH_3$, —$CH_2CO_2H$, or —$CH_2C{\equiv}CH$;
$R^3$ is H, $CH_2OH$, $CH_2OCOCH_2CH_2CO_2H$, $CH_2OCOCH{=}CHCO_2H$, $CH_2NHCOCH_2CH_2CO_2H$, $CH_2NHCOCH{=}CHCO_2H$, $CH_2SCH_2CO_2H$, —$CH_2SCH_2CH_2CO_2H$, or —$CH_2CO_2H$,
$R^4$ is H, —$NHCOCH_2CH_2CO_2H$ or $NHCOCH{=}CHCO_2H$,
$R^9$ is H or methyl,
$R^{12}$ is hydrogen,
$R^{13}$ is hydrogen,
Ar and $Ar^2$ are as defined in claim 1.

4. A compound according to claim 1 wherein
$R^1$ is 2-adamantyl, 1-(S)-2-endobornyl, or 2-methylcyclohexyl;
A is —OC(=O);
$R^2$ is $CH_3$;
$R^3$ is H, $CH_2OH$, $CH_2OCOCH_2CH_2CO_2H$, $CH_2OCOCH{=}CHCO_2H$, $CH_2NHCOCH_2CH_2CO_2H$, $CH_2NHCOCH{=}CHCO_2H$, $CH_2SCH_2CO_2H$, or $CH_2SCH_2CH_2CO_2H$,
$R^4$ is H, —$NHCOCH_2CH_2CO_2H$ ([D] configuration) or $NHCOCH{=}CHCO_2H$ ([D] configuration);
$R^9$ is hydrogen or methyl;
$R^{12}$ is hydrogen;
$R^{13}$ is hydrogen;
Ar is

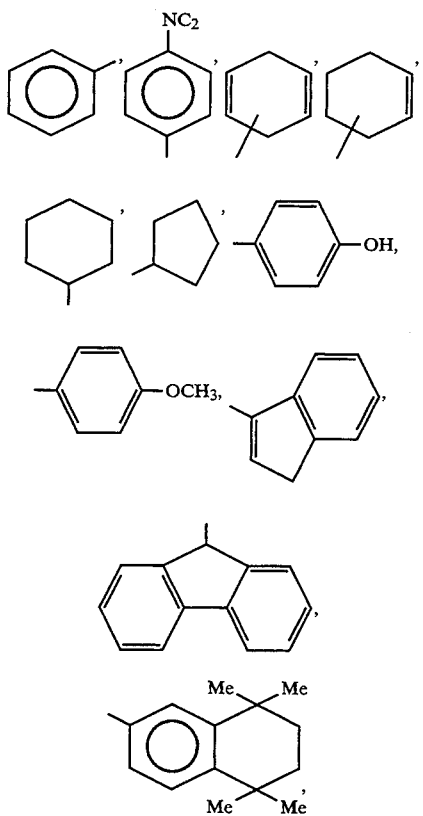

$Ar^2$ is as defined above for Ar, or the $CH_2Ar^2$ moiety of formula I is the sidechain of phenylalanine or tyrosine, or
$Ar^2$ is: naphthyl
each of the above moieties for Ar and $Ar^2$ being independently unsubstituted, mono- or polysubstituted wherein the substituent is independently selected from $NR^5R^6$, halogen, alkyl, or alkoxy.

5. A compound according to claim 1 wherein

124

$R_1$ is an unsubstituted or substituted cycloalkyl or polycycloalkyl

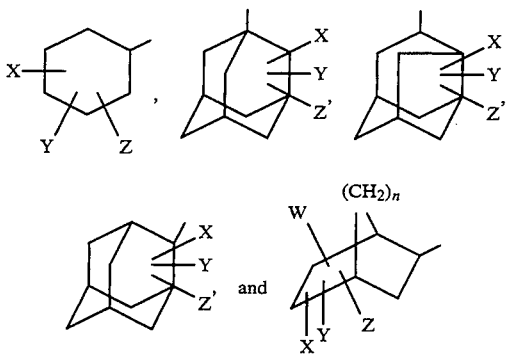

wherein W, X, Y, and Z are each independently hydrogen, a straight or branched alkyl of from one to six carbon atoms, $CF_3$, $NR^5N^6$, —$(CH_2)_nCO_2R^*$, CN, F, Cl, Br, $OR^*$, $SR^*$, wherein $R^*$, $R^5$, and $R^6$ are as defined in claim 1 and n is an integer of from 1 to 3;
A is OCO—;
$R_2$ is —$CH_3$, —$CH_2CO_2H$, or —$CH_2C{\equiv}CH$;
$R^3$ is H, $CH_2OH$, $CH_2OCOCH_2CH_2CO_2H$, $CH_2OCOCH{=}CHCO_2H$, $CH_2NHCOCH_2CH_2CO_2H$, $CH_2NHCOCH{=}CHCO_2H$, —$CH_2SCH_2CO_2H$, —$CH_2SCH_2CH_2CO_2H$, or —$CH_2CO_2H$,
$R^4$ is H, —$NHCOCH_2CH_2CO_2H$ or $NHCOCH{=}CHCO_2H$,
$R^9$ is H or methyl,
$R^{12}$ is hydrogen,
$R^{13}$ is hydrogen,
Ar is phenyl, or substituted phenyl, wherein the substituent is independently selected from $NR^5R^6$, halogen, alky, alkoxy or nitro; and
$Ar^2$ is 1-napthyl or 2-naphthyl.

6. A compound named
Tricyclo[3.3.1.1³,⁷]dec-2-yl[2-[[1-(hydroxymethyl)-2-phenylethyl]amino]-1-methyl-1-(1-naphthalenylmethyl)-2-oxoethyl]carbamate (naphthalenylmethyl center is RS, other center is S),
Tricyclo[3.3.1.1³,⁷]dec-2-yl[2-[[1-(hydroxymethyl)-2-phenylethyl]amino]-1-methyl-1-(2-naphthalenylmethyl)-2-oxoethyl]carbamate (naphthalene center is RS, hydroxymethyl center is S),
Tricyclo[3.3.1.1³,⁷]dec-2-yl(±)-[2-[[1-methyl-1-(1-naphthalenylmethyl)-2-oxo-2-[(2-phenylethyl)amino]ethyl]carbamate,
Tricyclo[3.3.1.1³,⁷]dec-2-yl(±)-[1-methyl-1-(1-naphthalenylmethyl)-2-oxo-2-[(2-phenylethyl)amino]ethyl]carbamate, and
Tricyclo[3.3.1.1³,⁷]dec-2-yl[2-[[1-(hydroxymethyl)-2-phenylethyl]amino]-1-methyl-1-(2-naphthalenylmethyl)-2-oxoethyl]carbamate (hydroxy center is S, other center is R or S) (Isomer I).

7. A compound according to claim 1 named
Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate.

8. A compound according to claim 1 named
Tricyclo[3.3.1.1³,⁷]dec-2-yl [2-[[2-hydroxy-1-(hydroxymethyl)-2-phenylethyl]amino]-1-[(4-hydroxyphenyl)methyl]-1-methyl-2-oxoethyl]-carbamate (Mixture of [1S-[1R*(R*),2R*]] and [1S-[1R*(S*),2R*]] isomers).

9. A compound according to claim 1 named Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]-carbamate (Mixture of [1S-[1R*(R*),2R*]] and [1S-[1R*(S*),2R*]] isomers).

10. A compound according to claim 1 named Tricyclo[3.3.1.1³,⁷]dec-2-yl[2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers).

11. A compound named Tricyclo[3.3.1.1³,⁷]dec-2-yl (±)-[1-methyl-2-oxo-2-[(2-phenylethyl)amino]-1-[(5,6,7,8-tetrahydro-5,5,8,8-tetramethyl-2-naphthalenyl)methyl]ethyl]carbamate.

12. A pharmaceutical composition comprising an antigastric acid secretion amount of a compound according to claim 1 and a pharmaceutically acceptable carrier.

13. A method of reducing gastric acid secretion in a mammal, comprising administering an effective gastric acid secretion reducing amount of a compound according to claim 1.

14. A pharmaceutical composition comprising an antigastrointestinal ulcer effective amount of a compound according to claim 1 and a pharmaceutically acceptable carrier.

15. A method for treating gastrointestinal ulcers in a mannal comprising administering an effective gastrointestinal ulcer treating amount of a compound according to claim 1.

16. A method of reducing gastric acid secretion in a mammal comprising administering an effective gastric acid secretion reducing amount of a compound named Tricyclo[3.3.1.1³,⁷]dec-2-yl[2-[[1-(hydroxymethyl)-2-phenylethyl]amino]-1-methyl-1-(1-naphthalenylmethyl)-2-oxoethyl]carbamate (naphthalenylmethyl center is RS, other center is S), Tricyclo[3.3.1.1³,⁷]dec-2-yl[2-[[1-(hydroxymethyl)-2-phenylethyl]amino]-1-methyl-1-(2-naphthalenylmethyl)-2-oxoethyl]carbamate (naphthalene center is RS, hydroxymethyl center is S), Tricyclo[3.3.1.1³,⁷]dec-2-yl(±)-[1-methyl-1-(1-naphthalenylmethyl)-2-oxo-2-[(2-phenylethyl)amino]ethyl]carbamate, Tricyclo[3.3.1.1³,⁷]dec-2-yl(±)-[1-methyl-1-(2-naphthalenylmethyl)-2-oxo-2-[(2-phenylethyl)]amino]ethyl]carbamate, and Tricyclo[3.3.1.1³,⁷]dec-2-yl[2-[[2-(hydroxymethyl)-2-phenylethyl]amino]-1-methyl-1-(2-naphthalenylmethyl)-2-oxoethyl]carbamate (hydroxy center is S, other center is R or S) (Isomer I).

17. A method of reducing gastric acid secretion in a mammal comprising administering an effective gastric acid secretion reducing amount of a compound named Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate.

18. A method of reducing gastric acid secretion in a mammal comprising administering an effective gastric acid secretion reducing amount of a compound named Tricyclo[3.3.1.1³,⁷]dec-2-yl [2-[[2-hydroxy-1-(hydroxymethyl)-2-phenylethyl]amino]-1-[(4-hydroxyphenyl)methyl]-1-methyl-2-oxoethyl]carbamate (mixture of [1S-[1R*(R*),2R*]] and [1S-[1R*(S*),2R*]] isomers).

19. A method of reducing gastric acid secretion in a mammal comprising administering an effective gastric acid secretion reducing amount of a compound named Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]carbamate (mixture of [1S-[1R*(R*),2R*]] and [1S-[1R*(S*),2R*]] isomers).

20. A method of reducing gastric acid secretion in a mammal comprising administering an effective gastric acid secretion reducing amount of a compound named Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate (mixture of [1S-[1R*(R*),2R*]] and [1S-[1R*(S*),2R*]] isomers).

21. A method for treating gastrointestinal ulcers in a mammal comprising administering an effective gastrointestinal ucer treating amount of a compound named Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate.

22. A method for treating gastrointestinal ulcers in a mammal comprising administering an effective gastrointestinal ulter treating amount of a comound named Tricyclo]3.3.1.1³,⁷]dec-2-yl [2-[[2-hydroxy-1-(hydroxymethyl)-2-phenylethyl]amino]-1-[(4-hydroxyphenyl)methyl]-1-methyl-2-oxoethyl]carbamate (mixture of [1S-[1R*(R*),2R*]] and [1S-[1R*(S*),2R*]] isomers.

23. A method for treating gastrointestinal ulcers in a mammal comprising administering an effective gastrointestinal ulcer treating amount of a compound named Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]carbamate (mixture of [1S-[1R*(R*),2R*]] and [1S-[1R*(S*),2R*]] isomers).

24. A method for treating gastrointestinal ulcers in a mammal comprising administering an effective gastrointestinal ulcer treating amount of a compound named Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate (mixture of [1S-[1R*(R*),2R*]] and [1S-[1R*(S*),2R*]] isomers).

* * * * *

UNITED STATES PATENT AND TRADEMARK OFFICE
CERTIFICATE OF CORRECTION

PATENT NO. : 5,331,006
DATED : July 19, 1994
INVENTOR(S) : Horwell, et. al.

It is certified that error appears in the above-indentified patent and that said Letters Patent is hereby corrected as shown below:

Column 120, line 37, the "+" should be up by the first "C" not down by the "H". Structure to appear as:

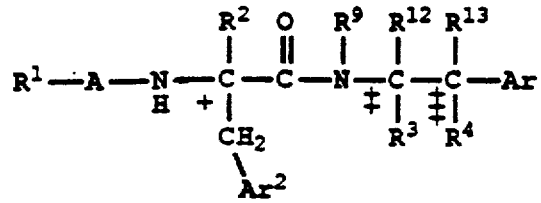

Column 125, line 8, delete " dec-2-yl " and insert instead " dec-1-yl ".

Column 125, line 50, delete " [2-[[2- " and insert instead " [2-[[1- ".

Column 126, line 22, delete " dec-2-yl- " and insert instead " dec-1-yl ".

Column 126, line 35, delete " ulter " and insert instead " ulcer ".

UNITED STATES PATENT AND TRADEMARK OFFICE
CERTIFICATE OF CORRECTION

PATENT NO. : 5,331,006
DATED : July 19, 1994
INVENTOR(S) : Horwell, et. al.

It is certified that error appears in the above-indentified patent and that said Letters Patent is hereby corrected as shown below:

Column 126, line 52, delete "dec-2-yl" and insert --"dec-1-yl--.

Signed and Sealed this

Eleventh Day of October, 1994

Attest:

BRUCE LEHMAN

*Attesting Officer*   *Commissioner of Patents and Trademarks*